(12) United States Patent
Woloszko et al.

(10) Patent No.: US 7,704,249 B2
(45) Date of Patent: *Apr. 27, 2010

(54) APPARATUS AND METHODS FOR ELECTROSURGICAL ABLATION AND RESECTION OF TARGET TISSUE

(75) Inventors: Jean Woloszko, Mountain View, CA (US); Paul O. Davison, Montara, CA (US)

(73) Assignee: ArthroCare Corporation, Austin, TX (US)

( * ) Notice: Subject to any disclaimer, the term of this patent is extended or adjusted under 35 U.S.C. 154(b) by 739 days.

This patent is subject to a terminal disclaimer.

(21) Appl. No.: 11/125,613

(22) Filed: May 9, 2005

(65) Prior Publication Data
US 2005/0251134 A1    Nov. 10, 2005

Related U.S. Application Data

(60) Provisional application No. 60/569,205, filed on May 7, 2004.

(51) Int. Cl.
*A61B 18/18* (2006.01)
(52) U.S. Cl. .......................................... 606/48; 606/46
(58) Field of Classification Search .................... 606/41, 606/45–50
See application file for complete search history.

(56) References Cited

U.S. PATENT DOCUMENTS 2,050,904 A   8/1936   Trice .......................... 219/31

(Continued)

FOREIGN PATENT DOCUMENTS

DE            3930451 A1   3/1991

EP            515867      12/1992

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner*—Michael Peffley
(74) *Attorney, Agent, or Firm*—Michael Scheele; Brian Szymczak

(57) ABSTRACT

An electrosurgical system and method for ablating, resecting, or cutting body structures, with minimal or no damage to tissue adjacent to the treatment site. The system includes an electrosurgical probe having a shaft with a shaft distal end bifurcated to provide first and second arms. First and second electrode supports are disposed on the first and second arms, respectively. At least one active electrode, in the form of a loop or partial loop, is arranged between the first and second electrode supports. A return electrode, also in the form of a loop or partial loop, is arranged between the first and second electrode supports distal to the active electrode. The active and return electrodes are configured to promote substantially high electric field intensities and associated high current densities between the active portion and the target site when a high frequency voltage is applied to the electrodes. These high current densities are sufficient to break down the tissue by processes including molecular dissociation of tissue components. In one embodiment, the high frequency voltage imparts energy to the target site to effect the vaporization and volumetric removal of a layer of tissue without causing substantial tissue damage beyond the layer of tissue ablated. In another embodiment, a fragment of target tissue is removed, with minimal or no damage to surrounding tissue, by a process including the molecular dissociation of tissue components, and the tissue fragment is retrieved for biopsy.

10 Claims, 33 Drawing Sheets

U.S. PATENT DOCUMENTS

| | | | |
|---|---|---|---|
| 2,056,377 A | 10/1936 | Wappler | 125/303 |
| 3,633,425 A | 1/1972 | Sanford | 73/356 |
| 3,799,168 A | 3/1974 | Peters | 128/303.14 |
| 3,815,604 A | 6/1974 | O'Malley et al. | 128/305 |
| 3,828,780 A | 8/1974 | Morrison, Jr. et al. | 128/275 |
| 3,850,175 A | 11/1974 | Iglesias | 128/303.15 |
| 3,901,242 A | 8/1975 | Storz | 128/303 |
| 3,920,021 A | 11/1975 | Hildebrandt | 128/303 |
| 3,939,839 A | 2/1976 | Curtiss | 128/303 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,060,087 A * | 11/1977 | Hiltebrandt et al. | 606/46 |
| 4,074,718 A | 2/1978 | Morrison, Jr. | 128/303 |
| 4,092,986 A | 6/1978 | Schneiderman | 128/303 |
| 4,116,198 A * | 9/1978 | Roos | 606/46 |
| 4,149,538 A | 4/1979 | Mrava et al. | 606/46 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,736,743 A | 4/1988 | Daikuzono | 606/28 |
| 4,737,678 A | 4/1988 | Hasegawa | 313/36 |
| 4,745,921 A | 5/1988 | Nowacki et al. | 601/4 |
| 4,762,128 A | 8/1988 | Rosenbluth | 606/192 |
| 4,765,331 A | 8/1988 | Petruzzi et al. | 128/303 |
| 4,785,806 A | 11/1988 | Deckelbaum | 606/7 |
| 4,785,823 A | 11/1988 | Eggers et al. | 128/692 |
| 4,805,616 A | 2/1989 | Pao | 128/303 |
| 4,813,429 A | 3/1989 | Eshel et al. | 600/547 |
| 4,823,791 A | 4/1989 | D'Amelio et al. | 123/303 |
| 4,832,048 A | 5/1989 | Cohen | 128/786 |
| 4,860,752 A | 8/1989 | Turner | 607/102 |
| 4,896,671 A | 1/1990 | Cunningham et al. | 600/374 |
| 4,905,674 A | 3/1990 | Nowacki et al. | 601/4 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,936,310 A | 6/1990 | Engstrom et al. | 600/486 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,968,314 A | 11/1990 | Michaels | 606/7 |
| 4,969,885 A | 11/1990 | Farin | 606/38 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 607/138 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,037,421 A | 8/1991 | Boutacoff et al. | 606/15 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,061,266 A | 10/1991 | Hakky | 606/15 |
| 5,061,938 A | 10/1991 | Zahn et al. | 343/700 MS |
| 5,078,717 A | 1/1992 | Parins et al. | 606/48 |
| 5,078,736 A | 1/1992 | Behl | 623/1 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,147,354 A | 9/1992 | Boutacoff et al. | 606/15 |
| 5,151,098 A | 9/1992 | Loertscher | 606/16 |
| 5,152,768 A | 10/1992 | Bhatta | 606/128 |
| 5,156,151 A | 10/1992 | Imran | 600/375 |
| 5,167,659 A | 12/1992 | Ohtomo et al. | 606/40 |
| 5,169,397 A | 12/1992 | Sakashita et al. | 606/27 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,209,273 A | 5/1993 | Giuffredi et al. | 141/20 |
| 5,217,455 A | 6/1993 | Tan | 606/9 |
| 5,217,457 A | 6/1993 | Delahuerga et al. | 606/42 |
| 5,217,459 A | 6/1993 | Kamerling | 606/48 |
| 5,222,938 A | 6/1993 | Behl | 604/500 |
| 5,224,953 A | 7/1993 | Morgentaler | 606/192 |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,797 A | 2/1994 | Chess | 606/9 |
| 5,290,273 A | 3/1994 | Tan | 606/9 |
| 5,290,282 A | 3/1994 | Casscells | 606/29 |
| 5,290,286 A | 3/1994 | Parins | 606/50 |
| 5,297,994 A | 3/1994 | Suzuki | 464/27 |
| 5,300,069 A | 4/1994 | Hunsberger et al. | 606/37 |
| 5,300,099 A | 4/1994 | Rudie | 607/101 |
| 5,301,687 A | 4/1994 | Wong et al. | 607/116 |
| 5,304,170 A | 4/1994 | Green | 606/9 |
| 5,306,238 A | 4/1994 | Fleenor | 606/42 |
| 5,312,395 A | 5/1994 | Tan | 606/9 |
| 5,312,400 A | 5/1994 | Bales et al. | 606/41 |
| 5,314,406 A | 5/1994 | Arias et al. | 604/21 |
| 5,318,564 A | 6/1994 | Eggers | 606/47 |
| 5,322,507 A | 6/1994 | Costello et al. | 600/105 |
| 5,324,254 A | 6/1994 | Phillips | 604/21 |
| 5,330,470 A | 7/1994 | Hagen | 606/42 |
| 5,330,518 A | 7/1994 | Neilson et al. | 607/101 |
| 5,334,140 A | 8/1994 | Philips | 604/35 |
| 5,334,183 A | 8/1994 | Wuchinich | 606/46 |

| Patent | Date | Inventor | Class |
|---|---|---|---|
| 5,336,217 A | 8/1994 | Buys et al. | 606/9 |
| 5,336,220 A | 8/1994 | Ryan et al. | 604/22 |
| 5,342,357 A | 8/1994 | Nardella | 606/40 |
| 5,366,443 A | 11/1994 | Eggers | 252/511 |
| 5,370,642 A | 12/1994 | Keller | 606/9 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,417,687 A | 5/1995 | Nardella et al. | 606/32 |
| 5,419,767 A | 5/1995 | Eggers et al. | 604/114 |
| 5,423,803 A | 6/1995 | Tankovich et al. | 606/9 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |
| 5,445,634 A | 8/1995 | Keller | 606/9 |
| 5,451,224 A | 9/1995 | Goble et al. | 606/48 |
| 5,454,809 A | 10/1995 | Janssen | 606/41 |
| 5,470,309 A | 11/1995 | Edwards et al. | 604/22 |
| 5,487,385 A | 1/1996 | Avitall | 600/374 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,500,012 A | 3/1996 | Brucker et al. | 607/122 |
| 5,514,130 A | 5/1996 | Baker | 606/41 |
| 5,554,152 A | 9/1996 | Aita | 606/7 |
| 5,556,397 A | 9/1996 | Long et al. | 606/48 |
| 5,569,242 A | 10/1996 | Lax et al. | 606/42 |
| 5,569,244 A | 10/1996 | Hahnen | 606/46 |
| 5,571,100 A | 11/1996 | Goble et al. | 606/41 |
| 5,584,872 A | 12/1996 | LaFontaine et al. | 607/117 |
| 5,609,151 A | 3/1997 | Mulier et al. | 128/642 |
| 5,633,578 A | 5/1997 | Eggers et al. | 323/301 |
| 5,647,869 A | 7/1997 | Goble et al. | 606/37 |
| 5,658,278 A | 8/1997 | Imran et al. | 606/41 |
| 5,658,280 A | 8/1997 | Issa | 606/46 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,725,524 A | 3/1998 | Mulier et al. | 606/41 |
| 5,766,153 A | 6/1998 | Eggers et al. | 604/114 |
| 5,788,694 A | 8/1998 | Vancaillie | 606/45 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,836,875 A | 11/1998 | Webster, Jr. | 600/374 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,976,129 A * | 11/1999 | Desai | 606/40 |
| 5,993,445 A * | 11/1999 | Issa | 606/46 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,152,920 A * | 11/2000 | Thompson et al. | 606/41 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,025 B1 * | 3/2001 | Grossi et al. | 606/46 |
| 6,203,542 B1 | 3/2001 | Ellsberry et al. | 606/41 |
| 6,210,402 B1 | 4/2001 | Olsen et al. | 606/32 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,427,089 B1 | 7/2002 | Knowlton | 607/101 |
| 6,432,103 B1 | 8/2002 | Ellsberry et al. | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,517,498 B1 | 2/2003 | Burbank et al. | 600/564 |

| | | | |
|---|---|---|---|
| 6,530,922 B2 | 3/2003 | Cosman | 606/34 |
| 6,578,579 B2 | 6/2003 | Burnside | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,960,204 B2 | 11/2005 | Eggers et al. | 606/32 |
| 6,974,453 B2 | 12/2005 | Woloszko et al. | 606/41 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/32 |
| 2002/0029036 A1 | 3/2002 | Goble et al. | 606/38 |
| 2002/0095151 A1* | 7/2002 | Dahla et al. | 606/41 |
| 2003/0013986 A1 | 1/2003 | Saadat | 600/549 |
| 2003/0028189 A1 | 2/2003 | Woloszko et al. | 604/45 |
| 2003/0088245 A1 | 5/2003 | Woloszko et al. | 606/41 |
| 2003/0158545 A1 | 8/2003 | Hovda et al. | 606/32 |
| 2003/0171743 A1 | 9/2003 | Tasto et al. | 606/32 |
| 2003/0208194 A1 | 11/2003 | Hovda et al. | 606/41 |
| 2003/0208196 A1 | 11/2003 | Stone | 606/41 |
| 2003/0212395 A1 | 11/2003 | Woloszko et al. | 606/32 |
| 2003/0212396 A1 | 11/2003 | Eggers et al. | 606/41 |
| 2004/0024399 A1 | 2/2004 | Sharps et al. | 606/32 |
| 2004/0049180 A1 | 3/2004 | Sharps et al. | 606/32 |
| 2004/0054366 A1 | 3/2004 | Davison et al. | 606/45 |
| 2004/0116922 A1 | 6/2004 | Hovda et al. | 606/41 |
| 2004/0127893 A1 | 7/2004 | Hovda | 606/41 |
| 2004/0153057 A1 | 8/2004 | Davison | 600/410 |
| 2004/0186469 A1 | 9/2004 | Woloszko et al. | 606/41 |
| 2004/0230190 A1 | 11/2004 | Dahla et al. | 604/41 |
| 2005/0004634 A1 | 1/2005 | Hovda et al. | 606/41 |
| 2005/0010205 A1 | 1/2005 | Hovda et al. | 606/32 |
| 2005/0119650 A1 | 6/2005 | Sanders et al. | 424/426 |
| 2005/0131402 A1 | 6/2005 | Ciarrocca et al. | 600/450 |
| 2005/0187543 A1 | 8/2005 | Underwood et al. | 606/41 |
| 2005/0234439 A1 | 10/2005 | Underwood et al. | 606/32 |
| 2005/0251134 A1 | 11/2005 | Woloszko et al. | 606/32 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095026 A1 | 5/2006 | Hovda et al. | 606/32 |
| 2006/0095031 A1 | 5/2006 | Ormsby | 606/34 |
| 2006/0129145 A1 | 6/2006 | Ormsby et al. | 606/41 |
| 2006/0178670 A1 | 8/2006 | Woloszko et al. | 606/48 |
| 2006/0189971 A1 | 8/2006 | Eggers et al. | 606/32 |
| 2006/0253117 A1 | 11/2006 | Hovda et al. | 128/898 |
| 2006/0259025 A1 | 11/2006 | Dahla | 607/108 |
| 2007/0010808 A1 | 1/2007 | Dahla | 606/41 |
| 2007/0010809 A1 | 1/2007 | Sanders et al. | 606/32 |

FOREIGN PATENT DOCUMENTS

| | | |
|---|---|---|
| EP | 597463 | 5/1994 |
| EP | 0703461 A2 | 3/1996 |
| EP | 0740926 A2 | 11/1996 |
| EP | 0 754 437 | 1/1997 |
| EP | 0 694 290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| JP | 57-183850 | 11/1982 |
| JP | 5-506801 | 10/1993 |
| NL | 05/000434 | 12/2006 |
| WO | 90/03152 | 4/1990 |
| WO | 90/07303 | 7/1990 |
| WO | 91/17717 | 11/1991 |
| WO | 92/21278 | 12/1992 |
| WO | 93/13816 | 7/1993 |
| WO | 93/20747 | 10/1993 |
| WO | 94/04220 | 3/1994 |
| WO | 94/08654 | 4/1994 |
| WO | 94/14383 | 7/1994 |
| WO | 94/26228 | 11/1994 |
| WO | 95/34259 | 12/1995 |
| WO | 96/00042 | 1/1996 |
| WO | 96/23449 | 8/1996 |
| WO | 96/39914 | 12/1996 |
| WO | 97/00646 | 1/1997 |
| WO | 97/00647 | 1/1997 |
| WO | 97/24073 | 7/1997 |
| WO | 97/24074 | 7/1997 |
| WO | 97/24993 | 7/1997 |
| WO | 97/24994 | 7/1997 |
| WO | 97/48345 | 12/1997 |
| WO | 97/48346 | 12/1997 |
| WO | 98/07468 | 2/1998 |
| WO | 98/27879 | 7/1998 |
| WO | 98/27880 | 7/1998 |
| WO | 99/51155 | 10/1999 |
| WO | 99/51158 | 10/1999 |
| WO | 01/87154 | 5/2001 |
| WO | 02/36028 | 5/2002 |
| WO | 2005/125287 | 12/2005 |

OTHER PUBLICATIONS

Codman & Shurtleff, Inc. "The Malis Bipolar Coagulating and Bipolar Cutting System CMC-II" brochure, early, 2 pgs, 1991.

Codman & Shurtleff, Inc. "The Malis Bipolar Electrosurgical System CMC—III Instruction Manual", 15 pgs, Jul. 1991.

Cook et al., "Therapeutic Medical Devices: Application and Design", Prentice Hall, Inc., 3pgs, 1982.

Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" *Bio-Medical Engineering* vol. 4, pp. 206-216, May 1969.

Elsasser, V.E. et al., "An Instrument for Transurethral Resection without Leakage of Current" *Acta Medicotechnica* vol. 24, No. 4, pp. 129-134, 1976.

Geddes, "Medical Device Accidents: With Illustrative Cases" CRC Press, 3 pgs, 1998.

Honig, W., "The Mechanism of Cutting in Electrosurgery" *IEEE* pp. 58-65, 1975.

Kramolowsky et al. "The Urological App of Electorsurgery" *J. of Urology* vol. 146, pp. 669-674, 1991.

Kramolowsky et al. "Use of 5F Bipolar Electrosurgical Probe in Endoscopic Urological Procedures" *J. of Urology* vol. 143, pp. 275-277, 1990.

Lee, B et al. "Thermal Compression and Molding of Artherosclerotic Vascular Tissue with Use" JACC vol. 13(5), pp. 1167-1171, 1989.

Letter from Department of Health to Jerry Malis dated Jan, 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, in Vitro Tissue Ablation Studies and in Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg, 1995.

Malis, L., "Instrumentation for Microvascular Neurosurgery" *Cerebrovascular Surgery*, vol. 1, pp. 245-260, 1985.

Malis, L., "New Trends in Microsurgery and Applied Technology," *Advanced Technology in Neurosurgery*, pp. 1-16, 1988.

Malis, L., "The Value of Irrigation During Bipolar Coagulation" See ARTC 21602, 1 pg, Apr. 9, 1993.

Nardella, P.C., *SPIE* 1068: pp. 42-49, Radio Frequency Energy and Impedance Feedback, 1989.

O'Malley, Schaum's Outline of Theory and Problems of Basic Circuit Analysis, McGraw-Hill, $2^{nd}$ Ed., pp. 3-5, 1992.

Olsen MD, Bipolar Laparoscopic Cholecstectomy Lecture (marked confidential), 12 pgs, Oct. 7, 1991.

Pearce, John A. "Electrosurgery", pp. 17, 69-75, 87, John Wiley & Sons, New York, 1986.

Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" *Gastroenterology* vol. 74(3), pp. 527-534, 1978.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.

Ramsey et al., "A Comparison of Bipolar and Monopolar Diathermy Probes in Experimental Animals", *Urological Research* vol. 13, pp. 99-102, 1985.

Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.

Shuman, "Bipolar Versus Monopolar Electrosurgery: Clinical Applications," *Dentistry Today*, vol. 20, No. 12, 7 pgs, Dec. 2001.

Slager et al. "Spark Erosion of Arteriosclerotic Plaques" *Z. Kardiol.* 76:Suppl. 6, pp. 67-71, 1987.

Slager et al. "Vaporization of Atherosclerotice Plaques by Spark Erosion" *JACC* 5(6): pp. 1382-1386, Jun. 1985.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the $55^{th}$ Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550 Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of *Escherichia coli* by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.

Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.

Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.

Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.

Stoffels, E. et al., "Plasma Needle for in Vivo Medical Treatment: Recent Developments and Perspectives", Plasma Sources Sci. Technol. 15, pp. S169-S180, Oct. 6, 2006.

Swain, C.P., et al., "Which Electrode, A Comparison of four endoscopic methods of electrocoagulation in experimental bleeding ulcers" *Gut* vol. 25, pp. 1424-1431, 1987.

Tucker, R. et al. "A Comparison of Urologic Application of Bipolar Versus Monopolar Five French Electrosurgical Probes" *J. of Urology* vol. 141, pp. 662-665, 1989.

Tucker, R. et al. "In vivo effect of 5 French Bipolar and Monopolar Electrosurgical Probes on the Porcine Bladder" *Urological Research* vol. 18, pp. 291-294, 1990.

Tucker, R. et al., "Demodulated Low Frequency Currents from Electrosurgical Procedures," *Surgery, Gynecology and Obstetrics*, 159:39-43, 1984.

Tucker, R. et al., Abstract P14-11, p. 248, "A Bipolar Electrosurgical Turp Loop" Nov. 1989.

Valley Forge Scientific Corp., "Summary of Safety and Effective Information from 510K", 2pgs, 1991.

Valley Forge's New Products, CLINICA 475, 5, Nov. 6, 1991.

Valleylab SSE2L Instruction Manual, 11 pgs, Jan. 6, 1983.

Valleylab, Inc. "Valleylab Part No. 945 100 102 A" Surgistat Service Manual, pp. 1-46, Jul. 1988.

Wattiez, Arnaud et al., "Electrosurgery in Operative Endoscopy," Electrosurgical Effects, Blackwell Science, pp. 85-93, 1995.

Wyeth, "Electrosurgical Unit" pp. 1181-1202.

Buchelt, et al. "Excimer Laser Ablation of Fibrocartilage: An in Vitro and in Vivo Study", Lasers in Surgery and Medicine, vol. 11, pp. 271-279, 1991.

Costello et al., "Nd: YAG Laser Ablation of the Prostate as a Treatment for Benign Prostatic Hypertrophy", Lasers in Surgery and Medicine, vol. 12, pp. 121-124, 1992.

Rand et al., "Effect of Elecctrocautery on Fresh Human Articular Cartilage", J. Arthro. Surg., vol. 1, pp. 242-246, 1985.

PCT International Search Report for PCT/US96/04647, 1 pg, Mailed Aug. 26, 1996.

PCT International Search Report for PCT/US97/12266, 1 pg, Mailed Sep. 9, 1997.

PCT Notification of International Preliminary Examination Report, 4 pgs, Mailed Jun. 18, 1998.

PCT Notification of International Preliminary Examination Report, 4 pgs, Mailed Jan. 16, 1997.

EP Supplementary Search Report for EP96910745, 6 pgs, Mailed Sep. 3, 1998.

EP Supplementary Search Report for EP97933451 3 pgs Mailed, Dec. 16, 1999.

BiLAP IFU 910033-002 Rev A for BiLAP Model 3527, L-Hook; BiLAP Model 3525, J-Hook; BiLAP Model 3529, High Angle, Nov. 30, 1993.

BiLAP IFU 910026-001 Rev A for BiLAP Model 3525, J-Hook, May 20, 1991.

BiLAP Generator Settings, Jun. 1991.

BiLAP Production Drawing Hook Loop BiLAP Assy w/Suction & Irrigation Foot Switching, Jun. 13, 1991.

Tucker et al. "The interaction between electrosurgical generators, endroscopic electrodes, and tissue," Gastrointestinal Endoscopy, vol. 38, No. 2, pp. 118-122, 1992.

* cited by examiner

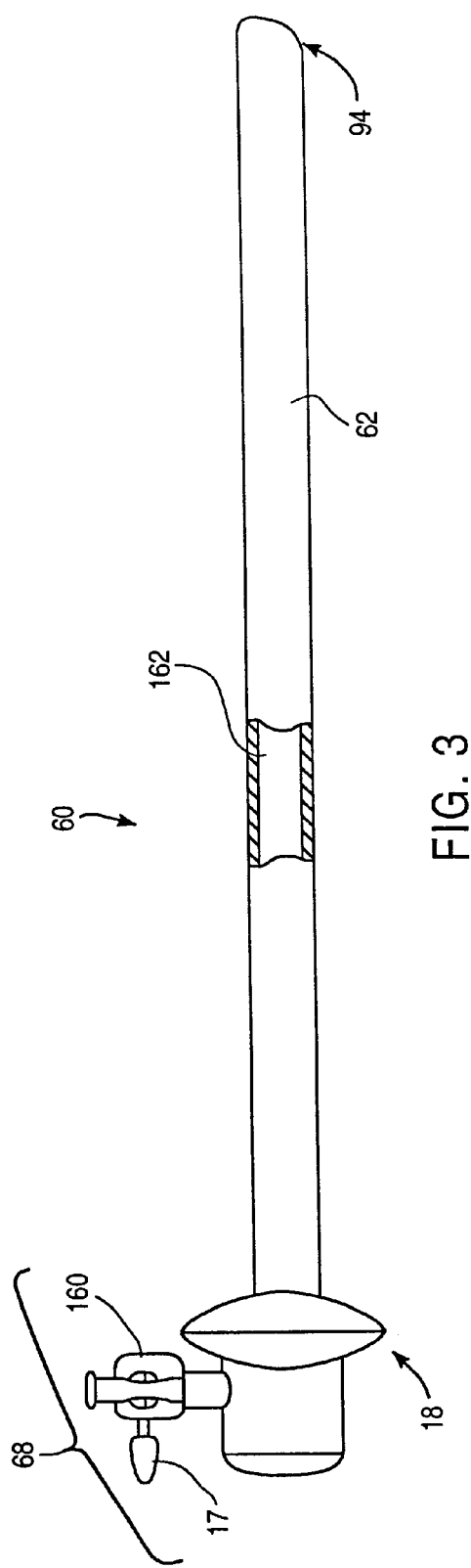
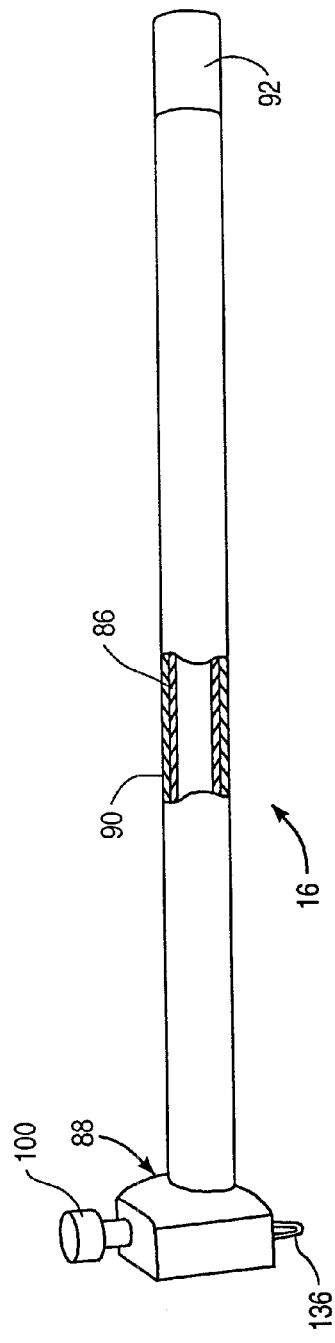
FIG. 3
FIG. 4

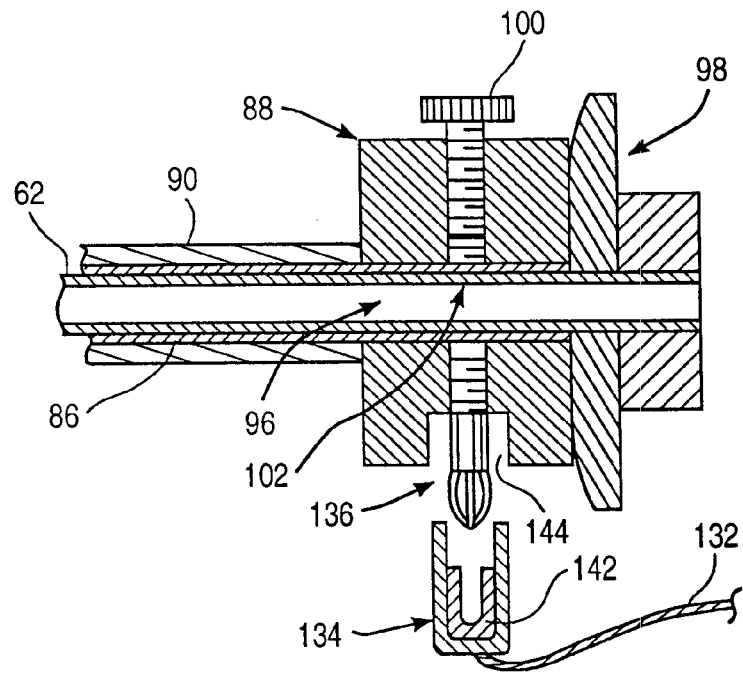
FIG. 5
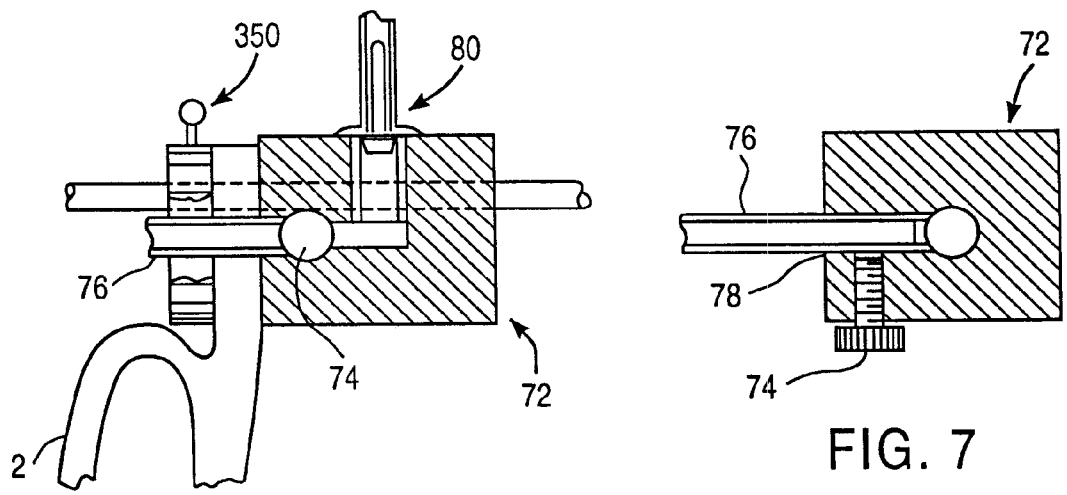
FIG. 6
FIG. 7

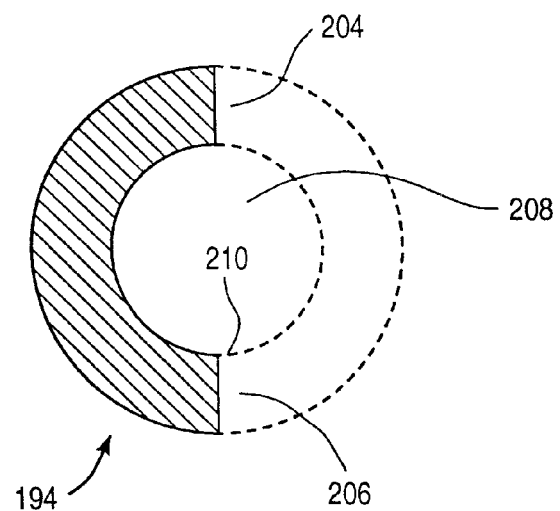
FIG. 14
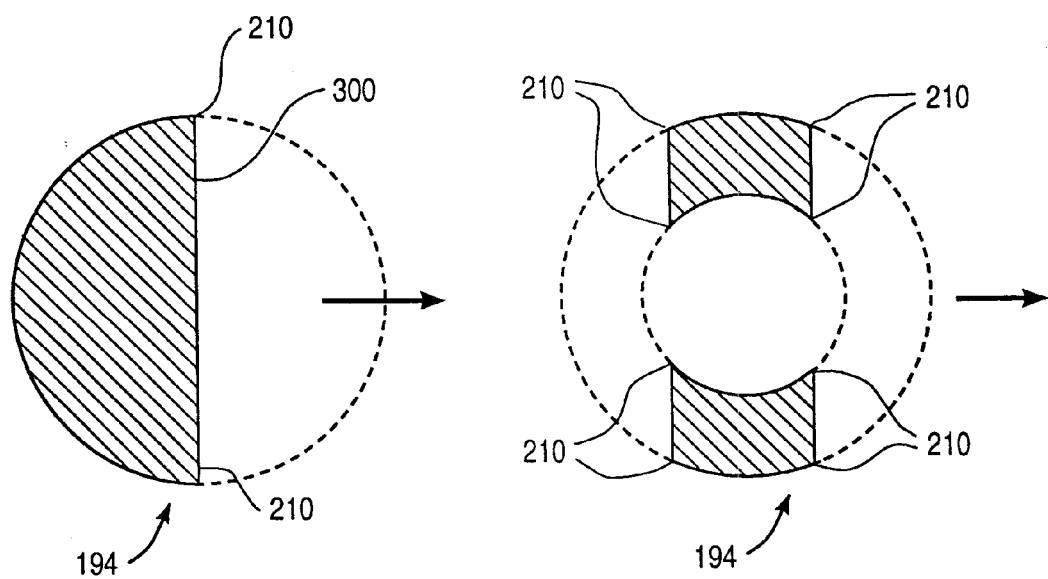
FIG. 15A
FIG. 15B

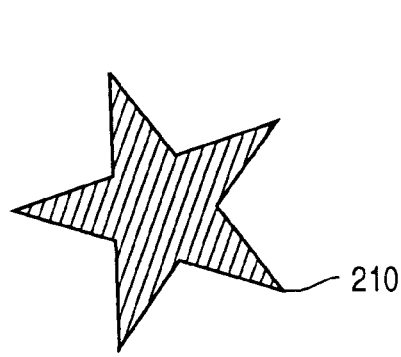
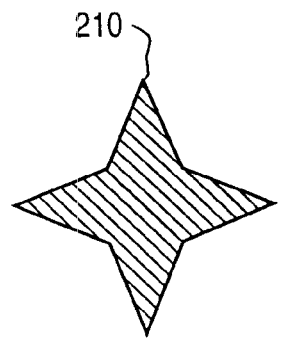
FIG. 16A	FIG. 16B
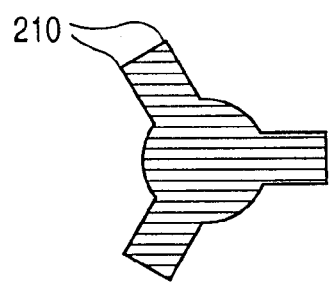
FIG. 16C
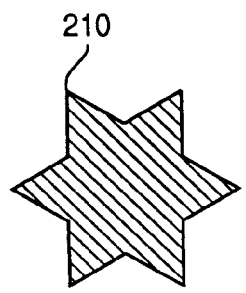
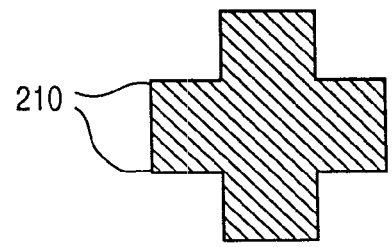
FIG. 16D	FIG. 16E

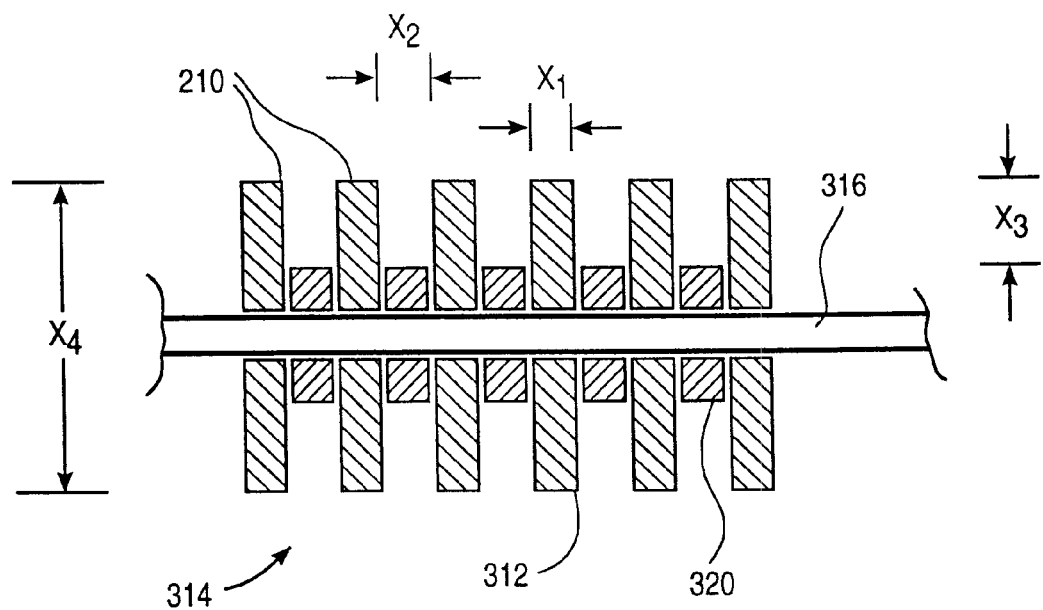
FIG. 19
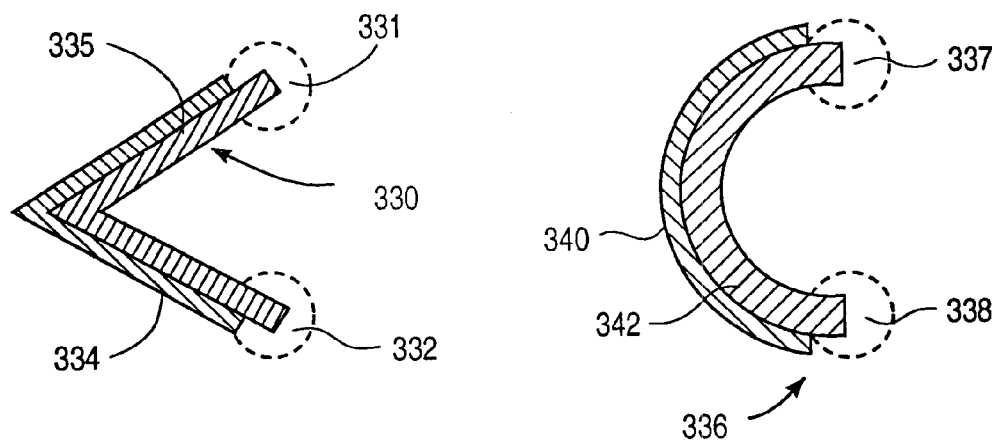
FIG. 20A
FIG. 20B

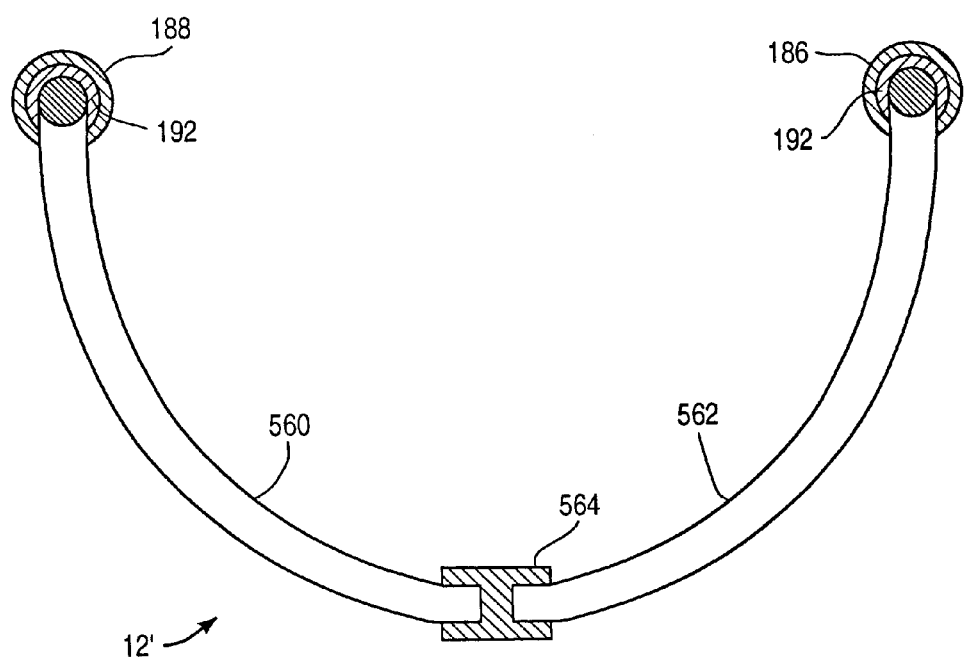
FIG. 23A
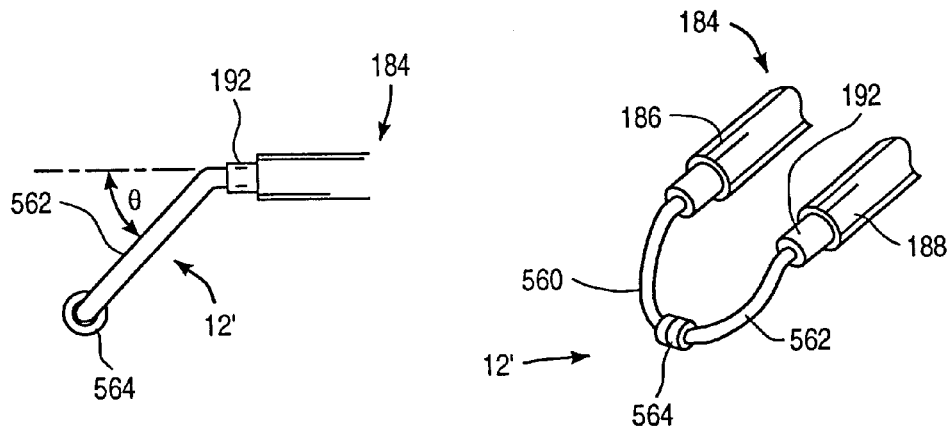
FIG. 23B
FIG. 23C

APPARATUS AND METHODS FOR ELECTROSURGICAL ABLATION AND RESECTION OF TARGET TISSUE

CROSS-REFERENCE TO RELATED APPLICATIONS

This application claims priority to U.S. provisional application No. 60/569,205, filed May 7, 2004.

This application incorporates by reference U.S. patent application Ser. No. 09/796,094, filed Feb. 28, 2001, which is a continuation-in-part of U.S. patent application Ser. No. 09/571,343, filed May 16, 2000, now U.S. Pat. No. 6,575,968, which is a Divisional of U.S. patent application Ser. No. 08/687,792, filed Jul. 18, 1996, now U.S. Pat. No. 5,843,019, which is a continuation-in-part of application Ser. No. 08/561,958, filed on Nov. 22, 1995, now U.S. Pat. No. 5,697,882, which is a continuation-in-part of application Ser. No. 08/485,219, filed on Jun. 7, 1995, now U.S. Pat. No. 5,697,281, which is a continuation-in-part of U.S. patent application Ser. No. 08/446,767, filed Jun. 2, 1995, now U.S. Pat. No. 5,697,909, which was a continuation-in-part of application Ser. No. 08/059,681, filed on May 10, 1993 now abandoned, which is a continuation-in-part of application Ser. No. 07/958,977, filed on Oct. 9, 1992, now U.S. Pat. No. 5,366,443, which is a continuation-in-part of application Ser. No. 07/817,575, filed on Jan. 7, 1992 now abandoned, the full disclosures of which are incorporated herein by reference.

BACKGROUND OF THE INVENTION

The present invention relates generally to the field of electrosurgery and, more particularly, to surgical devices and methods which employ high frequency electrical energy to cut, ablate, resect, coagulate, or otherwise modify target tissue. The present invention also relates to apparatus and methods for volumetrically removing tissue from a target site by a cool ablation (Coblation®) procedure involving molecular dissociation of tissue components, and for electrosurgically resecting one or more fragments of target tissue for biopsy.

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on external grounding of the patient, where the surgical device defines only a single electrode pole. Bipolar devices comprise both an active electrode and a return electrode for the application of current between their surfaces.

Conventional electrosurgical methods generally reduce patient bleeding and trauma associated with tissue cutting operations and improve the surgeon's visibility. These electrosurgical devices and procedures, however, suffer from a number of disadvantages. For example, monopolar electrosurgery methods generally direct electric current along a defined path from the exposed or active electrode through the patient's body to the return electrode, which is externally attached to a suitable location on the patient's skin. In addition, since the defined path through the patient's body has a relatively high electrical impedance, large voltage differences must typically be applied between the active and return electrodes to generate a current suitable for cutting or coagulation of the target tissue. This current, however, may inadvertently flow along localized, non-defined pathways in the body having less impedance than the defined electrical path. This situation will substantially increase the current flowing through these non-defined paths, possibly causing damage to or destroying tissue along and surrounding such pathways.

Another limitation of conventional bipolar and monopolar electrosurgery devices is that they are not suitable for the precise removal (ablation) of tissue. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. The tissue is parted along the pathway of vaporized cellular fluid, inducing undesirable collateral tissue damage in regions surrounding the target tissue site.

In addition, conventional electrosurgical methods are generally ineffective for ablating certain types of tissue, and in certain types of environments within the body. For example, loose or elastic connective tissue, such as the synovial tissue in joints, is extremely difficult (if not impossible) to remove with conventional electrosurgical instruments because the flexible tissue tends to move away from the instrument when it is brought against this tissue. Since conventional techniques rely mainly on conducting current through the tissue, they are not effective when the instrument cannot be brought adjacent to or in contact with the elastic tissue for a long enough period of time to energize the electrode and conduct current through the tissue.

In an effort to overcome at least some of these limitations of electrosurgery, laser apparatus have been developed for use in arthroscopic and other procedures. Lasers do not suffer from electrical shorting in conductive environments, and certain types of lasers allow for very controlled cutting with limited depth of necrosis. Despite these advantages, laser devices suffer from their own set of deficiencies. Firstly, laser equipment can be very expensive because of the costs associated with the laser light sources. Moreover, those lasers which permit acceptable depths of necrosis (such as eximer lasers, erbium:YAG lasers, and the like) provide a very low volumetric ablation rate, which is a particular disadvantage in cutting and ablation of fibrocartilage, articular cartilage, and meniscal tissue. The holmium:YAG and Nd:YAG lasers provide much higher volumetric ablation rates, but are much less able to control depth of necrosis than are the slower laser devices. The $CO_2$ lasers provide high rates of ablation and low depth of tissue necrosis, but cannot operate in a liquid-filled cavity.

Bipolar electrosurgical devices have an inherent advantage over monopolar devices in that the return current path does not flow through the patient beyond the immediate site of application of the bipolar electrodes. Thus, bipolar electrosurgery avoids inadvertent stimulation of nerves and nerve damage in the general vicinity of the treatment site. Avoidance of nerve damage is of importance, for example, when targeting tissue such as the prostate gland, where damage to surrounding nerves could result in impotence and/or incontinence.

Conventional, monopolar electrosurgical techniques have favored use of non-conductive (electrolyte-free) media, such as glycine solution, as an irrigant and distension medium at the target site. However, electrolyte-free media have the disadvantage of potentially causing adverse physiological effects in the form of water intoxication, for example, if glycine solution enters the circulation via a severed vein. Such water intoxication is due to dilution of serum sodium by the electrolyte-free medium. Bipolar electrosurgical apparatus and methods, according to the present invention, allow the use of isotonic saline as irrigant and distension medium, thereby eliminating problems related to water intoxication of the patient.

The instant invention provides improved apparatus, systems, and methods for the electrosurgical ablation and cutting of tissue. These systems and methods are capable of selectively cutting and ablating tissue in a precisely controlled manner, with little or no damage to non-target tissue.

SUMMARY OF THE INVENTION

The present invention provides a system and method for selectively applying electrical energy to structures within or on the surface of a patient's body. The system and method allow the surgical team to perform electrosurgical interventions, such as ablation and cutting of body structures, with little or no damage to non-target tissue adjacent the treatment site. The system and method of the present invention are particularly useful for surgical procedures within accessible sites of the body that are suitable for electrode loop resection, such as the resection of prostate tissue (e.g., transurethral resection of the prostate (TURP)) and leiomyomas (fibroids) located within the uterus.

A system according to one aspect of the present invention comprises an electrosurgical probe having a shaft with a proximal end, a distal end, and at least one active electrode at or near the distal end. A connector may be provided at the proximal end of the shaft for electrically coupling the active electrode to a high frequency voltage source. The active electrode includes at least one active portion having a surface geometry configured to promote substantially high electric field intensities and associated current densities between the active portion and the target site when a high frequency voltage is applied to the electrodes. These high electric field intensities and current densities are sufficient to break down the tissue by processes including molecular dissociation or disintegration of tissue components. The high frequency voltage imparts energy to the target site to ablate a layer of tissue without causing substantial tissue necrosis beyond the boundary of the layer of tissue ablated. This ablative process can be precisely controlled to effect the volumetric removal of tissue as thin as a few layers of cells with minimal or no damage to surrounding or underlying tissue structures.

In an exemplary embodiment, the high electric field intensities at the active portion of the active electrode may be generated by providing an electrically conductive fluid, such as isotonic saline, at the active electrode and/or the target site, and applying a high frequency voltage that is sufficient to vaporize the electrically conductive fluid over at least a portion of the active electrode in the region between the active portion of the active electrode and the target tissue. Since the vapor layer or vaporized region has a relatively high electrical impedance, it minimizes current flow into the electrically conductive fluid. This ionization, under the conditions described herein, induces the discharge of energetic electrons and photons from the vapor layer to the surface of the target tissue. A more detailed description of this cold ablation phenomenon, termed Coblation®, can be found in commonly assigned U.S. Pat. No. 5,683,366 the complete disclosure of which is incorporated herein by reference.

At least one return electrode is preferably spaced from the active electrode(s) a sufficient distance to prevent arcing therebetween at the voltages suitable for tissue removal and or heating, and to prevent contact of the return electrode(s) with the tissue. The current flow path between the active and return electrodes may be generated by immersing the target site within electrically conductive fluid (as is typical in arthroscopic and hysteroscopic procedures), or by directing an electrically conductive fluid along a fluid path past the return electrode and to the target site (e.g., in open procedures). Alternatively, the electrodes may be positioned within a viscous electrically conductive fluid, such as a gel, at the target site, and the active and return electrode(s) submersed within the conductive gel. The electrically conductive fluid will be selected to have sufficient electrical conductivity to allow current to pass therethrough from the active to the return electrode(s), and such that the electrically conductive fluid ionizes into a plasma when subject to sufficient electrical energy, as discussed below. In the exemplary embodiment, the conductive fluid is isotonic saline, although other fluids may be selected.

In a specific embodiment, tissue ablation results from molecular dissociation or disintegration processes. Conventional electrosurgery ablates or cuts through tissue by rapidly heating the tissue until cellular fluids explode, producing a cutting effect along the pathway of localized heating. The present invention volumetrically removes tissue, e.g., cartilage tissue, in a cool ablation process known as Coblation®, wherein thermal damage to surrounding tissue is avoided or minimized. During this process, a high frequency voltage applied to the active electrode(s) is sufficient to vaporize an electrically conductive fluid (e.g., gel or saline) between the electrode(s) and the tissue. Within the vaporized fluid, a plasma is formed and charged particles (e.g., electrons) cause the molecular breakdown or disintegration of tissue components in contact with the plasma. This molecular dissociation is accompanied by the volumetric removal of the tissue. This process can be precisely controlled to effect the volumetric removal of tissue as thin as 10 to 50 microns with minimal heating of, or damage to, surrounding or underlying tissue structures. A more complete description of this Coblation® phenomenon is described in commonly assigned U.S. Pat. No. 5,683,366, the complete disclosure of which is incorporated herein by reference.

The present invention offers a number of advantages over conventional electrosurgery, microdebrider, shaver, and laser techniques for removing soft tissue in urogenital, arthroscopic, sinus, or other surgical procedures. The ability to precisely control the volumetric removal of tissue results in a field of tissue ablation or removal that is very defined, consistent, and predictable. In one embodiment, the shallow depth of tissue heating also helps to minimize, or completely eliminate, damage to adjacent, non-target tissue. In addition, small blood vessels within the target tissue may be simultaneously cauterized and sealed as the tissue is removed to continuously maintain hemostasis during a procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Isotonic saline is a suitable electrolytic medium for irrigation and/or distension of the treatment site because it transparent to visible light, and generally exerts no adverse physiological effect on the patient.

According to one aspect of the invention, one or more surfaces of the active electrode may be configured to provide high electric field intensities and current densities thereat, upon application of a high frequency voltage. Suitable electrode surface geometries for producing sufficiently high electric field intensities to reach the threshold conditions for vapor layer formation may be obtained by having sharp edges and/ or corners at the active portion of the active electrode(s). Alternatively, the electrode(s) may be specifically designed to increase the edge/surface area ratio of the active portion. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a solid or hollow wire electrode to form D or C shaped wires, respectively, with edges facing in the cutting direction. Alternatively, material can be removed at closely spaced intervals along the electrode length to form transverse grooves, slots, threads, holes or the like along the electrodes.

Additionally or alternatively, the active electrode surface(s) may be modified through chemical, electrochemical or abrasive methods to create a multiplicity of surface asperities on the electrode surface. The asperities on the surface of the active electrode(s) promote localized high current densities which, in turn, promote bubble nucleation at the site of the asperities whose enclosed density (i.e., vapor density) is below the critical density to initiate ionization breakdown within the bubble. For example, surface asperities may be created by etching the active electrodes with etchants having a pH less than 7.0 or by using a high velocity stream of abrasive particles (e.g., grit blasting) to create asperities on the surface of an elongated electrode.

In one embodiment, the invention provides an electrosurgical probe which includes a return electrode spaced proximally from the active electrode. The return electrode may be integral with the shaft of the probe, or it may be separate from the shaft (e.g., arranged on a separate liquid supply instrument). In an exemplary embodiment, the return electrode defines a fluid pathway for flow of electrically conductive fluid therethrough. The fluid is directed past the surface of the return electrode and over the active electrode to thereby provide a return current flow path between the target tissue and the return electrode. A more complete description of methods and apparatus for generating a liquid current flow path between the active and return electrodes can be found in U.S. Pat. No. 5,697,281, the complete disclosure of which is incorporated herein by reference.

In another aspect of the invention, the active electrode will also have a "non-active" portion or surface to selectively reduce undesirable current flow from the non-active portion or surface into tissue or surrounding electrically conductive fluids (e.g., isotonic saline, blood or blood/non-conducting irrigant mixtures). Typically, the "non-active" electrode portion will be coated with an electrically insulating material. This can be accomplished, for example, with plasma deposited coatings of an insulating material, thin-film deposition of an insulating material (e.g., SiO2 or Si3N4) using evaporative or sputtering techniques, dip coating, or by providing an electrically insulating support member to electrically insulate a portion of the external surface of the electrode. The electrically insulated non-active portion of the active electrode(s) allows the surgeon to selectively ablate tissue, while minimizing necrosis or ablation of surrounding non-target tissue or other body structures.

In one representative embodiment, an electrosurgical resecting instrument is provided having a resecting electrode on the distal end of a shaft and coupled to a high frequency voltage source. The resecting electrode is configured to fit within a working end of a resectoscope (discussed below) and to remove small portions of tissue (e.g., chips of tissue). Preferably, the resecting electrode has an elongate body with first and second ends disposed near the distal end of the shaft to form a loop electrode for removing tissue portions and for providing visibility through the loop (i.e., with an optical viewing scope positioned within the resectoscope). The loop electrode may have a variety of shapes, e.g., V-shaped, square or the like. In one embodiment, the loop electrode has a semi-circular-shape to facilitate rapid resection of tissue chips from the target site.

The elongate body of the loop electrode includes an active portion with a surface geometry configured to promote substantially high electric field intensities and associated current densities between the active portion and the target site when a high frequency voltage is applied to the electrode. Preferably, the electric field intensities generated around the active portion of the loop electrode are sufficient to reach the threshold conditions for vapor layer formation between the electrode and the tissue, as discussed above. To that end, the active portion of the loop electrode can be formed with edges, corners, holes, surface asperities or a combination thereof, to maximize the electric field intensities around the active electrode.

In one configuration, the loop electrode will have a semi-circular cross-section formed by, for example, removing material from a round wire or hollow cylinder to form two or more edges on one side of the loop electrode. In this configuration, the edges are typically oriented substantially orthogonal to the longitudinal axis of the shaft so that they will face the tissue as the shaft is moved axially in the cutting direction. This orientation facilitates formation of the vapor layer between the electrode edges and the tissue. The opposite or non-active side of the electrode may include an insulating layer to selectively reduce undesirable current flow from the non-active portion into tissue or surrounding electrically conductive fluids.

In one embodiment, the elongate body of the resecting loop electrode lies in a plane that defines an obtuse angle with the shaft. In this way, the resecting loop electrode defines an obtuse angle with the usual cutting direction as the surgeon moves the resecting instrument parallel to the surface of the target tissue. In this configuration, the resecting loop electrode will define an angle of about 110° to 160° with the shaft, and preferably about 120° to 140°. This orientation increases the portion of the resecting loop electrode that is in contact with the tissue rather than exposed to electrically conductive fluid. Consequently, it significantly improves the ease of initiating the requisite conditions for formation of the vapor layer to ablate and cut tissue. In addition, this resecting loop electrode orientation increases the duration of electrode contact with tissue, thereby improving hemostasis of the resected tissue.

The resecting loop instrument of the present invention will usually include a return electrode for completing the current path between the active electrode and the tissue site. The return electrode may be formed on the shaft of the resecting loop electrode, on the resectoscope, or on a separate instrument. In one configuration, the return electrode is formed on a separate return electrode oversheath that includes an electrically conducting hollow tube sized to receive the resecting loop shaft so that the active loop electrode extends beyond the distal end of the hollow tube. The return electrode tube is insulated on its inner and outer surfaces except for an exposed portion that is spaced proximally from the active electrode to generate a current flow path therebetween. The return electrode oversheath may include a fluid path for allowing electrically conductive fluid to flow over the exposed portion to facilitate the formation of the current flow path.

In an alternative embodiment of the resecting loop instrument, the return electrode sheath is insulated on its inner and outer surfaces except for an exposed portion that extends beyond (i.e., overhangs) the distal end of the sheath. The exposed portion generates a current flow path between the resecting loop electrode and the return electrode. If the return electrode is used in conjunction with and positioned over an insulated resecting loop shaft, the return electrode oversheath will be insulated on its outer surface only.

In an exemplary embodiment, the return electrode oversheath includes a proximal hub for connecting the oversheath to a conventional or specialized resectoscope, such as those commercially available from Circon/ACMI of Stamford, Conn. (under the tradename of "USA Elite System Resectoscope") and Olympus Corporation of Lake Success, N.Y. (under the tradename of "OES Resectoscope", Model No. A-2012). In this configuration, the return electrode tube is sized to receive the resectoscope shaft, which usually includes a viewing lumen to provide viewing of the surgical site. The proximal hub will also include a suitable electrical connector for electrically coupling the return electrode to an electrosurgical generator.

In another aspect, the invention provides an electrosurgical probe including an elongate body and a distal electrode assembly. The elongate body includes a first shaft at its distal end, wherein the first shaft is bifurcated to form a first arm and a second arm. A first electrically insulating electrode support and a second electrode support are disposed on the first and second arms, respectively. According to one aspect of the invention, the first shaft includes a first bend and a second bend. The bifurcated configuration of the first shaft, together with the first and second bends, facilitates viewing of the electrode assembly, from a proximal location during use of the probe. The electrode assembly provides a "double loop" electrode configuration including an active electrode and a return electrode, the latter located distal to the former In one embodiment, each of the first and second electrode supports includes an axial portion and a curved portion, wherein the return electrode and the active electrode are suspended between the curved portions.

In one embodiment, the surface area of the return electrode is greater than that of the active electrode. The greater the return electrode to active electrode surface area ratio, the greater the current density at the active electrode. The surface area ratio is affected by the relative lengths and/or perimeter dimensions of the return and active electrodes. According to one aspect of the invention, a filament of the return electrode is longer than a filament of the active electrode. According to another aspect of the invention, the circumference or perimeter of the return electrode filament is greater than the circumference or perimeter of the active electrode filament. In one embodiment, the active electrode lies in a first plane, and the return electrode lies in a second plane substantially parallel to the first plane, wherein the first plane is arranged at an acute angle with respect to the longitudinal axis of the probe. According to another aspect of the invention, the return electrode filament is separated from the active electrode filament by an electrode gap, which remains substantially constant over the entire length of the active electrode filament.

In another aspect, an electrosurgical probe of the invention includes an attachment unit, coupled to the elongate body, wherein the attachment unit is adapted for removably attaching the probe to another surgical device. In one aspect, the attachment unit is adapted for attaching the probe to an endoscope, such that the probe is aligned with various components, such as an introducer sheath or an optical unit, of the endoscope. In one embodiment, the probe may be removably attached to a resectoscope via the attachment unit such that a user of the probe can view the electrode assembly, and points distal thereto, from an eyepiece of the resectoscope, wherein the eyepiece is located proximal to the probe proximal end.

In another aspect, the invention provides a method for ablation and/or resection of a target tissue, in which tissue is volumetrically removed via a cool ablation mechanism known as Coblation®, which involves molecular dissociation of tissue components. In one embodiment of the invention, there is provided a method for resecting and harvesting a tissue fragment for tissue analysis, wherein the tissue fragment is removed via electrosurgical ablation at a temperature in the range of about 45° C. to 90° C.

In another aspect, the invention provides a method for transurethral resection of the prostate (e.g., TURP) in which prostate tissue is electrosurgically removed using a probe of the present invention. During such a method, the probe may be manipulated in a plurality of different ways, depending on the condition of the patient and the treatment called for, according to different embodiments of the invention. For example, according to one embodiment, the probe may be manipulated such that the electrode assembly exhibits a gentle brushing motion (e.g., reciprocal motion) with respect to a surface of the target tissue, whereby a relatively thin layer of tissue is vaporized during each stroke. In another embodiment, the electrode assembly may be applied more forcefully against the target tissue in a reciprocating motion, whereby one or more fragments or chips of tissue are electrosurgically resected, typically each proximal stroke of the probe resecting a single fragment of tissue. Tissue fragments removed in this manner may be optionally retrieved for biopsy. In a third embodiment, the probe distal end may be inserted into the target tissue, perhaps to a depth of a few mm., or more, in order to remove one or more tissue fragments to be harvested for biopsy. Of course, all three, or any two, of the modes of manipulating the probe, as outlined above, can be combined in a single procedure. Typically, in each embodiment, the target tissue is ablated (vaporized or resected) via a cool ablation mechanism involving plasma-induced molecular dissociation of tissue components. In another aspect, the invention includes a method for ablation or resection of uterine tissue, such as polyps, leiomyomas, fibroids, and the like, in which the probe distal end is advanced towards the target tissue via the cervix of the uterus, and the target tissue is electrosurgically removed via the cool ablation mechanism (known as Coblation®D) involving molecular dissociation of tissue components to yield low molecular weight (e.g., gaseous) ablation by-products.

A further understanding of the nature and advantages of the invention will become apparent by reference to the remaining portions of the specification and drawings.

BRIEF DESCRIPTION OF THE DRAWINGS

FIG. 3 illustrates an introducing sheath of the resectoscope of FIG. 2;

FIG. 4 illustrates the return electrode oversheath of FIG. 2;

FIG. 5 illustrates a cross-sectional view of the proximal portion of the resectoscope of FIG. 2, illustrating the electrical connection with the return electrode oversheath;

FIG. 6 is a cross-sectional view of a proximal portion of the resectoscope in FIG. 2, illustrating the electrical connection with the resecting loop assembly;

FIG. 7 is a top section view of a proximal portion of the resectoscope;

FIG. 14 is a transverse cross-sectional view of the resecting loop electrode of FIG. 9;

FIGS. 15A and 15B are transverse cross-sectional views of alternative loop electrodes according to the present invention;

FIGS. 16A-16E, 17A, 17B, 18A, 18B, 19, 20A and 20B illustrate alternative electrode configurations according to the present invention;

FIGS. 23A-23E illustrate another embodiment of the resecting loop electrode incorporating two active electrodes;

DESCRIPTION OF THE PREFERRED EMBODIMENTS

Figure 1:
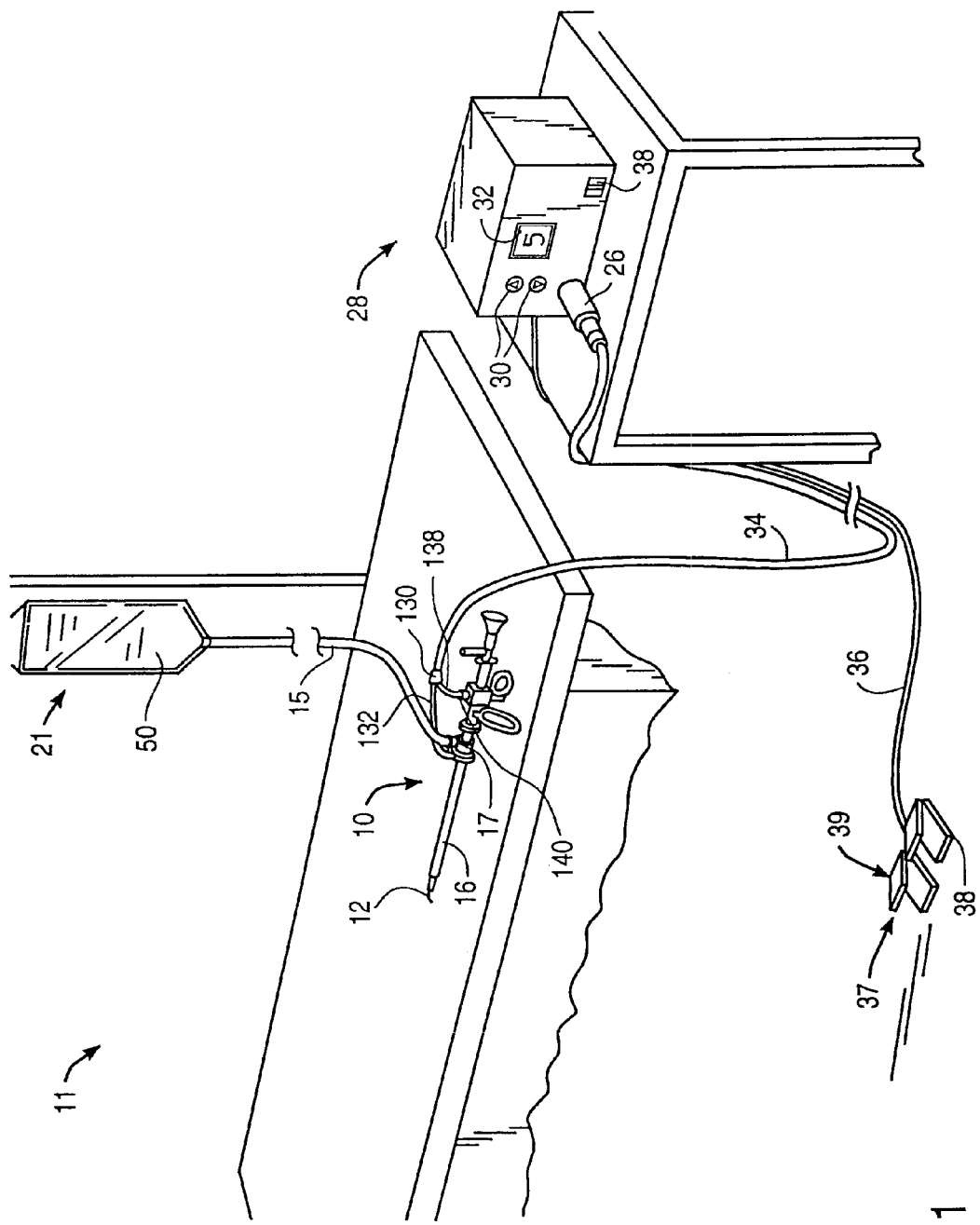
FIG. 1 is a perspective view of a representative electrosurgical system including an electrosurgical resectoscope, an electrically conductive fluid supply and an electrosurgical power supply constructed in accordance with the principles of the present invention.

The present invention provides a system and method for selectively applying electrical energy to a target location within or on a patient's body, such as solid tissue or the like, including procedures within confined spaces such as the spaces around the articular cartilage between the femur and tibia and spaces between adjacent vertebrae in the patient's spine, and procedures that involve resection of relatively larger pieces of tissue. For convenience, the remaining disclosure will be directed primarily to the resection of prostate tissue, and the cutting, shaping or ablation of meniscal tissue located adjacent articular cartilage and soft tissue covering vertebrae. However, it will be appreciated that the system and method can be applied equally well to procedures involving other tissues of the body, as well as to other procedures including open surgery, laparoscopic surgery, thoracoscopic surgery, and other endoscopic surgical procedures. Examples of such procedures include oral procedures, including gingival tissues and mucosal tissues located in the mouth or epidermal tissue on the outer skin, dermatological procedures, such as the treatment of tumors, abnormal tissues, and the like or, canalizing or boring channels or holes through tissue, such as the ventricular wall during transmyocardial revascularization procedures. Other procedures include laminectomy/disketomy procedures for treating herniated disks, decompressive laminectomy for stenosis in the lumbosacral and cervical spine, posterior lumbosacral and cervical spine fusions, treatment of scoliosis associated with vertebral disease, foraminotomies to remove the roof of the intervertebral foramina to relieve nerve root compression and anterior cervical and lumbar diskectomies. The present invention is also useful for resecting tissue within accessible sites of the body that are suitable for electrode loop resection, such as the resection of leiomyomas (fibroids) located within the uterus, as well as prostate tissue, and other diseased or hypertrophied tissue of a patient.

In addition, the present invention is particularly useful in procedures where the tissue site is flooded or submerged with an electrically conducting fluid, such as isotonic saline. Such procedures, e.g., arthroscopic surgery and the like, are described in detail in co-pending PCT International Application, U.S. National Phase Serial No. PCT/US94/05168, filed on May 10, 1994, the complete disclosure of which is incorporated herein by reference.

The electrosurgical probe will comprise a shaft having a proximal end and a distal end which supports one or more active electrode(s). The shaft may assume a wide variety of configurations, with the primary purpose being to mechanically support the active electrode(s) and permit the treating physician to manipulate the electrode(s) from a proximal end of the shaft. Usually, the shaft will be a narrow-diameter rod or tube, more usually having dimensions which permit it to be introduced into a body cavity, such as the arthroscopic cavity, through an associated trocar or cannula in a minimally invasive procedure, such as arthroscopic, laparoscopic, thoracoscopic, and other endoscopic procedures. Thus, the shaft will typically have a length of at least 5 cm for oral procedures and at least 10 cm, more typically being 20 cm, or longer for endoscopic procedures. The shaft will typically have a diameter of at least 1 mm and frequently in the range from 1 to 10 mm. In the case of open surgical procedures or procedures on the external portions of the patient's body (e.g., the skin), the shaft may have any suitable length and diameter that would facilitate handling by the surgeon.

The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode(s). The shaft will usually include a plurality of wires or other conductive elements running axially therethrough to permit connection of the electrode(s) to a connector at the proximal end of the shaft. Specific shaft designs will be described in detail in connection with the figures hereinafter.

The present invention may use a single active electrode or an electrode array distributed over a distal contact surface of a probe. In the case of an electrode array, the array usually includes (but is not limited to) a plurality of independently current-limited and/or power-controlled electrodes to apply electrical energy selectively to the target tissue while limiting the unwanted application of electrical energy to the surrounding tissue and environment resulting from power dissipation into surrounding electrically conductive liquids, such as blood, normal saline, and the like. The electrodes may be independently current-limited by isolating the electrodes from each other and connecting each electrodes to a separate power source that is isolated from the other electrode terminals. Alternatively, the electrodes may be connected to each other at either the proximal or distal ends of the probe to form a single wire that couples to a power source.

In an exemplary embodiment, each individual electrode in the electrode array is electrically insulated from all other electrodes in the array within the probe and is connected to a power source which is isolated from each of the other electrodes in the array or to circuitry which limits or interrupts current flow to the electrode when low resistivity material (e.g., blood or electrically conductive saline irrigant) causes a lower impedance path between the common electrode and the individual electrode terminal. The isolated power sources for each individual electrode may be separate power supply circuits having internal impedance characteristics which limit power to the associated electrode terminal when a low impedance return path is encountered, may be a single power source which is connected to each of the electrodes through independently actuatable switches, or may be provided by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode(s) due to oxide layers which form selected electrode terminals (e.g., titanium or a resistive coating on the surface of metal). A more complete description of a system and method for selectively limiting current to an array of isolated electrode terminals can be found in commonly assigned U.S. Pat. No. 5,697,882, the complete disclosure of which is incorporated herein by reference.

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

In the case of a single electrode, the invention may also use current limiting means to apply electrical energy selectively to the target tissue while limiting the unwanted application of electrical energy to the surrounding tissue. In this embodiment, the electrode may be connected to current limiting elements or to circuitry which limits or interrupts current flow to the electrode when low resistivity material (e.g., blood or electrically conductive saline irrigant) causes a lower impedance path between the common electrode and the electrode. The current limiting elements or circuitry may be configured to completely interrupt or modulate current flow to the electrode, for example, when a certain percentage of the electrode surface is in contact with low resistivity material. In one embodiment, the current flow will be modulated or completely interrupted when, for example, a large portion of the electrode surface is exposed to fluids and, therefore, not in contact with the target tissue. In this manner, current can be selectively applied to the target tissue, while minimizing current flow to surrounding fluids and adjacent non-target tissue structures.

According to the present invention, the active electrode(s) will have an active portion or surface with surface geometries shaped to promote high electric field intensity and associated high current density along the leading edges of the active electrode(s). Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be removed along the length of a round wire or hollow, cylindrical wire to form D or C shaped electrodes, respectively, with edges facing in the cutting direction. Alternatively, material can be removed at closely spaced intervals along the length of the electrode to form transverse grooves, slots, holes, threads or the like along the electrode.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0, or by using a high velocity stream of abrasive particles (e.g., grit blasting) to create asperities on the surface of an elongated electrode.

Additionally or alternatively, the active electrode surface(s) may be provided by assembling alternating layers of electrically conductive members (i.e., electrodes) and electrically insulating spacers. By way of example, an active electrode having multiple circular edges may be constructed using alternating layers of concentric, thin metal washers (e.g., titanium, stainless steel or the like), having outside diameters D. The washers may be separated by thin concentric insulating spacers (e.g., anodized aluminum, silicone rubber, ceramic, glass, glass ceramic, plastic, etc.) having an outside diameter D' which is less than D so that the edges of the metal washers extend beyond the insulating spacers. The electrode assembly can be constructed by placing the metal washers over a central, electrically conductive mandrel, which provides for electrical communication between the power source and the multiple metal "washer" shaped electrodes. In this arrangement, the electrodes are preferably at the same source polarity since they are in contact with a common electrical lead (i.e., mandrel).

Alternatively, the electrode assembly may include a split mandrel having opposite polarities such that adjacent metal washers are at opposite polarities to effect one or more pairs of bipolar washer shaped electrodes. In this configuration, the metal electrodes may have any shape suitable for the intended ablation or resection of tissue, e.g., square, circular, hexagonal, octagonal, triangular, etc. In addition, the perimeter of the thin metal electrode may be stamped, machined, notched or otherwise modified to increase the electric field intensity at the working (outer) surface of the metal electrode. Also, the metal electrodes (e.g., metal washers) may be coated with an electrically insulating layer (e.g., silicone rubber, ceramic, glass or porcelain) of sufficient thickness to provide spacing between adjacent electrode members, whether the electrode assembly is monopolar or bipolar. The insulating coating may extend up to the perimeter of the metal electrode (e.g., washer), or it may be recessed from the perimeter to expose a greater portion of the edges of the electrodes.

In another aspect of the invention, the active electrodes will also have a "non-active" portion or surface(s) to selectively reduce undesirable current flow from the non-active portion or surface(s) into tissue or surrounding electrically conductive fluids (e.g., isotonic saline, blood or blood/non-conducting irrigant mixtures). The "non-active" electrode surface(s) may be coated with an electrically insulating material, such as silicone elastomer. This can be accomplished, for example, with plasma deposited coatings of an insulating material, thin-film deposition of an insulating material (e.g., SiO2 or Si3N4) using evaporative or sputtering techniques, dip coating or by providing an electrically insulating support member to electrically insulate a portion of the external surface of the electrode.

The method of the present invention comprises positioning an electrosurgical probe adjacent the target tissue so that at least one active electrode is brought into at least close proximity to the target site. A return electrode is positioned within an electrically conductive fluid, such as isotonic saline, to generate a current flow path between the target site and the return electrode. High frequency voltage is then applied between the active and return electrodes through the current flow path created by the electrically conductive fluid in either a bipolar or monopolar manner. The probe may then be translated, reciprocated or otherwise manipulated to cut the tissue or effect the desired depth of ablation.

The current flow path may be generated by submerging the tissue site in an electrically conductive fluid (e.g., during arthroscopic surgery and the like), or by directing an electrically conductive fluid along a fluid path past the return electrode and to the target site to generate the current flow path between the target site and the return electrode. This latter method is particularly effective in a dry environment (i.e., the tissue is not submerged in fluid), such as open, endoscopic or oral surgery, because the electrically conductive fluid provides a suitable current flow path from the target site to the return electrode. A more complete description of an exemplary method of directing electrically conducting fluid between the active and return electrodes is described in commonly assigned U.S. Pat. No. 5,697,281, the contents of which are incorporated herein by reference. In one embodiment, the active electrode(s) are disposed at the distal end of the probe and the return electrode is spaced from the active electrode and enclosed within an insulating sheath. This arrangement minimizes exposure of the return electrode to surrounding tissue and minimizes possible shorting of the current between the active and return electrodes. In endoscopic procedures, the probe may be passed through a cannula while viewing of the operative site is provided through the use of an endoscope disposed in a separate cannula. Alternatively, the probe may be attached to, or integral with, an endoscope.

In the method of the present invention, a high frequency voltage is applied between the active portion of the active electrode(s) and the return electrode to develop high electric field intensities in the vicinity of the target tissue. The high electric field intensities lead to electric field induced molecular breakdown of target tissue through molecular dissociation (rather than thermal evaporation or carbonization of tissue). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of water from within the cells of the tissue, as is typically the case with electrosurgical desiccation.

The high electric field intensities may be generated by applying a high frequency voltage that is sufficient to vaporize the electrically conductive fluid over at least a portion of the active electrode(s) in the region between the distal tip of the active electrode and the target tissue. Since the vapor layer or vaporized region has a relatively high electrical impedance, it minimizes current flow into the electrically conductive fluid. This ionization, under the conditions described herein, induces the discharge of energetic electrons and photons from the vapor layer and to the surface of the target tissue. A more detailed description of this phenomenon can be found in commonly assigned U.S. Pat. No. 5,697,882 the complete disclosure of which is incorporated herein by reference.

The voltage applied between the return electrode and the active electrode(s) will be at high or radio frequency, typically between about 5 kHz and 20 MHz, usually being between about 30 kHz and 2.5 MHz, and more typically being between about 50 kHz and 400 kHz. The RMS (root mean square) voltage applied will usually be in the range from about 5 volts to 1000 volts, typically being in the range from about 50 volts to 800 volts, and more typically being in the range from about 100 volts to 400 volts. These frequencies and voltages will result in peak-to-peak voltages and currents that are sufficient to vaporize the electrically conductive fluid and, in turn, sufficient to create the conditions within the vaporized region which result in high electric fields to ablate tissue. According to one aspect of the invention, the vaporized electrically conductive fluid is in the form of a plasma. Typically, the peak-to-peak voltage will be in the range of from about 200 to 2000 volts, usually in the range of 300 to 1600 volts, and more typically in the range of 500 to 1200 volts.

A preferred power source of the present invention delivers a high frequency voltage selectable to generate average power levels ranging from tens of milliwatts to tens of watts up to hundreds of watts per electrode, depending on the number of electrodes, the target tissue being ablated, the rate of ablation desired or the maximum allowed temperature selected for the probe tip. Typically, during ablation processes performed according to the instant invention, the target tissue is exposed to a temperature in the range of from about 45° C. to 90° C., and more typically from about 60° C. to 75° C. The power source allows the user to select the voltage level according to the specific requirements of a particular open surgery, oral surgery, dermatological procedure, percutaneous, endoscopic, or other surgical procedure.

The power source may be current limited or otherwise controlled so that undesired heating of electrically conductive fluids or other low electrical resistance media does not occur. In one embodiment, current limiting inductors are placed in series with each independent electrode terminal, where the inductance of the inductor is in the range of 10 uH to 50,000 uH, depending on the geometry and size of the electrode(s), the electrical properties of the target tissue, the desired ablation rate and the operating frequency. Alternatively, capacitor-inductor (LC) circuit structures may be employed, as described previously in co-pending PCT application No. PCT/US94/05168, the complete disclosure of which is incorporated herein by reference. Additionally, current-limiting resistors may be selected. Preferably, these resistors will have a large positive temperature coefficient of resistance so that, as the current level begins to rise for any individual electrode in contact with a low resistance medium (e.g., saline irrigant), the resistance of the current limiting resistor increases significantly, thereby minimizing the power delivery from the electrode into the low resistance medium (e.g., saline irrigant).

As an alternative to such passive circuit structures, regulated current flow to each electrode terminal may be provided by a multi-channel power supply. A substantially constant current level for each individual electrode terminal within a range which will limit power delivery through a low resistance path, e.g., isotonic saline irrigant, and would be selected by the user to achieve the desired rate of cutting or ablation. Such a multi-channel power supply thus provides a substantially constant current source with selectable current level in series with each electrode terminal, wherein all electrodes will operate at or below the same, user selectable maximum current level. Current flow to all electrode terminals could be periodically sensed and stopped if the temperature measured at the surface of the electrode array exceeds user-selected limits. Particular control system designs for implementing this strategy are well within the skill of the art.

Yet another alternative embodiment involves the use of a power supply for energizing one or more electrodes having use of one or more channels of user-selectable voltage levels. The channels would incorporate an active control mechanism for limiting current levels below a pre-selected maximum level. The pre-selected maximum current level depends on the size and configuration of the electrode(s), and may be "factory" set or user selectable. Alternatively, an indicator device may be included in the probe (e.g., a resistor having a resistance value which corresponds to the maximum current level appropriate to a specific electrode configuration) such that the power supply can (1) first measure the indicator device value (e.g., measure the resistance of the indicator) contained within the probe; and (2) then set the maximum current level which corresponds to that resistance value. In this manner, a range of probe designs having greatly differing electrode size(s) and configuration(s) can be energized since the power supply will automatically adjust the maximum current level to correspond to each particular electrode size and configuration.

Yet another alternative involves the use of one or several power supplies which allow one or several electrodes to be simultaneously energized and which include active control means for limiting current levels below a preselected maximum level. In this arrangement, only one or several electrodes would be simultaneously energized for a brief period. Switching means would allow the next one or several electrodes to be energized for a brief period. By sequentially energizing one or several electrodes, the interaction between adjacent electrodes can be minimized (for the case of energizing several electrodes positioned at the maximum possible spacing within the overall envelope of the electrode array) or eliminated (for the case of energizing only a single electrode at any one time). As before, a resistance measurement means or device may be employed for each electrode prior to the application of power wherein a (measured) low resistance (below some preselected level) will prevent that electrode from being energized during a given cycle. By way of example, the sequential powering and control scheme of the present invention would function in a manner similar to an automobile distributor. In this example, an electrical contact rotates past terminals connected to each spark plug. In this example, each spark plug corresponds to the exposed surface of each of the electrodes. In addition, the present invention includes the means to measure the resistance of the medium in contact with each electrode and cause voltage to be applied only if the resistance exceeds a preselected level.

During the surgical procedure, the distal end of the probe or the active electrode(s) may be maintained at a small distance away from the target tissue surface. This small spacing allows for the continual resupply of electrically conductive fluid into the interface between the active electrode(s) and the target tissue surface. This continual resupply of the electrically conductive fluid helps to ensure that the thin vapor layer will remain between the active electrode(s) and the tissue surface. In addition, dynamic movement of the active electrode(s) over the tissue site allows the electrically conductive fluid to cool the tissue surrounding recently ablated areas to minimize thermal damage to this surrounding tissue. In one embodiment, the active electrode(s) may be spaced about 0.02 to 2 mm from the target tissue, and typically about 0.05 to 0.5 mm from the target tissue, during the ablation process. One method of maintaining this space is to translate and/or rotate the probe transversely relative to the tissue, i.e., using a light brushing motion, to maintain a thin vaporized layer or region between the active electrode and the tissue. Of course, for aggressive ablation of tissue, or for removal of a tissue fragment for biopsy, the probe may be advanced axially so that the active electrode(s) penetrate the target tissue to a suitable depth. Similarly, if coagulation of a deeper region of tissue is necessary (e.g., for sealing a bleeding vessel imbedded within the tissue), it may be desirable to press the active electrode(s) against the tissue to effect joulean heating therein.

In one embodiment of the invention, the active electrode or the electrode array will have an exposed length in the range from about 2.5 to 12.5 mm. With electrode lengths within this range, applicant has found that current-limiting inductors having inductance values of about 0 to 100 uH, preferably about 25 to 50 uH, are suitable for establishing the requisite conditions for selective ablation described above (i.e., the generation of sufficient electric field intensities to form a vapor layer in the electrically conductive fluid and to induce the discharge of energy through the vapor layer to ablate tissue while precisely controlling the extent of ablation and minimizing damage to non-target tissue. Of course, the active electrode(s) may have a substantially smaller exposed length away from the probe than described above (on the order of about 0 to 0.5 mm). This configuration is described in commonly assigned U.S. Pat. No. 5,697,882, the complete disclosure of which is incorporated herein by reference.

Referring to the drawings in detail, wherein like numerals indicate like elements, an electrosurgical system 11 is shown constructed according to the principles of the present invention. Referring to FIG. 1, electrosurgical system 11 generally comprises an electrosurgical resectoscope 10 incorporating a resecting loop assembly 12 with an active electrode (not shown in FIG. 1), and a return electrode oversheath 16 circumscribing a portion of the resecting loop assembly 12. The resectoscope 10 is connected to a power supply 28 for providing high frequency voltage to the active electrode and a liquid source 21 for supplying electrically conducting fluid 50 to a target tissue (see FIGS. 21 and 22). A liquid supply tube 15 removably couples liquid source 21, (e.g., a bag of fluid elevated above the surgical site or having a pumping device), with return electrode oversheath 16. A manual control valve 17 may also be provided between the proximal end of return electrode oversheath 16 and supply tube 15 to allow the surgical team to regulate the flow of electrically conductive fluid 50.

Figure 2:
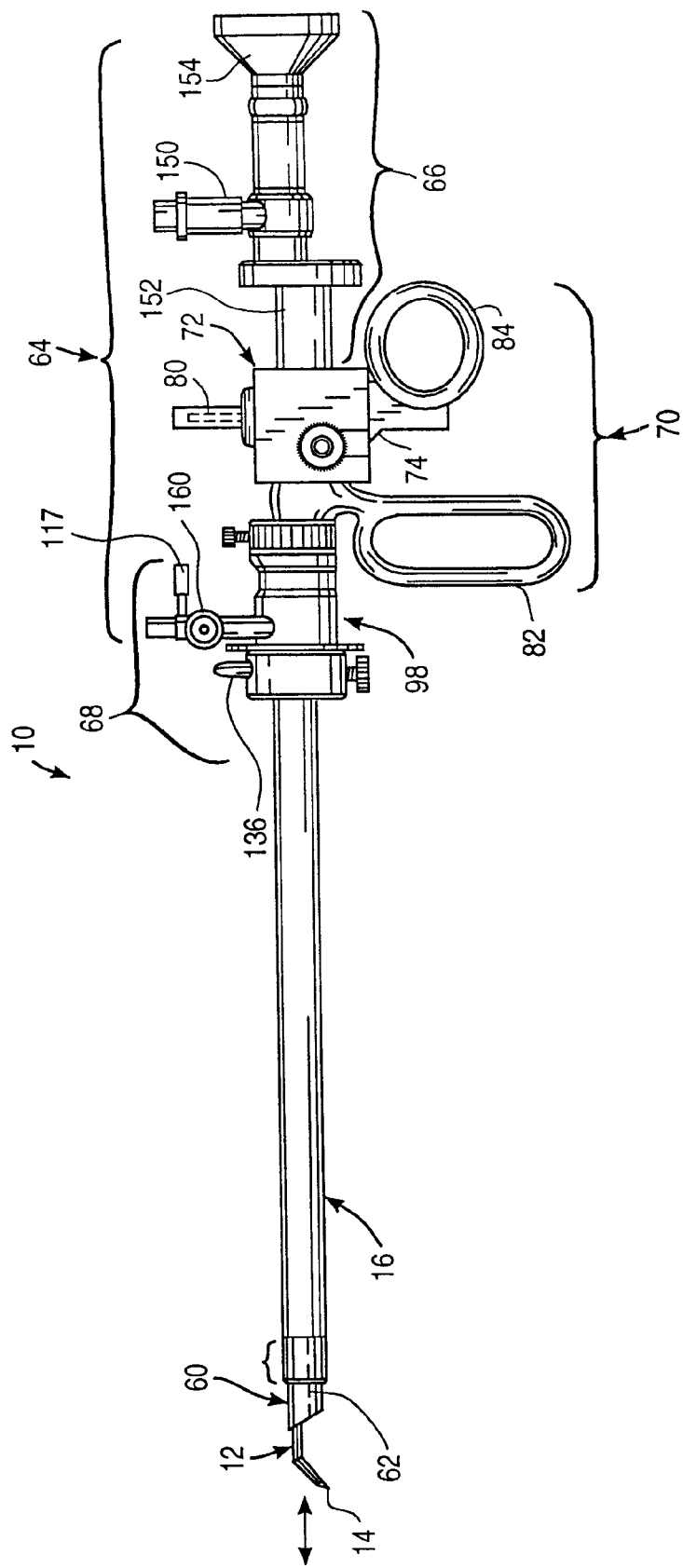
FIG. 2 is an enlarged perspective view of the resectoscope of FIG. 1 incorporating a return electrode oversheath and a resecting loop assembly according to the present invention.

Power supply 28 has a selector 30 for varying the applied voltage level. Power supply 28 also includes a mechanism for energizing the active electrode of resectoscope 10 through the depression of a first pedal 39 in a foot pedal 37 positioned close to the user. The foot pedal 37 will usually include a second pedal 38 for remotely adjusting the energy level applied to active electrode 14 (FIG. 2). In an exemplary configuration, first pedal 39 will apply a higher voltage level suitable for cutting and ablating tissue, and second pedal 38 will apply a lower voltage level suitable for coagulating and sealing tissue, such as a transected blood vessel (discussed in further detail below). A specific design of one power supply which may be used with the electrosurgical probe of the present invention is described in parent application PCT U.S. 94/051168, the full disclosure of which has previously been incorporated herein by reference.

Referring to FIGS. 2-11, resectoscope 10 represents a conventional or specialized resectoscope that is adapted for use with resecting loop assembly 12 and return electrode oversheath 16, according to the present invention. Existing resectoscopes useful with the present invention can be found, for example, under the trade names of USA Elite System Resectoscope from Circon/ACMI of Stamford, Conn. and OES Resectoscope from Olympus Corporation of Lake Success, N.Y. Loop assembly 12 and oversheath 16 may also be used without a resectoscope. In this configuration, the surgeon may use other means for viewing the surgical site, such as a separate endoscope. Resectoscope 10 generally includes a proximal handle 64, and an introducing sheath 60 (FIG. 3) having a hollow, tubular shaft 62 for axially receiving loop assembly 12. Sheath 60 also includes a proximal hub 98 for connecting sheath 60 to handle 64 and return electrode oversheath 16 (discussed in detail below). As shown in FIG. 2, handle 64 includes a viewing assembly 66, an irrigant/suction assembly 68 and an actuation assembly 70 for axially reciprocating loop assembly 12 relative to shaft 62.

Referring to FIGS. 2, 6 and 7, actuation assembly 70 includes a coupling housing 72 having an outer knob or thumbscrew 74 that can be tightened to secure a proximal connector leg 76 of loop assembly 12 to an electrically conducting inner sleeve member 78 of coupling housing 72 (FIG. 7). Sleeve member 78 electrically couples leg 76 to a resecting loop terminal 80 (FIG. 6), which can be removably coupled to power supply 28 to provide power to loop assembly 12 (discussed in further detail below). Coupling housing 72 is axially translatable relative to introducing sheath 60 so that resecting loop assembly 12 can be axially translated relative to the distal end 94 of tubular shaft 62 (see FIG. 3). As shown in FIG. 2, resectoscope 10 will usually include a finger loop 82 and a thumb loop 84 suitably connected to housing 72 for reciprocating housing 72 and loop assembly 12 relative to the distal end 94 of shaft 62. Of course, it will be recognized that other control means for axially reciprocating loop assembly 12 can be utilized with the present invention, such as rotatable knobs, trigger buttons, and the like.

Referring to FIGS. 4 and 5, electrosurgical system 11 will preferably include a return electrode oversheath 16 for completing the current path between active electrode 14 and power supply 28 (discussed in detail below). It should be made clear, however, that the present invention is not limited to a bipolar modality and, may utilize a monopolar mode. In this configuration, return electrode oversheath 16 is not required. Instead, voltage is applied between an active electrode 14 and a dispersive electrode plate externally attached to the patient's skin such that electric current flows from active electrode 14, through the patient's body, to the dispersive electrode.

Return electrode over sheath 16 generally includes an electrically conducting, hollow shaft 86 coupled to a proximal housing 88 with a suitable epoxy adhesive, for example. The inner and outer surfaces of shaft 86 are covered with an electrically insulating layer 90 over the entire length of shaft 86 except for an exposed portion 92 at the shaft distal end, which remains exposed to provide a current path from active loop assembly 12 (discussed below). Electrically insulating layer 90 may comprise a heat shrinkable tubing material, such as Kynar™, or it may be a deposited coating, such as Parylene™, polytetrafluoroethylene, polyimide, flourinated ethylene-propylene or the like. The provision of the electrically insulating layer 90 over return electrode shaft 86 prevents direct electrical contact between the return electrode and any adjacent body structure or the surgeon. Such direct electrical contact between a body structure (e.g., tendon) and an exposed return electrode member could result in unwanted heating of the structure at the point of contact causing necrosis. If return electrode oversheath 16 is being used with an electrically insulating resectoscope sheath (e.g., a plastic tubular sheath), the inner surface of shaft 86 may remain exposed (i.e., electrically insulating layer 90 may be omitted).

Figure 21:
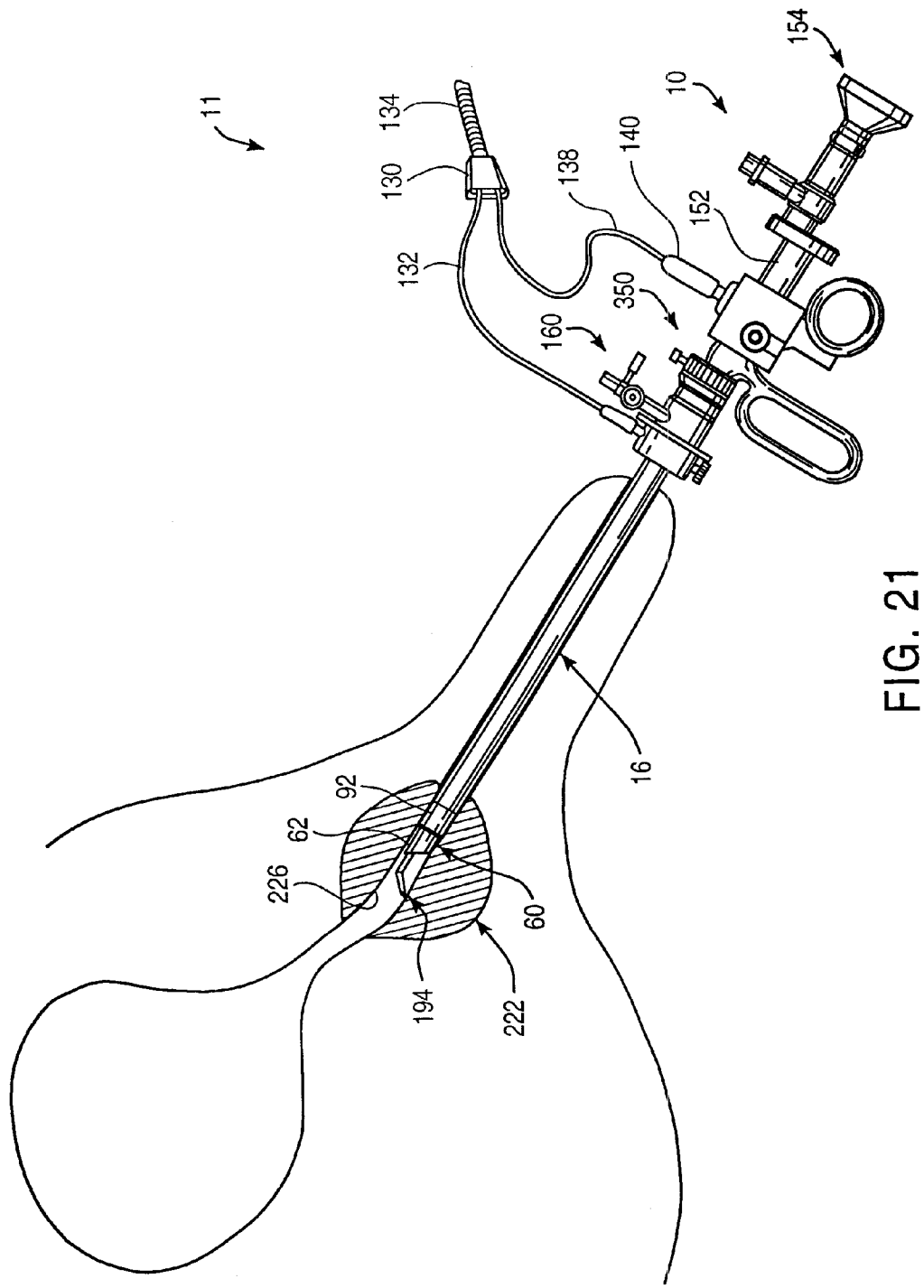
FIG. 21 illustrates a method of transurethral resection of prostate tissue with the electrosurgical system of FIG. 1.

Return electrode shaft 86 will have an inner diameter large enough to slide shaft 86 over tubular shaft 62 of introducing sheath 60 (FIG. 5). Distal end portion 94 of shaft 62 is introduced through an opening 96 in proximal housing 88 and axially delivered through return electrode shaft 86 until housing 88 abuts against proximal hub 98 of introducing sheath 60. Return electrode oversheath 16 further includes a fastener, such as a thumbscrew 100, to secure return electrode oversheath 16 to introducing sheath 60. As shown in FIG. 5, return electrode shaft 86 has an opening 102 aligned with thumbscrew 100 so that the thumbscrew 100 can engage tubular shaft 62 of introducing sheath 60. Thumbscrew 100 preferably comprises an electrically insulating material, such as Ultem™, to minimize electrical shock to the surgeon during use of resectoscope 10. Referring to FIGS. 1 and 5, resectoscope 10 is electrically connected to power supply 28 with cable 34, which is removably connected to power supply 28 by a power supply connector plug 26. Cable 34 includes an adaptor 130 that branches into a first lead 132 which is removably connected via plug 134 to a return electrode terminal 136, e.g., via a minibananna plug, and a second lead 138 which is removably connected via plug 140 to resecting loop terminal 80 (FIGS. 6, 21). As shown in FIG. 5, return electrode plug 134 includes a recessed electrical receptacle 142 which permits plug 134 to be inserted into a cavity 144 of return electrode housing 88. This provides a fluid-tight seal between housing 88 and plug 134 to minimize the possibility of electrical shock to the surgeon or patient if the controller is energized prior to the complete connection of plug 134 and electrode terminal 136.

As mentioned above, handle 64 of resectoscope 10 will also usually include a viewing assembly 66 and an irrigant/suction assembly 68. As shown in FIG. 2, viewing assembly 66 includes a hub 150, a telescopic lumen 152 extending through shaft 62 of introducing sheath 60 and an eyepiece 154 coupled to lumen 152 to permit viewing of the target site by the physician. Alternatively, a camera (not shown) may be attached to the proximal end of hub 150 to allow display of the surgical site on a video monitor. A fiberoptic light source (not shown) is typically attached to hub 150 to illuminate the target site. Irrigant/suction assembly 68 includes proximal hub 98 of introducing sheath 60, and a connector 160 extending from hub 98 and coupled to supply line 15 for introducing a sterile irrigant, typically isotonic saline, to the surgical site. Connector 160 is fluidly coupled to an axial lumen 162 within shaft 62 (see FIG. 3). Fluid may also be withdrawn through axial lumen 162 or a second lumen (not shown) within shaft 62 to withdraw unwanted or excess fluids from the surgical site and to facilitate the surgeon's view.

Referring to FIGS. 8-11, an exemplary resecting loop assembly 12 according to the present invention will now be described. Loop assembly 12 generally includes an electrically insulating hollow shaft 180 with proximal connection leg 76 and a distal active electrode assembly 182. Active electrode assembly 182 includes a bifurcated support member 184 having a pair of hollow arms 186, 188 extending from a distal end 190 of shaft 180. A hollow, electrically insulating tubular member 192 extends from each arm 186, 188 of bifurcated support member 184, and a tubular resecting loop electrode 194 extends from each tubular member 192. Tubular members 192 will comprise a suitable insulating material (e.g., a silicone rubber, ceramic or glass material, such as alumina, zirconia and the like). Such support materials have one or more of the following characteristics: good electrically insulating properties, high flexural modulus, resistance to carbon tracking, biocompatibility, and high melting point.

Figure 8A:
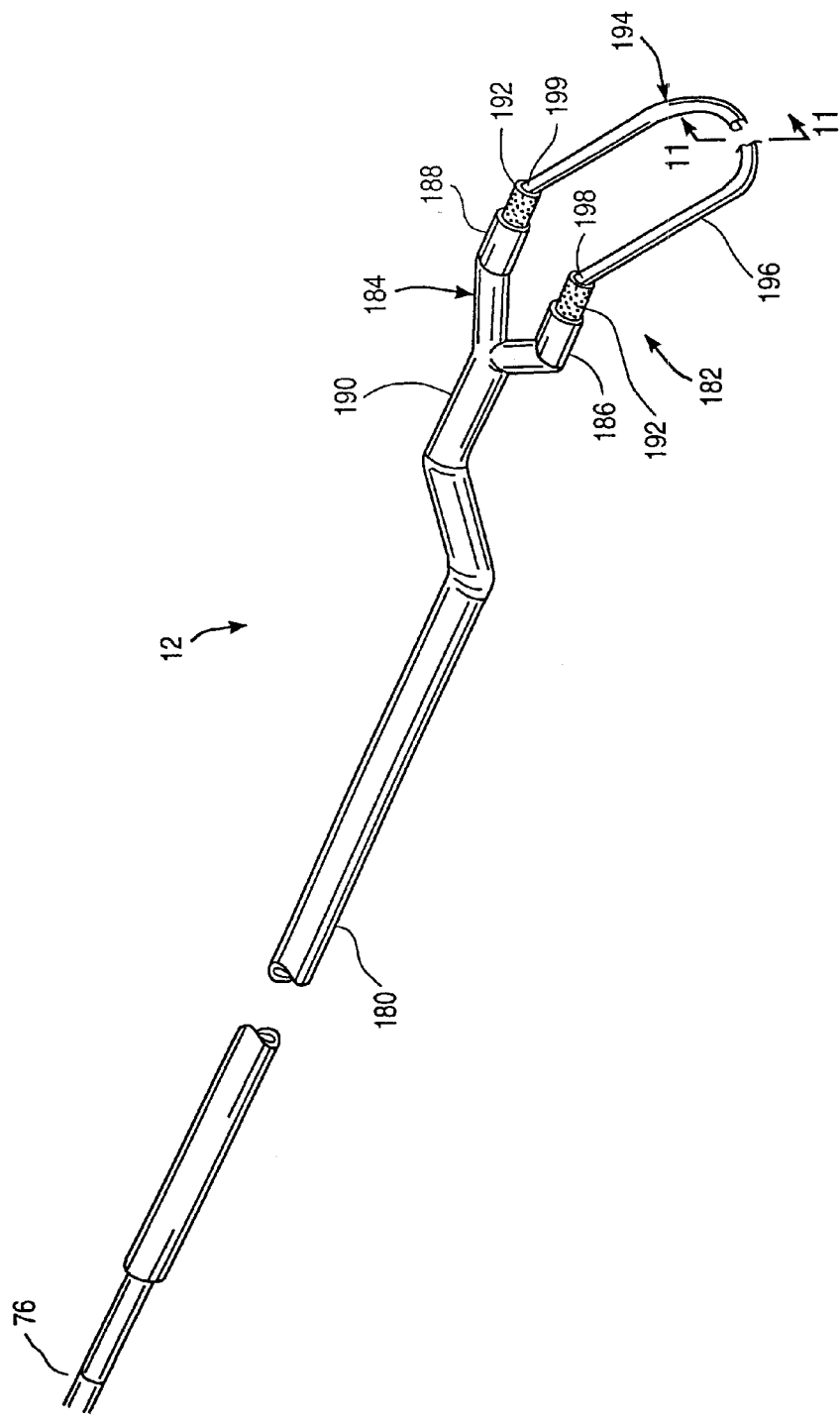
FIG. 8A illustrates the resecting loop assembly of FIG. 2.
Figure 8B:
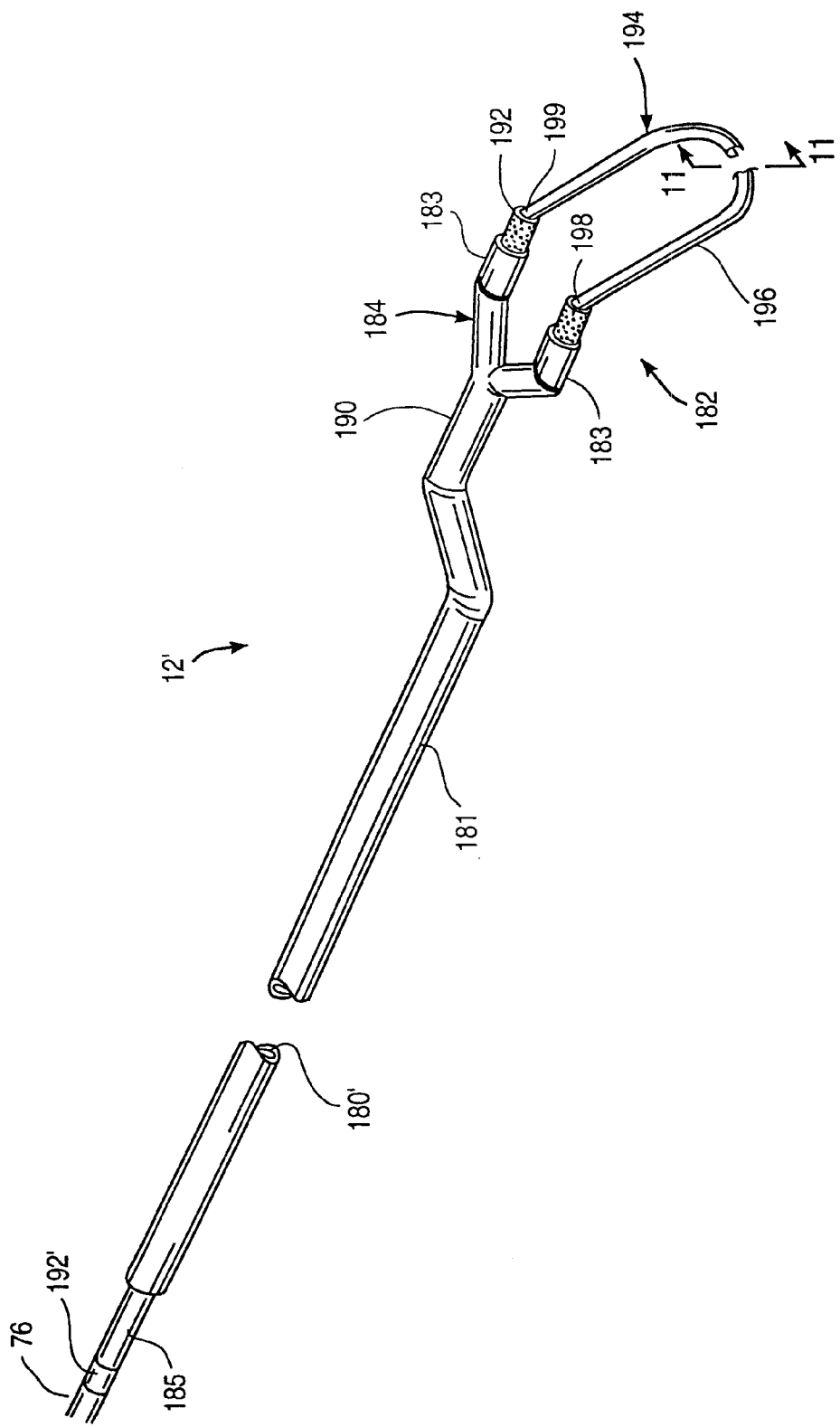
FIG. 8B illustrates an alternative resecting loop assembly incorporating a return electrode.

Alternatively, a resecting loop assembly 12' may incorporate the return electrode so that only a single instrument is required for bipolar resection of tissue (i.e., a return electrode oversheath is not required). By way of example (see FIG. 8B), resecting loop assembly 12' according to the present invention includes an electrically conducting shaft 180' covered with an outer electrically insulating layer 181. Shaft 180' includes a distal exposed portion 183 for completing the current return path with active electrode assembly 182, and a proximal exposed portion 185 for connecting return electrode 180 to power supply 28. An electrically insulating tubular member 192 insulates shaft 180' from resecting loop electrode 194 and exposed portion 185 from proximal connection leg 76. As shown in FIGS. 8A, 8B, and 10A, resecting loop electrode 194 comprises an elongate loop body 196 having first and second ends 198, 199 coupled to and extending within tubular members 192. Resecting loop electrode 194 is preferably composed of a corrosion resistant, electrically conductive metal or alloy, such as platinum, titanium, tantalum, tungsten, stainless steel, nickel and cobalt-based alloys and the like. It should be understood that loop electrode 194 may have configurations other than that described above and shown in FIGS. 8A-11. Preferred requirements for electrode 194 are that: (1) the electrode fits within the available space within the working end of a resectoscope, which generally includes fiber optic or "glass rod" optical viewing and lighting means, articulating resecting means and irrigant supply ports; (2) the electrode is shaped and sized to allow the surgeon to view the tissue site; and (3) the electrode is configured to cut chips or small portions of tissue from the target site. Thus, the "loop" electrode may have a variety of shapes, such as semi-circular, square, triangular, rectangular, or multi-sided geometry (see FIGS. 10B-10D, for example). A semi-circular or U-shaped loop electrode (e.g., FIG. 10A) has the advantage that it easily fits within the cylindrical bore of conventional resectoscopes. In addition, this shape tends to facilitate good visibility for the surgeon, and it produces rapid resection of tissue.

Loop electrode 194 may also comprise a plurality of active electrodes that are either coupled together or electrically isolated from each other (discussed below). In the latter case, electrosurgical system 11 may include current limiting elements or circuitry to independently limit current to the electrodes based on the impedance between each active electrode and the return electrode, as described above.

Figure 9:
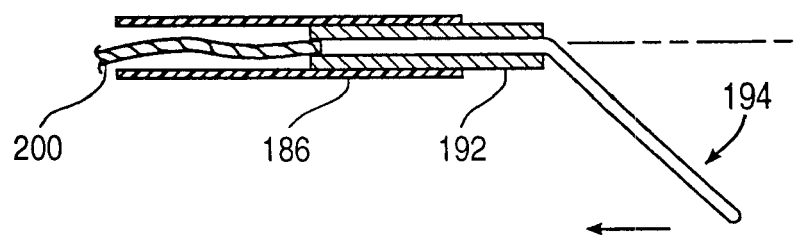
FIG. 9 is a section of a distal portion of the resecting loop assembly of FIG. 5, illustrating a resecting loop electrode.
Figure 10A:
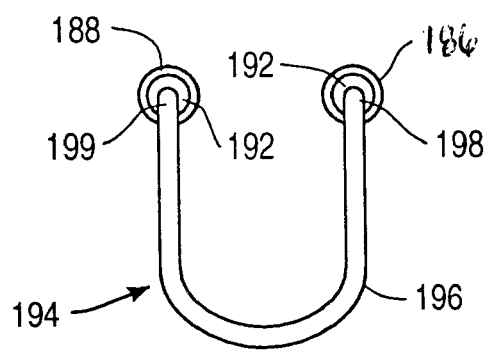
FIG. 10A is a front view of the resecting loop electrode.

Referring to FIGS. 8A and 9, electrical connections 200, such as lead wires, metal tubes or the like, extend through one or both arms 186, 188 of support member 184 and shaft 180 to electrically couple one or both ends 198, 199 of resecting loop electrode 194 with connector leg 76. Electrical connections 200 are coupled to loop electrode 194 and connector leg 74 using crimping, soldering, welding or other suitable methods. Electrical connections 200 are preferably covered with an insulating sheath (not shown) except for exposed distal and proximal portions of connections 200 that are coupled to loop electrode 194 and leg 74, respectively.

Figure 11:
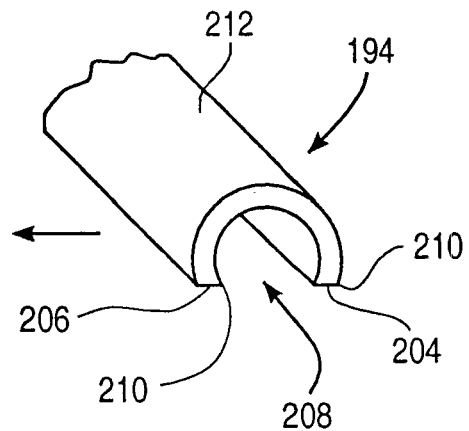
FIG. 11 is an enlarged view of a resecting loop electrode.
Figure 10B:
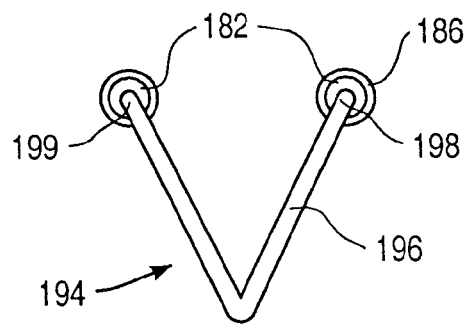
FIGS. 10B-10D illustrate alternative geometries for the resecting loop electrode.
Figure 10C:
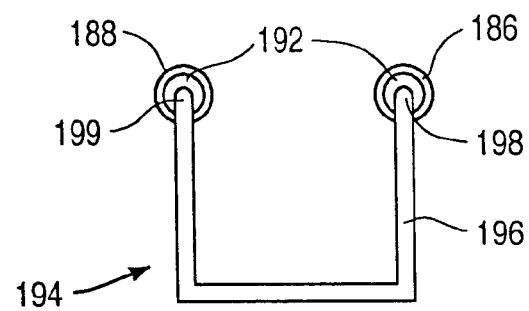
Figure 10D:
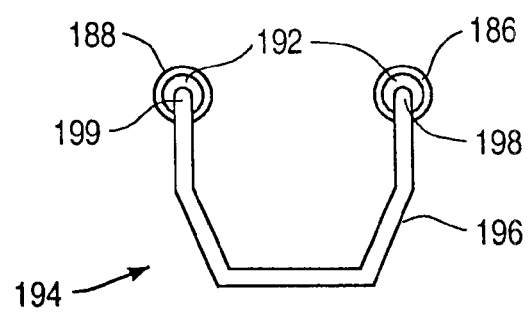

As shown in FIG. 11, according to one embodiment, resecting loop electrode 194 preferably has a substantially C-shaped transverse cross-section along its entire length to form first and second ends 204, 206 that define a slot 208 therebetween. Ends 204, 206 each define relatively sharp edges 210 that promote high electric field intensities around ends 204, 206 to enhance the tissue cutting capabilities of resecting loop assembly 12. Ends 204, 206 and edges 210 of loop electrode 194 form an active portion of electrode that promotes sufficiently high electric field intensities sufficient to reach the threshold conditions for formation of a vapor layer in the electrically conductive liquid, as discussed above. For surgical procedures involving tissue resection, resecting loop electrode 194 is preferably oriented so that ends 204, 206 are generally parallel to the cutting direction (i.e., facing the target tissue, see FIG. 12). This orientation facilitates the formation of a vapor layer between ends 204, 206 and the target tissue and directs the energy induced from the vapor layer to the target tissue.

Figure 12:
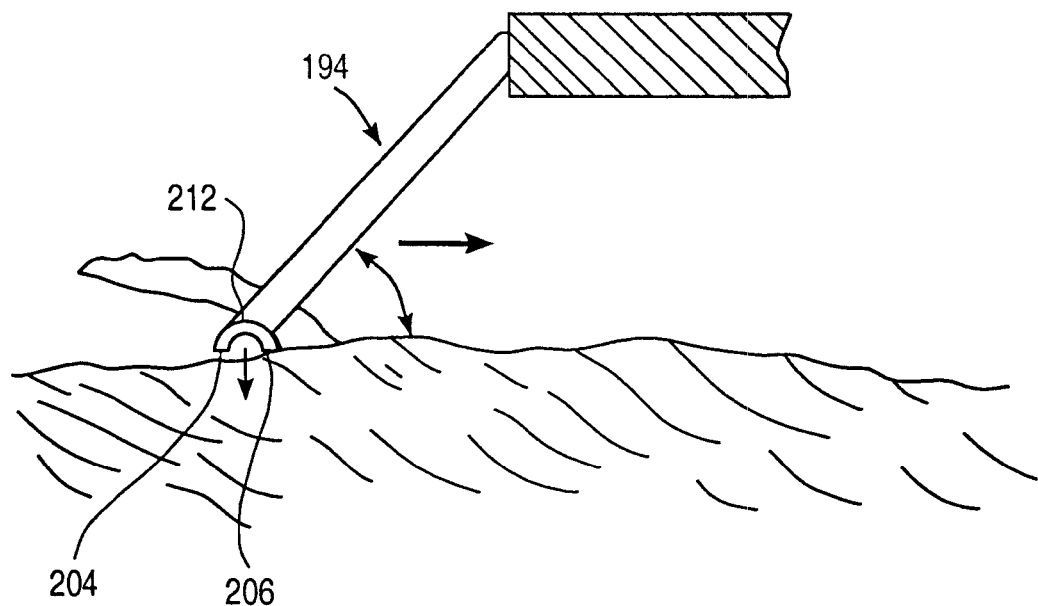
FIG. 12 is a schematic view illustrating the resecting loop electrode of FIG. 9 resecting a tissue portion at a target site.

As shown in FIGS. 11 and 12, loop electrode 194 further includes a non-active portion 212 on the opposite side from ends 204, 206. Non-active portion 212 preferably defines a relatively smooth surface to reduce the electric field intensities around portion 212, thereby minimizing undesirable current flow into fluids and surrounding tissue. In addition, non-active portion 212 may include an insulating layer (not shown) to further minimize the possibility of undesirable tissue damage. This configuration allows the surgeon to more selectively ablate tissue at the target site.

In an exemplary configuration, loop electrode 194 is formed from a hollow tube that is filed or ground down to form a semi-circular, U-shaped or C-shaped transverse cross-section. The filing operation creates four relatively sharp corners 210 along the length of the bipolar loop electrode 194, as shown in FIG. 11. In order to maximize the spacing between the inner electrode edges 210 while maintaining the strength of loop electrode 194, the thin metal wall tubing is filed or ground up to, but not exceeding the diametral line of the tubing. Usually, loop electrode 194 will have an outside diameter of about 0.005 to 0.03 inch and a wall thickness of about 0.003 to 0.01 inch. In a representative embodiment, the resecting or active loop electrode comprises a 0.013 diameter molybdenum wire loop and the return electrode comprises a 0.020 molybdenum wire loop (see embodiments below).

FIGS. 15A and 15B illustrate alternative embodiments of bipolar loop electrode 194. As shown in FIG. 15A, loop electrode 194 may have a D-shaped cross-section having a substantially planar active surface 300. In this embodiment, electrode 194 is preferably fabricated from a solid round wire that is shaped (e.g., ground or filed), substantially as described above for the D-shaped electrode configuration, to form electrode edges 210. As shown in FIG. 15B, electrode 194 may also have a double slotted configuration that is generally formed by grinding both sides of a hollow tube. Alternatively, loop electrode 194 may be constructed from a formed wire (e.g., a round wire that has been drawn through a shaping die) shaped to create corners on the periphery of the extended loop electrode surface. FIGS. 16A-16E illustrate examples of electrode cross-sectional shapes that may be used with the present invention.

Figure 17A:
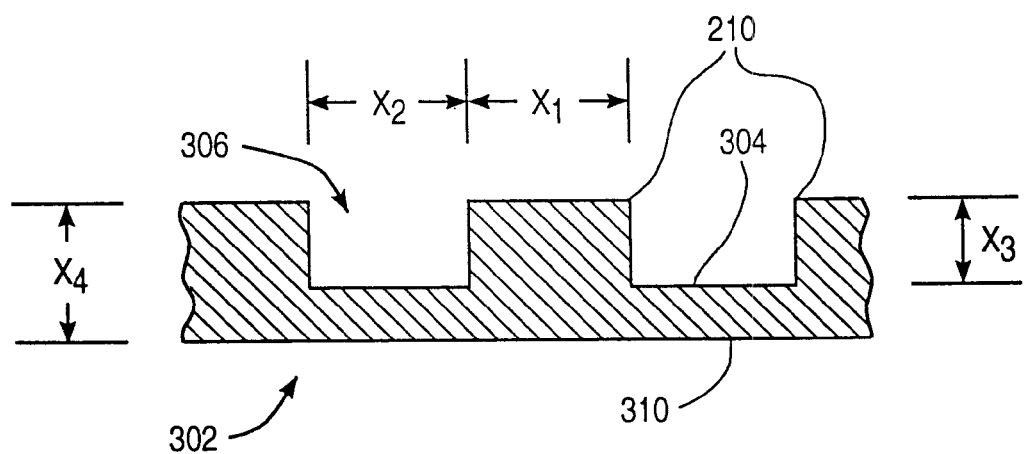
Figure 17B:
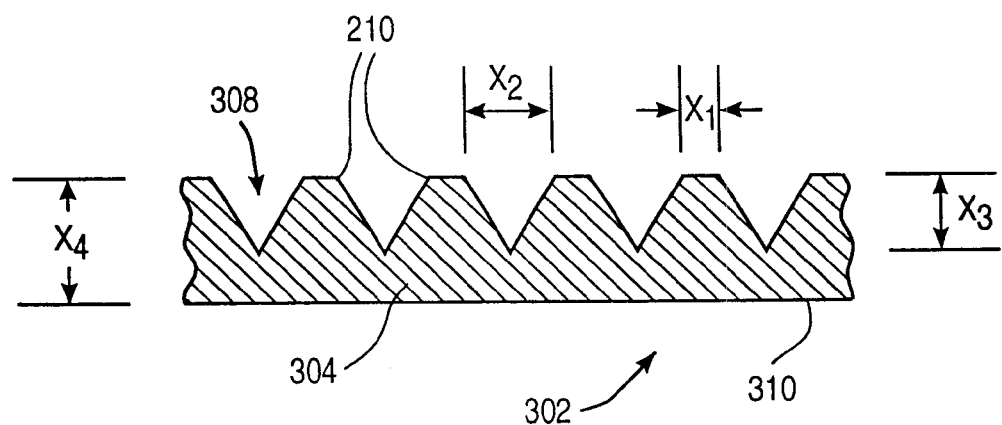
Figure 18A:
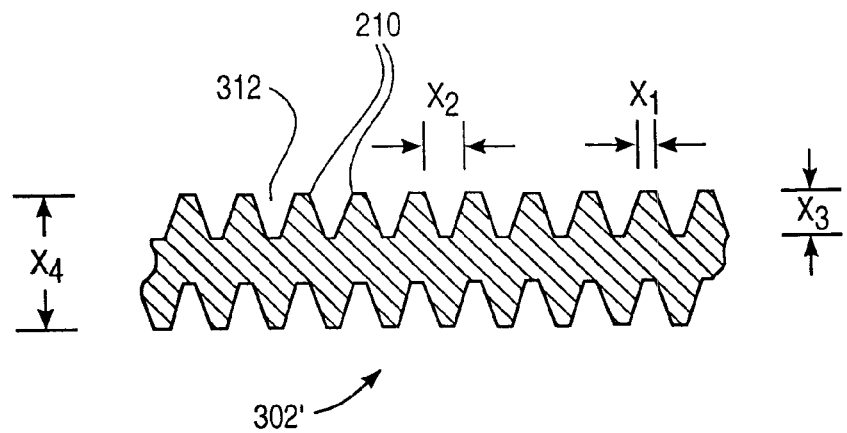

FIGS. 17A, 17B, 18A, 18B and 19 illustrate other alternatively shaped electrodes having transverse grooves or slots formed therein to promote high electric field intensities. Referring to FIGS. 17A and 17B, loop electrode 302 comprises an elongate body 304 having a plurality of spaced, transverse slots 306 (FIG. 17A) or grooves 308 (FIG. 17B) formed therein. The electrode edges 210 of slots 306 and grooves 308 will generally form the "active" portion of the electrode, while an opposing, substantially planar surface 310 forms the "non-active" portion of the electrode 302. An insulating layer (not shown) may be formed over surface 310 to prevent undesirable current flowing from this surface 310 to adjacent tissue. This allows the surgeon to selectively channel relatively high intensity electric fields towards the target site, while minimizing damage to non-target tissue surrounding the target site. Alternatively, electrode 302' may include grooves 312 on both sides so that both sides of electrode 302' are "active", as shown in FIG. 18A by virtue of the electrode edges 210 formed by the grooves or slots 312.

Figure 18B:
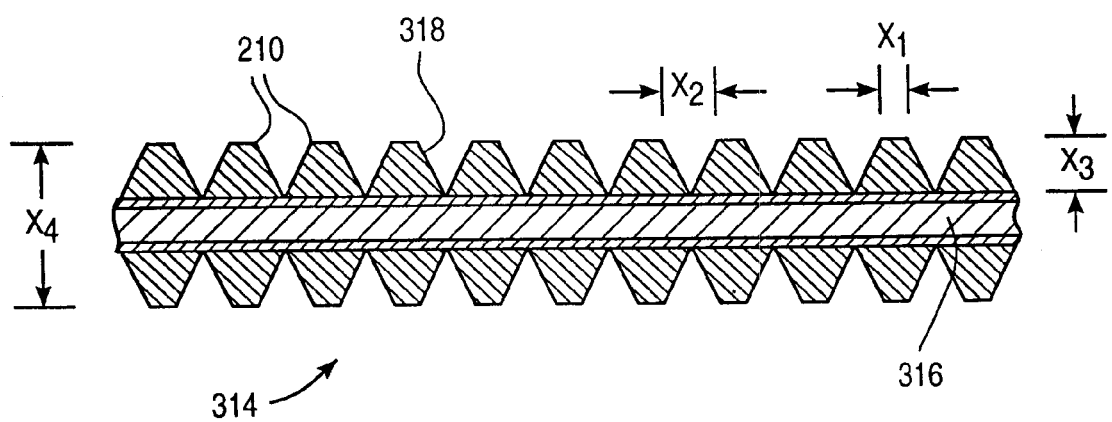

Referring to FIGS. 18B and 19, electrode 314 may have a "necklace" shape, in which electrode members are preshaped, perforated and then placed on an elongate support member (similar to beads on a necklace). Referring to FIG. 18B, one embodiment of electrode 314 includes an elongate support member 316, which may comprise an electrically conducting or insulating material, and a plurality of electrode disks 318 having an inner hole for receiving support member 316. Electrode disks 318 may be in contact with each other or longitudinally spaced from each other. In the latter configuration, support member 316 will be electrically conducting to electrically connect the disks 318 with each other. Referring to FIG. 19, each electrode disk 318 may be separated from each other by an insulating spacer 320. In this embodiment, the electrodes 318 may be electrically isolated from each other so that current limiting elements can be utilized to minimize undesirable current flow into surrounding fluids, as described above.

FIGS. 20A and 20B illustrate further alternative embodiments of the loop electrode according to the present invention. As shown in FIG. 20A, a formed wire has been shaped (e.g., by a shaping die) to form a "V" shape electrode 330. Since the ends 331, 332 of the "V" will promote high electric field intensities, they will preferably face in the cutting direction. In addition, an insulating layer 334 is formed onto the backside 335 of the "V". Similarly, FIG. 20B illustrates a "C" shaped electrode 336 having ends 337, 338 facing the cutting direction and an insulating layer 340 covering an opposite side 342 of electrode 336.

Figure 13:
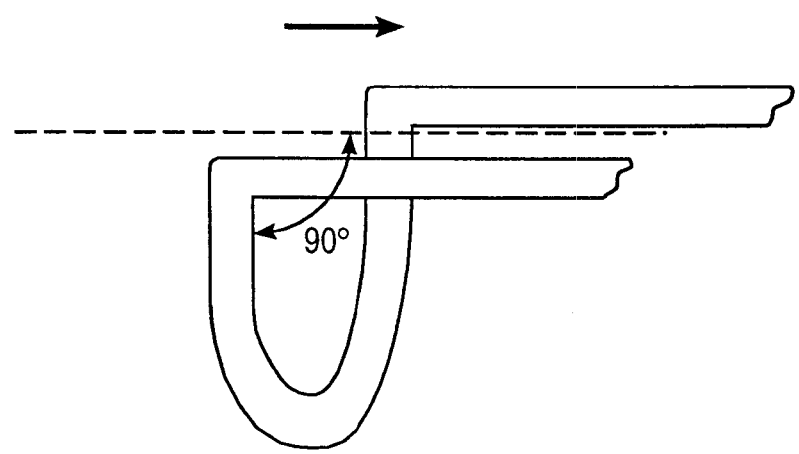
FIG. 13 is an alternative embodiment of the resecting loop electrode of FIG. 9.

As shown in FIGS. 8A and 9, resecting loop electrode 194 is aligned with a plane forming an obtuse angle with the longitudinal axis of shaft 180. The obtuse angle is usually about 110° to about 170°, preferably about 120° to about 150°. During tissue resection, applicant has found that this orientation significantly facilitates initiating the requisite conditions for forming the vapor layer and inducing the discharge of energy therefrom. More specifically, in this orientation, a greater fraction of the surface area and length of loop electrode 194 is in direct contact with the tissue. As such, a greater length of the resection loop is employed thereby directing a greater fraction of the applied energy to the tissue to be resected. With loop electrodes having an obtuse angle orientation, the portion of the length of the electrode in contact with tissue is at least about 30 to 40% greater than the tissue-contacting portion of loop electrodes having a right angle (90%) orientation (see FIG. 13). This results in improved hemostasis of the resected tissue because there is more time to seal transected blood vessels with each pass of the resecting loop. In addition, a smaller fraction of loop electrode 194 is exposed to electrically conducting fluid surrounding the tissue, which minimizes undesirable current flow through this fluid.

Figure 22:
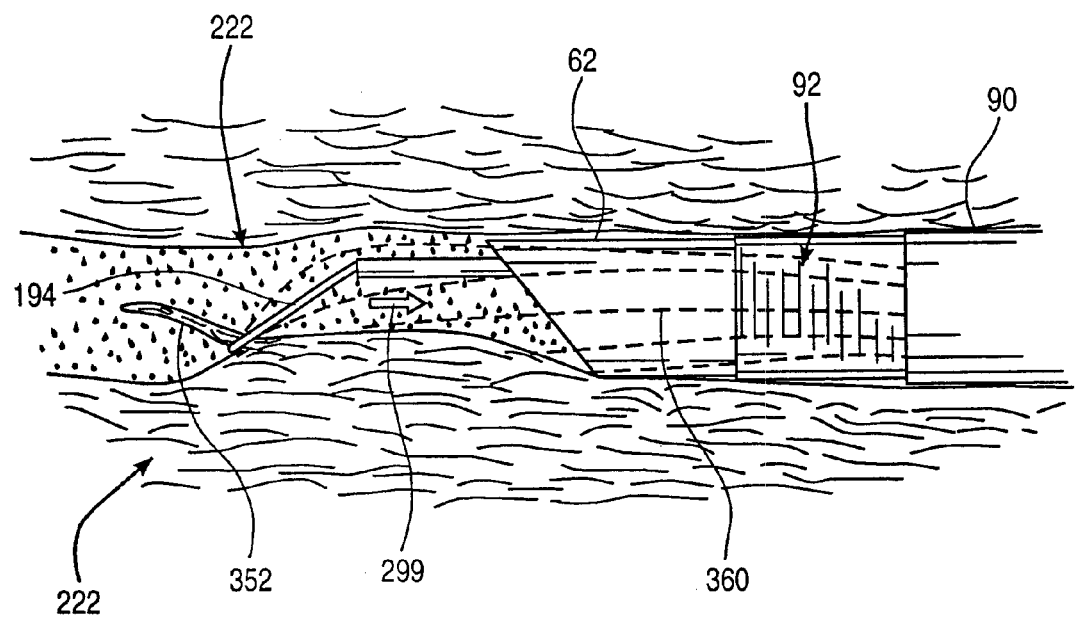
FIG. 22 is an enlarged view illustrating the resection of a prostate tissue portion with the resecting loop electrode of the present invention.

Referring now to FIGS. 21 and 22, a method for applying electrical energy to a target tissue in the patient's body will now be described. In particular, an exemplary procedure for treating an enlarged prostate 222 with electrosurgical system 11 will be described. Introducing sheath 60, return electrode oversheath 16, and resecting loop assembly 112 are introduced transurethrally to the urethra 226 within prostate 222. In the monopolar mode, return electrode oversheath 16 will not be introduced, and a dispersive electrode (not shown) will be externally attached to the patient's skin. While viewing the region via eyepiece 154, voltage can be applied from power supply 28 (see FIG. 1) between resecting loop electrode 194 and the exposed portion 92 of return electrode oversheath 16. Preferably, the applied voltage levels will be above about 500 volts (peak-to-peak). The cutting and resection of prostatic tissue 222 is achieved by engaging resecting loop electrode 194 against the prostatic tissue or positioning loop electrode 194 in close proximity to the prostatic tissue while simultaneously applying voltage from power supply 28 and axially displacing loop electrode 194 towards the distal end of introducing sheath 60 as illustrated by resection vector 299 in FIG. 22.

To complete the current path between the exposed portion 92 of the return electrode and resecting loop electrode 194, electrically conducting irrigant (e.g., isotonic saline) will preferably be delivered from liquid supply 21 through connector 160 along a liquid path between return electrode oversheath 16 and tubular shaft 62 to the target site. Alternatively, the site may already be submerged in liquid (e.g., arthroscopic procedures), or the liquid may be delivered through another instrument. The electrically conductive fluid provides a pathway for electrical current flow between prostatic tissue 222 and exposed portion 92, as illustrated by the current flux lines 360 in FIG. 22. When a voltage difference is applied between loop electrode 194 and exposed portion 92, high electric field intensities will be generated at the shaped edges 210 of electrode 194 to cause ablation of tissue 222.

Referring now to FIG. 22, the design of the surface geometry of resecting loop electrode 194 promotes high current densities at the surface of electrode 194, especially at the shaped edges. In contrast, the current density decreases rapidly with distance from the surface of resecting loop electrode 194. Since the length of the exposed portion 92 of return electrode oversheath 16 will be about 2 to 4 cm, the surface area of exposed portion 92 will be about 5 to 10 cm2. In contrast, the surface area of the resecting loop electrode 194 is about 0.003 cm2. As a result, the current density at exposed portion 92 is 1,700 to 3,400 times smaller than that at resecting loop electrode 194, resulting in current density levels below the threshold of injury to living tissue.

The surgeon can usually effect an efficient cutting motion by simultaneously coagulating smaller vessels transected during the resection of the tissue (see FIG. 22). There may, however, be occasions during the resection of tissue in which larger blood vessels are transected and do not become simultaneously sealed (coagulated) by the higher current densities which surround loop electrode 194. In such situations, resecting loop electrode 194 may be used specifically for coagulating and sealing a transected blood vessel by engaging the tissue at the locus of the bleeding vessel and lightly applying pressure while simultaneously applying a lower voltage level, i.e., a voltage level which is below the threshold for effecting cutting or resection of tissue. Typically, an applied voltage level of less than 500 volts (peak-to-peak), preferably less than 400 volts (peak-to-peak) will be sufficient to effect coagulation of transected blood vessels without cutting or resection of tissue. This dual mode of operation of resecting loop 112 is preferably accomplished by providing dual foot-pedal 37, which includes a cutting mode pedal 39 and a coagulation mode pedal 38. Alternatively, system 111 may be switched between the two modes using voltage control buttons 30 (FIG. 1).

During the course of the tissue resection procedure, telescopic lumen 152 (FIG. 21) and the attached return electrode oversheath 16 can be withdrawn from introducing sheath 160 of resectoscope 10 by releasing a mechanical locking member 350. Following the withdrawal of the working elements of resectoscope 10, the open lumen of introducing sheath 60 can be used to remove one or more tissue fragments 352 (FIG. 22) formed during the resection process.

Figure 23D:
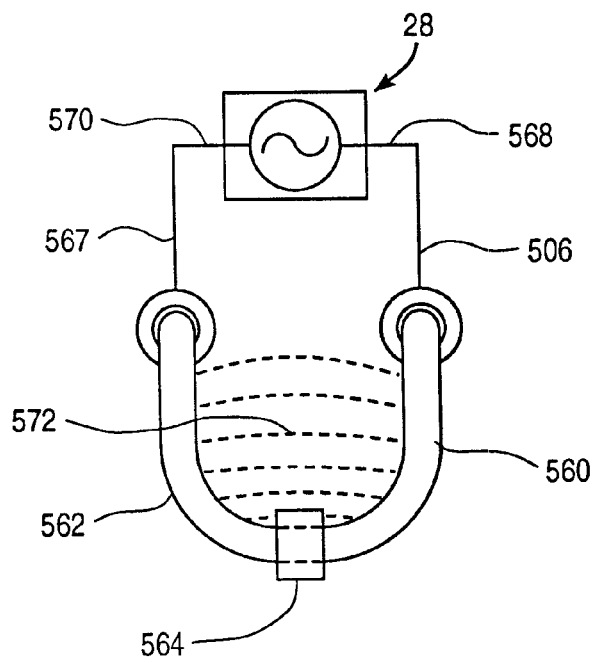
Figure 23E:
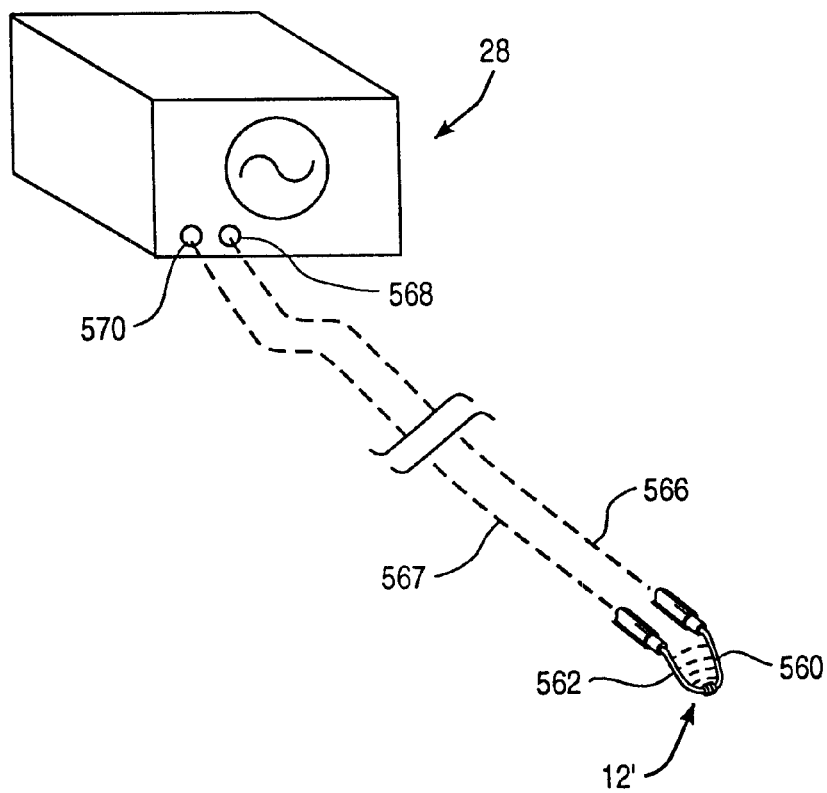

FIGS. 23A-23E illustrate another embodiment of a resecting loop assembly 12' incorporating two electrodes 560, 562 which are electrically isolated from direct contact with each other by an insulating spacer 564. Electrodes 560, 562 may comprise solid wires, hollow tubes, or any of the cross-sectional shapes and configurations discussed above to afford regions of high electric field intensity. Similar to the above embodiments, the proximal ends of electrodes 560, 562 extend from electrically insulating tubular members 192, which extend from hollow arms 186, 188 of a bifurcated support member 184. As shown in FIGS. 23D and 23E, electrodes 560, 562 are each connected to an electrically conducting lead 566, 567 which, in turn, connect to first and second poles 568, 570, respectively, of the output of power supply 28. With this electrical arrangement, current (illustrated by current flux lines 572) flows between electrodes 560, 562 when a radiofrequency voltage difference is applied between poles 568, 570 of power supply 28. The current effects tissue cutting, ablation, shrinkage and/or coagulation in these regions between electrodes 560, 562. A return electrode is not utilized in this arrangement and, therefore, return electrode oversheath 16 is not necessary.

Figure 24A:
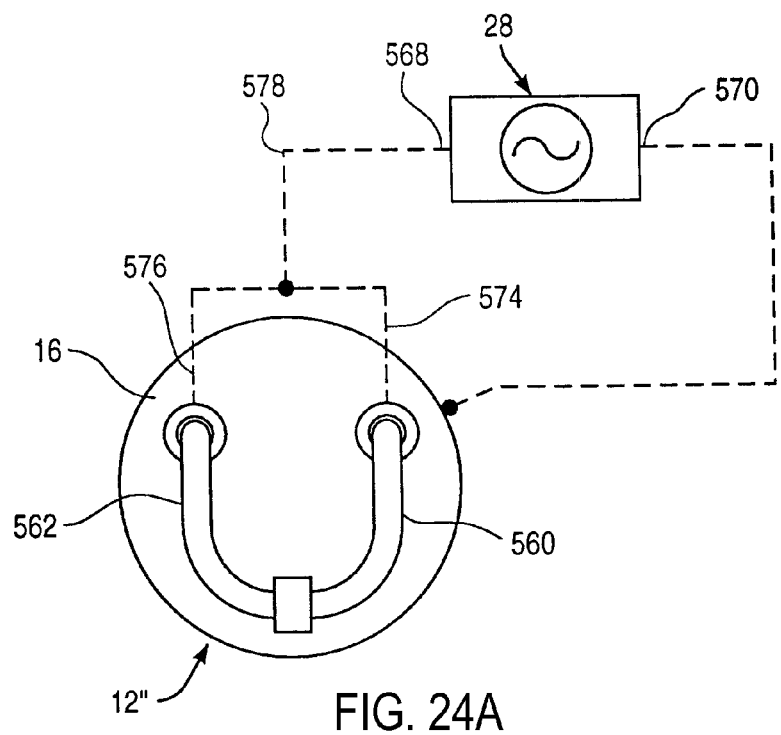
FIGS. 24A and 24B illustrate a resecting loop electrode incorporating two active electrodes connected to a common lead.
Figure 24B:
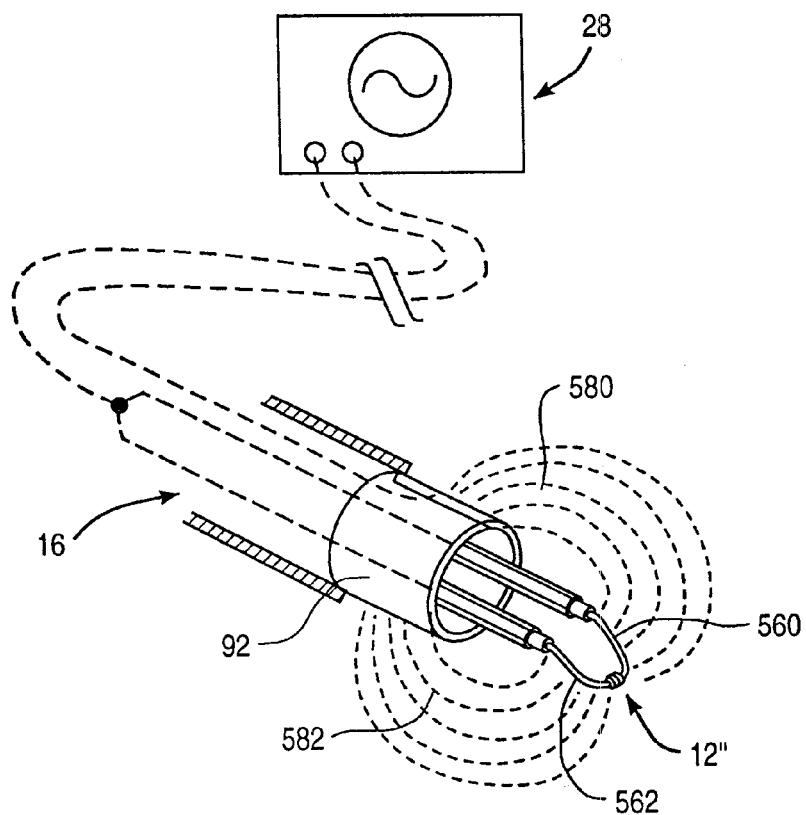
Figure 25A:
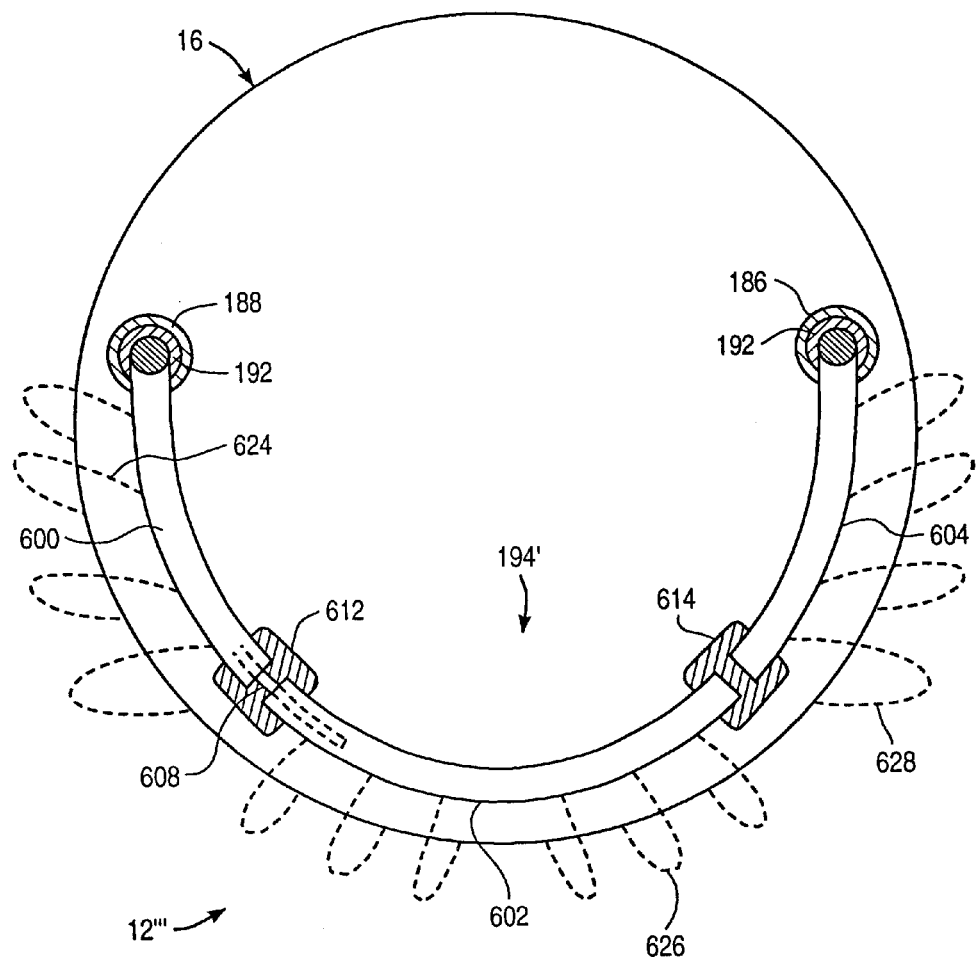
FIGS. 25A and 25B illustrate a resecting loop electrode with three active electrodes.
Figure 25B:
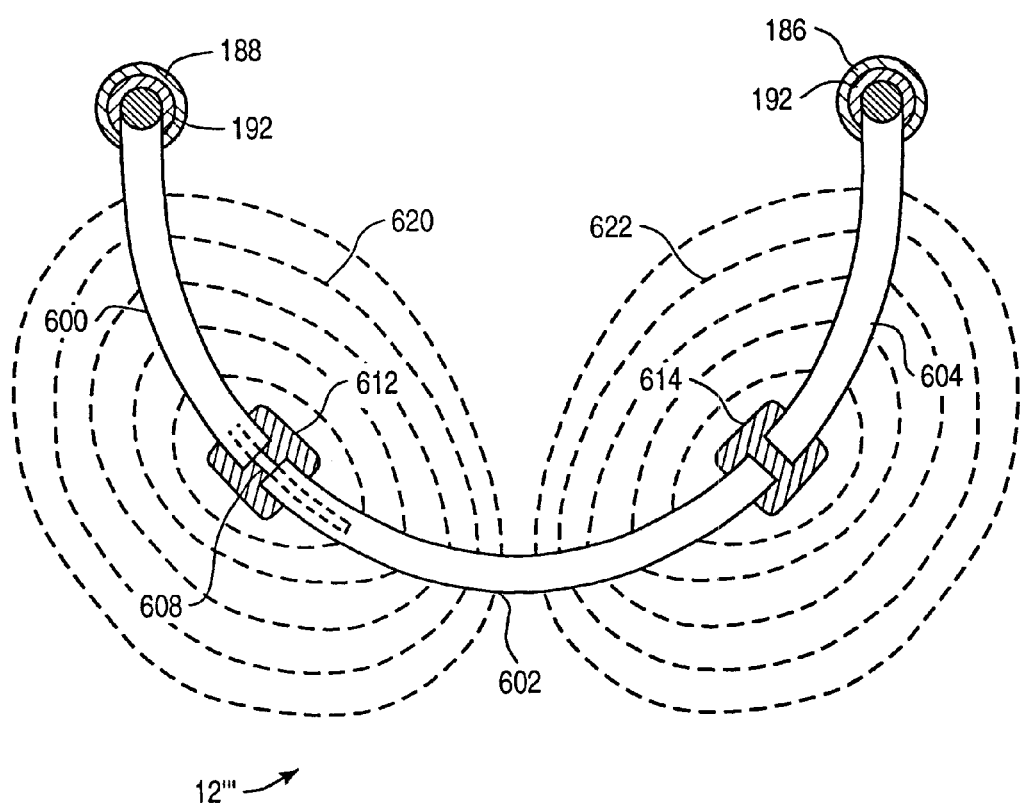

FIGS. 24A and 24B illustrate another embodiment of a resecting loop assembly 12" in which electrodes 560, 562 are each connected to an electrically conducting lead wire 574, 576 which are connected to a common lead 578. The distal end of common lead 578 is connected to a first pole 568 of power supply. In this electrical arrangement, return electrode oversheath 16 (see FIG. 4) will be coupled to second pole 570 of power supply 28. Thus, when electrodes 560, 562 are in contact with tissue and/or electrically conducting fluid and an RF voltage difference is applied between poles 568, 570, electrical current flows independently between electrode 560 and exposed portion 92 of return electrode oversheath 16 and between electrode 562 and exposed portion 92 of return electrode oversheath 16 (as illustrated by current flux lines 580, 582, respectively). FIGS. 25A and 25B illustrate yet another embodiment of a resecting loop assembly 12''' incorporating three electrodes 600, 602, 604 assembled to form loop electrode 194'. Lead wires electrically couple electrodes 600, 602, 604 to power supply 28. One of the lead wires 608 extends through, and is electrically insulated from, electrode 600, as shown in FIG. 25B. Electrodes 600-604 are mechanically spaced and electrically insulated from each other by insulating spacers 612, 614. Similar to previous embodiments, electrodes 600 and 604 extend from electrically insulating tubular members 192, which extend from hollow arms 186, 188 of a bifurcated support member 184.

FIG. 25B illustrates the current flux lines 620, 622 for one electrical arrangement for connected electrodes 600-604 to power supply 28. In this arrangement, electrodes 600, 604 are connected to first pole 568 of power supply 28 (see FIGS. 24D and 24E) in a manner similar to that described above for resecting loop assembly 12' and electrode 602 is coupled to second pole 570 of power supply 28 (i.e., exposed portion 92 of return electrode oversheath 16 is not utilized in this arrangement). When electrodes 600-604 are in contact with tissue and/or electrically conductive fluid and an RF voltage difference is applied between poles 568, 570, electrical current flows between electrodes 600 and 602 and between electrodes 604 and 602, as illustrated by current flux lines 620, 622, respectively. FIG. 25A illustrates the current flux lines 624, 626, 628 for another electrical arrangement for resecting loop assembly 12'''. In this arrangement, electrodes 600, 602 and 604 are independently connected to first pole 568 of power supply 28 and return electrode oversheath 16 is coupled to second pole 570 (see FIGS. 24A and 24B). As shown, current flows independently between each electrode 600, 602 and 604 and exposed portion 92 of return electrode oversheath 16.

Figure 26:
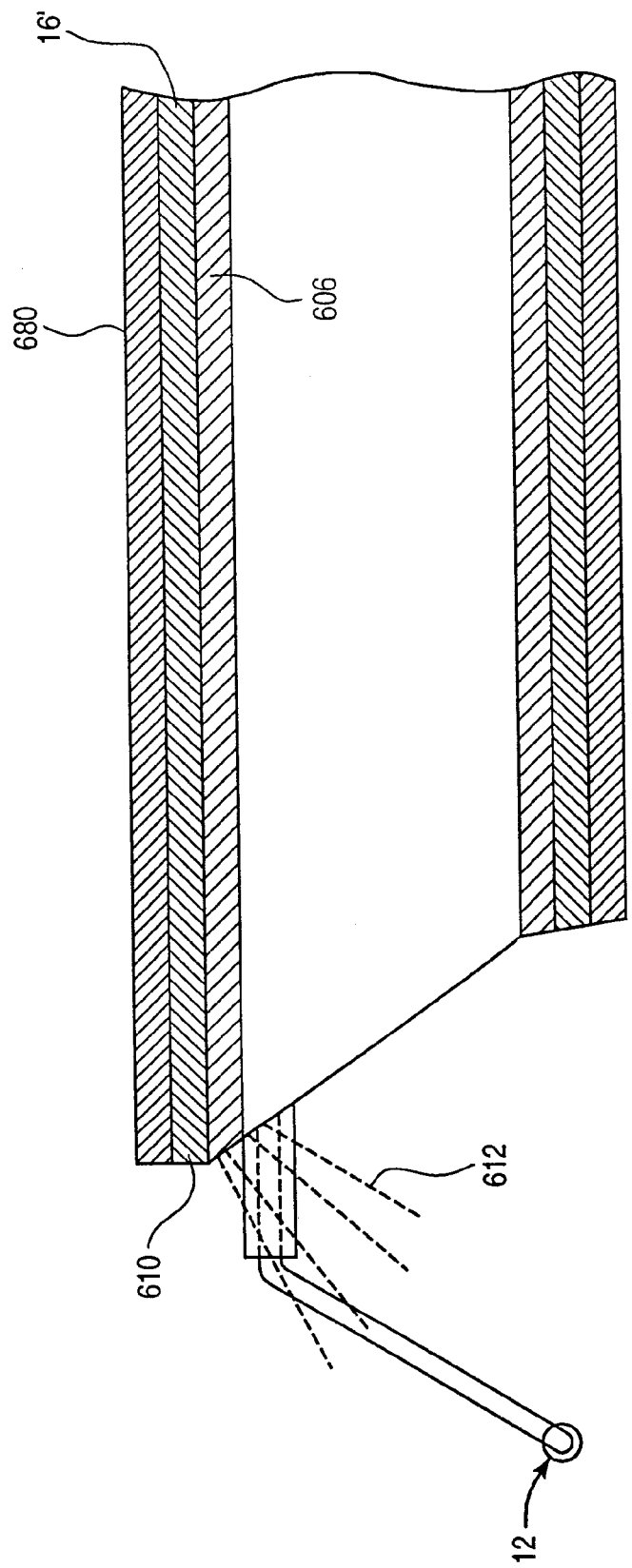
FIG. 26 is a partial side cross-section of an alternative embodiment of the return electrode oversheath of FIG. 4.

As will be evident to those skilled in the art, the foregoing example of resecting loop assembly 12''' can be extended to configurations having four or more electrodes. FIG. 26 illustrates another embodiment of electrosurgical system 11 in which a return electrode oversheath 16' is completely covered with inner and outer insulating layers 606, 680 except for an exposed portion 610 at the distal end of return electrode oversheath 16' that extends beyond the inner insulating layer 606. The exposed portion 610 generates a current flow path 612 between resecting loop electrode 12 and exposed portion 610 of return electrode oversheath 16'. If return electrode oversheath 16' is used in conjunction with and positioned over an insulated resecting loop shaft (not shown), the return electrode oversheath 16' will be insulated on its outer surface only. Alternatively, the sheath of the resectoscope can be replaced with a sheath having the insulation features and return electrode arrangement shown in FIG. 26 such that an additional oversheath return electrode is not required.

Figure 27:
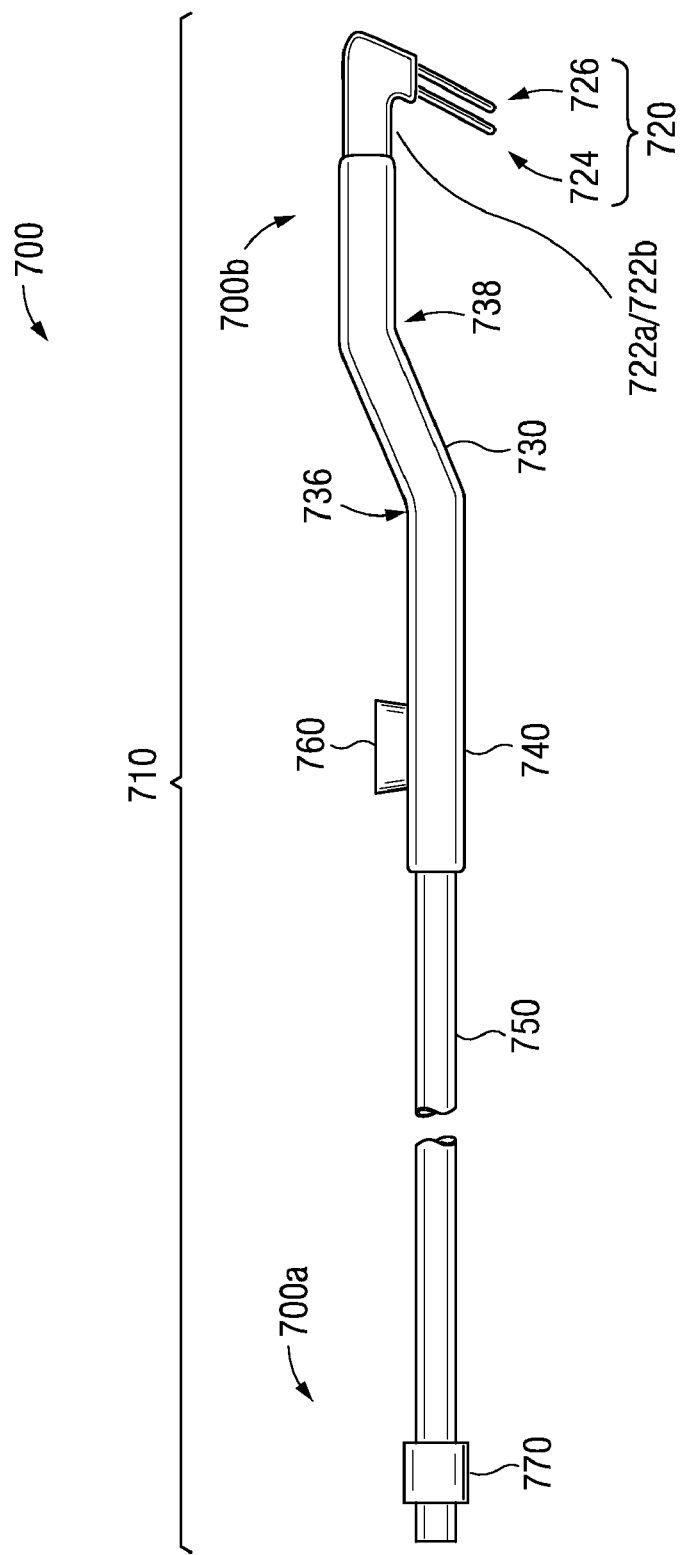
FIG. 27 shows a side view of an electrosurgical probe including a first shaft located at the probe distal end, according to another embodiment of the invention.
Figure 28:
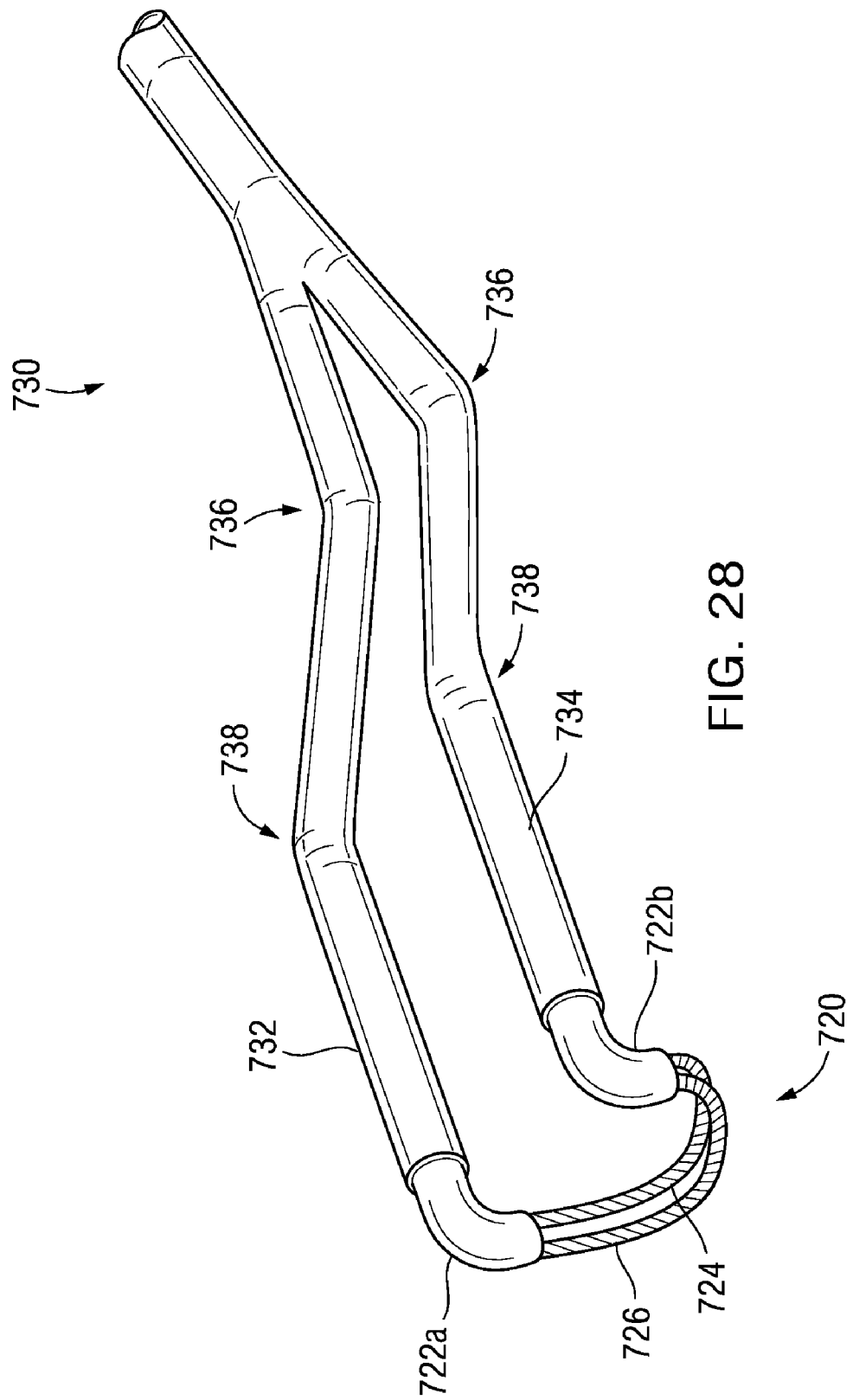
FIG. 28 is a perspective view of the first shaft of the probe of FIG. 27.

FIGS. 27-33 illustrate an electrosurgical instrument having a "double loop" electrode configuration. FIG. 27 shows a side view of an electrosurgical probe 700 including a probe proximal end 700a, a probe distal end 700b, and an elongate body portion 710 having first, second, and third shaft portions 730, 740, and 750, respectively. First shaft portion 730 includes a first bend 736 and a second bend 738. First shaft 730 is bifurcated to provide a first arm 732 and a second arm 734 (FIG. 28). Typically, first and second bends 736, 738 are distal to the point of bifurcation. Probe 700 further includes first and second electrode supports 722a, 722b, respectively, arranged on the distal end of first and second arms 732, 734 (e.g., FIG. 28). First and second electrode supports 722a, 722b each comprise an electrically insulating material, such as a silicone rubber, a ceramic, or a glass. Typically, first and second electrode supports 722a, 722b each include a curved portion 723 (e.g., FIG. 29). In one embodiment, curved portion 723 forms an acute angle with respect to the longitudinal axis of probe 700. An active electrode 724 and a return electrode 726 are disposed between curved portion 723 of each of first and second electrode supports 722a, 722b. Active electrode 724 is located proximal to return electrode 726. The configuration of probe 700, including the bifurcation of first shaft portion 730 together with first and second bends 736, 738, allows a user to view active and return electrodes 724, 726, and points distal thereto, from a substantially axial location proximal to probe proximal end 700a. During use of probe 700, elongate body 710 may be at least partially encased within a sheath, which may be electrically insulating. According to one aspect of the invention, a handle (not shown in FIG. 27) may be affixed at probe proximal end 700a.

Figure 29:
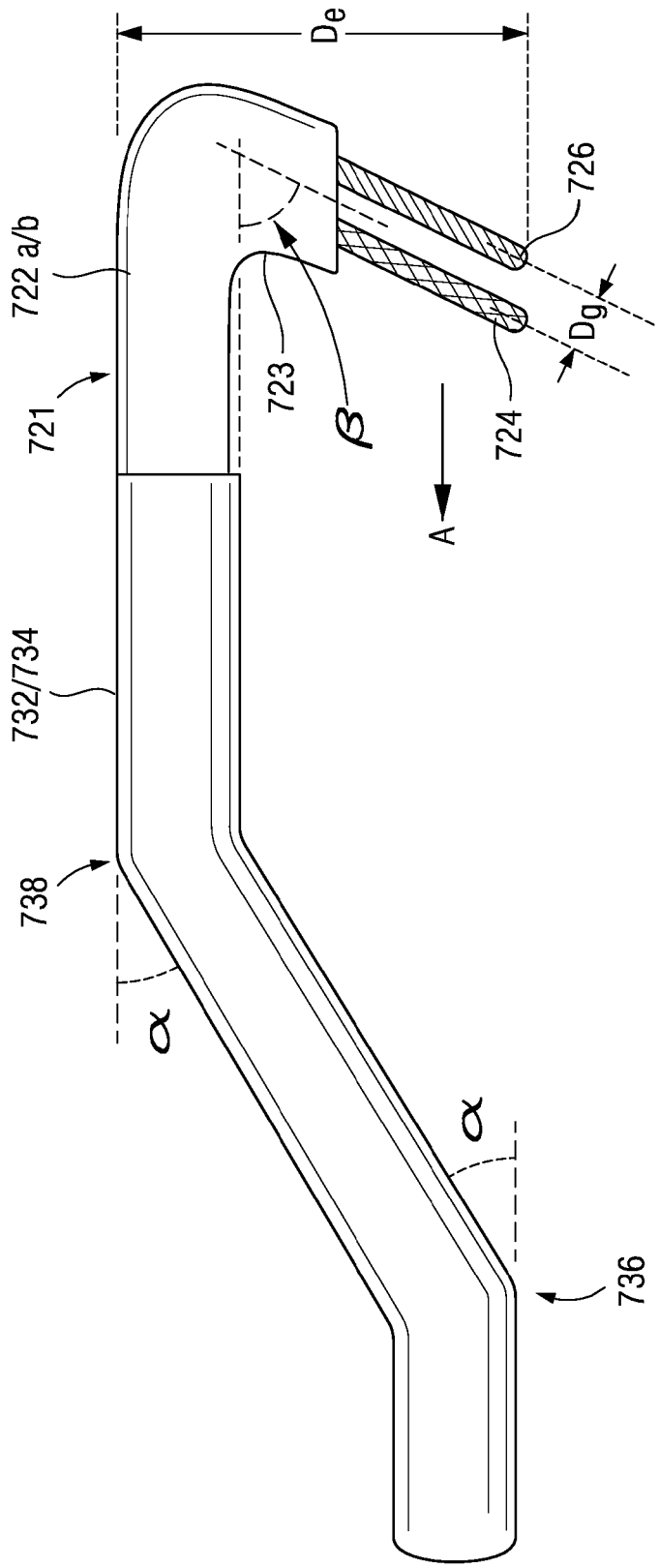
FIG. 29 shows an enlarged view of the distal end of the probe of FIG. 27.

Typically, active electrode 724 and return electrode 726 are arranged at an acute angle with respect to the longitudinal axis of probe 700 (e.g., FIG. 29). In a specific configuration, active electrode 724 is in the form of a loop or partial loop and lies in a first plane, while return electrode 726 is also in the form of a loop or partial loop and lies in a second plane distal to the first plane, wherein the first and second planes are parallel or substantially parallel to each other. Active electrode 724 and return electrode 726 may each have various shapes, such as semicircular or U-shaped (FIGS. 31A-E). Typically, each of active electrode 724 and return electrode 726 comprises a length of a refractory, electrically conducting wire. For example, each of active electrode 724 and return electrode 726 may be composed of a metal such as molybdenum, platinum, iridium, titanium, tantalum, tungsten, stainless steel, copper, nickel, and the like, or their alloys. In one embodiment, at least one of active electrode 724 and return electrode 726 comprises an alloy of platinum with another metal such as tungsten, iridium, or molybdenum. The composition of active electrode 724 and return electrode 726 is at least to some extent a matter of design choice. For example, to increase the coagulation efficiency of electrode assembly 720, active electrode 724 may comprise molybdenum or a molybdenum alloy, while return electrode 726 may comprise stainless steel. As another example, to increase the durability or wear resistance of electrode assembly 720, one or more of active electrode 724 and return electrode 726 may be coated with a material such as chromium or titanium nitride.

Figure 33A:
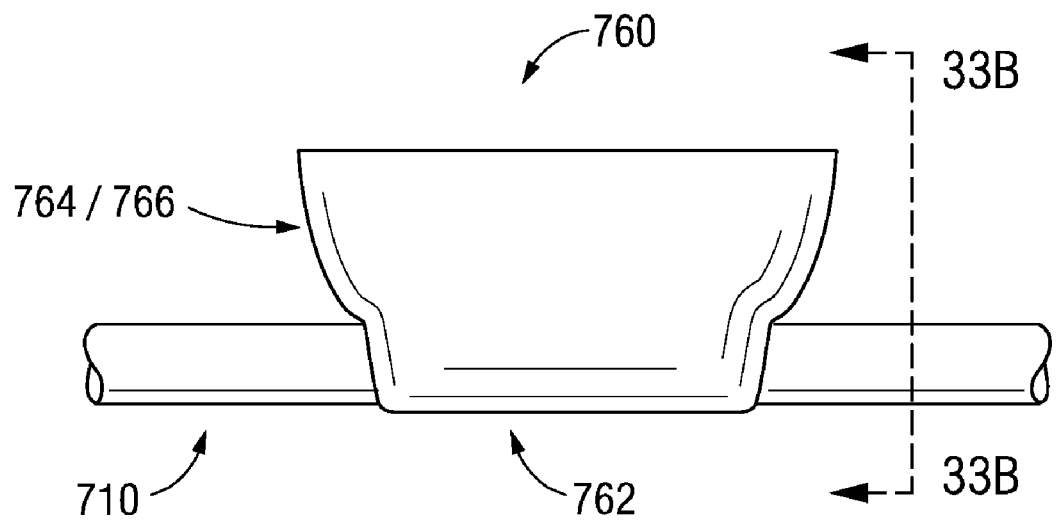
FIG. 33A is a side view of an attachment unit disposed on a shaft of an electrosurgical probe, according to one embodiment of the invention.
Figure 33B:
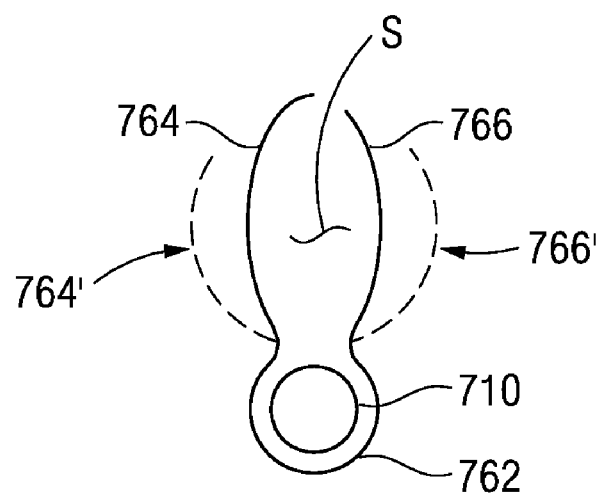
FIG. 33B is an end view of the attachment unit of FIG. 33A, taken along the lines 33B-33B.

Again with reference to FIG. 27, probe 700 typically includes a bipolar connector unit 770 for coupling active electrode 724 and return electrode 726 to opposite poles of a high frequency power supply (e.g., FIG. 1). In one embodiment, bipolar connector unit 770 is disposed on the proximal portion of elongate body 710, e.g., on third shaft portion 750. In one embodiment, probe 700 further includes an attachment unit 760 for removably attaching probe 700 to another instrument, such as a resectoscope, or other endoscope. In a specific configuration, attachment unit 760 comprises a clamp affixed to elongate body 710 at second shaft 740 (FIGS. 33A-B).

Typically, probe 700 has a total length in the range of from about 8 to 18 inches, more typically from about 10 to 12 inches. First shaft portion 730 typically has a length in the range of from about 1 to 3 inches more typically from about 1 to 2 inches. Third shaft portion 750 typically has a length in the range of from about 4 to 8 inches, more typically from about 5 to 7 inches. Second shaft portion 740 is typically intermediate in length between first shaft portion 730 and third shaft portion 750. The diameter of each arm 732, 734 of first shaft portion 730 is typically in the range of from about 0.025 to 0.080 inches, more typically from about 0.040 to 0.060 inches. The configuration of active and return electrodes 724, 726, combined with the relatively narrow diameter of first and second arms 732, 734, allows probe distal end 700b to penetrate a target tissue with relative ease upon application of a suitable voltage between active electrode 724 and return electrode 726. Second shaft portion 740 is usually wider than third shaft portion 750. Second shaft portion 740 typically has a diameter in the range of from about 0.050 to 0.120 inches, more typically from about 0.060 to 0.100 inches. Third shaft portion 750 typically has a diameter in the range of from about 0.040 to 0.100 inches, more typically from about 0.050 to 0.080 inches. In one embodiment, third shaft portion 750 comprises a low friction polymer, such as polytetrafluoroethylene, or polyethylene.

FIG. 28 shows a perspective view of first shaft portion 730 of probe 700, in which first arm 732 and second arm 734 each include a first bend 736 and a second bend 738, wherein the latter is distal to the former. Typically, the distal portions of first and second arms 732, 734 are arranged parallel or substantially parallel to each other. As shown, first and second electrode supports 722a, 722b are arranged axially on the distal terminus of first and second arms 732, 734, respectively. Each of first and second electrode supports 722a, 722b are curved downwards to define curved portion 723 (e.g., FIG. 29). Active electrode 724 and return electrode 726 are suspended between first and second electrode supports 722a, 722b. Typically, each of first and second arms 732, 734 has a diameter in the range of from about 0.020 to 0.100 inches, and more typically from about 0.040 to 0.060 inches. FIG. 29 shows probe distal end 700a in side view, having first bend 736 at an angle α away from the longitudinal axis of probe 700, and second bend 738 at the same or substantially the same angle α towards the longitudinal axis of probe 700. Typically, the angle α is in the range of from about 10° to 35°, and more typically from about 15° to 25°. First and second electrode supports 722a, 722b extend distally from first and second arms 732, 734. Each of first and second electrode supports includes an axial portion 721 in communication with curved portion 723. Active electrode 724 and return electrode 726 emanate from each curved portion 723 (e.g., FIGS. 30A, 30B). In one embodiment, active electrode 724 lies in a first plane, and return electrode 726 lies in a second plane, wherein the first plane is located proximal to the second plane, and the first and second planes are parallel, or substantially parallel, to each other. Active electrode 724 and return electrode 726 are separated by an electrode gap, Dg. Typically, the electrode gap Dg is in the range of from about 0.010 to 0.100 inches, and more typically from about 0.020 to 0.080 inches. As shown, active electrode 724 and return electrode 726 are arranged at an acute angle β with respect to the longitudinal axis of probe 700, wherein angle β is in the range of from about 45° to 85°, and more typically from about 50° to 70°. In one embodiment, active electrode 724 and return electrode 726 extend a distance, De from the upper surface of electrode supports 722a, 722b, wherein the distance De is typically in the range of from about 0.100 to 0.200 inches, more typically from about 0.140 to 0.170 inches. The arrow marked A indicates the principal cutting direction during resection or ablation of target tissue with probe 700. During use of probe 700, current flows from active electrode 724 to return electrode 726, i.e., in a direction substantially opposite to the cutting direction. Applicant considers this arrangement to be favorable for effecting coagulation of any blood vessels severed during ablating or resecting tissue with probe 700.

Figure 30A:
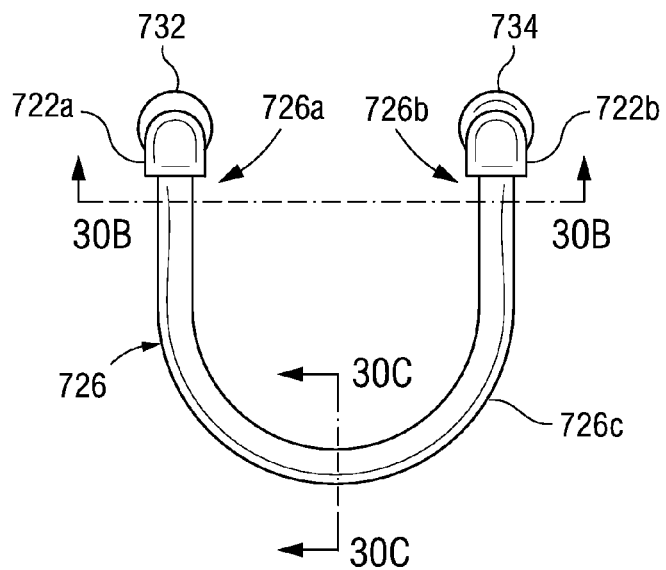
FIG. 30A is an end view of an electrode assembly of an electrosurgical probe, according to one embodiment of the invention.

FIG. 30A is an end view of an electrode assembly 720 of probe 700, according to one embodiment of the invention. Electrode assembly 720 includes active electrode 724 and return electrode 726 (e.g., FIG. 28), each of which is suspended between first and second electrode supports 722a, 722b. Return electrode 726 is located distally to active electrode 724, the latter being hidden by the former in FIG. 30A. Return electrode 726 includes return electrode first and second ends 726a, 726b, respectively, and a return electrode filament 726c. Similarly, active electrode 724 includes active electrode first and second ends 724a, 724b, respectively (FIG. 30B), and an active electrode filament 724c (e.g., FIG. 30C).

Figure 30C:
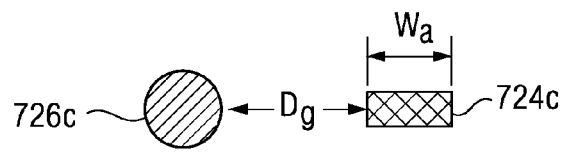
FIG. 30C schematically represents an active electrode and a return electrode as seen along the lines 30C-30C of FIG. 30A.
Figure 30B:
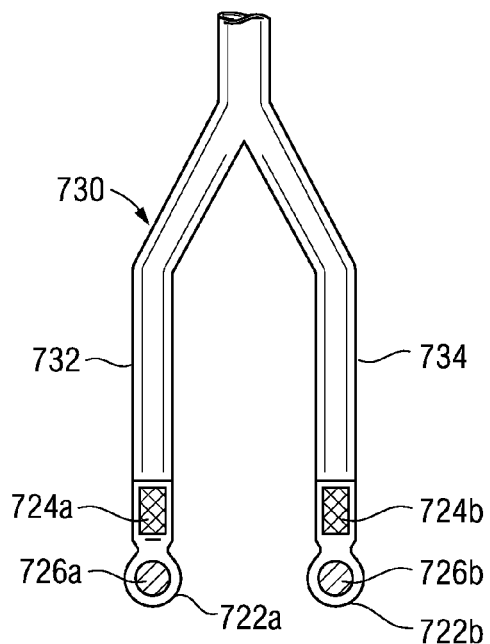
FIG. 30B schematically represents a first shaft and electrode assembly as seen along the lines 30B-30B of FIG. 30A.

FIG. 30B schematically represents first shaft portion 730 and electrode assembly 720 as seen along the lines 40B-40B of FIG. 30A. First shaft portion 730 is bifurcated to provide first arm 732 and second arm 734. First and second electrode supports 722a, 722b are disposed at the distal end of first and second arms 732, 734, respectively. Active electrode first and second ends, 724a, 724b are arranged within first and second electrode supports 722a, 722b, respectively, and return electrode first and second ends, 726a, 726b are similarly arranged within first and second electrode supports 722a, 722b, respectively. FIG. 30C is a cross-sectional view of active electrode filament 724c and return electrode filament 726c, as seen along the lines 30C-30C of FIG. 30A, according to one embodiment of the invention. In the specific configuration depicted in FIG. 30C, return electrode filament 726c is in the form of a round wire, while active electrode filament 724c comprises a wire which is generally rectangular in cross-section. As shown, the long axis of active electrode filament 724c is substantially parallel to the longitudinal axis of probe 700. Typically, active electrode filament 724c has a width, Wa in the range of from about 0.005 to 0.050 inches, and more typically from about 0.010 to 0.020 inches. Typically, return electrode filament 726c has a diameter in the range of from about 0.006 to 0.060 inches, and more typically from about 0.015 to 0.030 inches. The gap between active electrode filament 724c and return electrode filament 726c is indicated in FIG. 30C as Dg (see also FIG. 29).

The double loop electrode configuration increases the amount of current passing through the tissue and ensures that an optimal current density is obtained between the active and return electrodes. In certain embodiments, both electrodes may have similar surface areas resulting in a relatively high current density at the return electrode. As such, in coagulation mode, tissue and blood will stick to both electrodes, creating an isolative layer over them. In cutting mode, the tissue and blood is ablated from the active electrode, creating a "self-cleaning" mechanism. However, there is no such effect on the return electrode and, as a result, tissue and blood may accumulate on the return electrode, progressively decreasing the efficiency of the coagulation mode thereby preventing sufficient hemostasis and extending the necessary length of the procedure.

As such, the perimeter or circumference of return electrode filament 726c is typically greater than the perimeter or circumference of active electrode filament 724c. The greater perimeter or circumference of return electrode filament 726c as compared to the perimeter of active electrode filament 724c may contribute to a greater surface area for return electrode 726 as compared with that of active electrode 724, as is described in greater detail hereinbelow, e.g., with reference to FIG. 32. The relatively large surface area and smooth surface of return electrode 726, as compared with active electrode 724, decreases the likelihood of inadvertent firing from return electrode 726 upon application of a high frequency voltage between active and return electrodes 724, 726. Similarly, the relatively sharp edges of the rectangular active electrode 724 promote high current density at the surface of active electrode 724 upon application of a high frequency voltage between active and return electrodes 724, 726. Other cross-sectional shapes for active electrode 724 and return electrode 726 are possible under the invention. For example, in alternative embodiments active electrode 724 may have a cross-sectional shape as described hereinabove (e.g., with reference to FIGS. 16A-E).

Figure 31A:
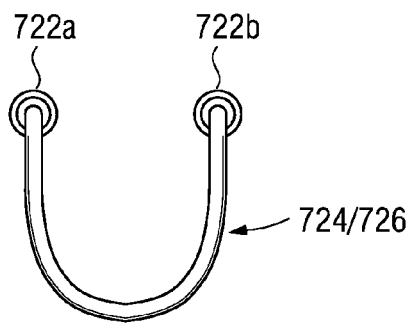
FIGS. 31A-E schematically represent different shapes of an active electrode and a return electrode of an electrosurgical probe, according to various embodiments of the invention.
Figure 31B:
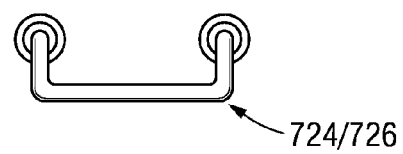
Figure 31C:
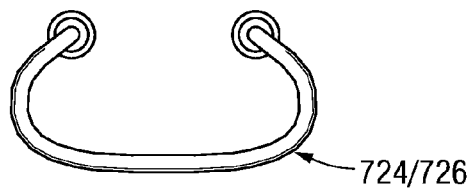
Figure 31D:
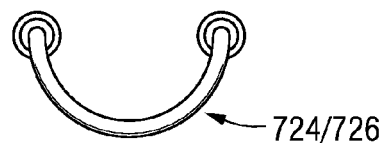
Figure 31E:
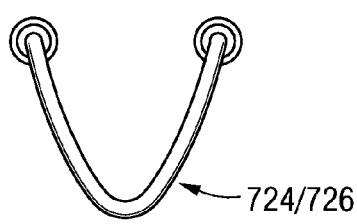

FIGS. 31A-E schematically represent different shapes of active electrode 724 and return electrode 726 of probe 700, according to various embodiments of the invention. The pair of open circles, between which active electrode 724 and return electrode 726 are suspended in each of FIGS. 31A-E, schematically represent first and second electrode supports 722a, 722b. Thus, both active electrode 724 and return electrode 726 may be substantially U-shaped, C-shaped, D-shaped (e.g., semi-circular), or V-shaped, as shown in FIGS. 31A, 41C, 41D, and 41E, respectively. FIG. 31B shows a shallow, flattened U-shape. The shape of active electrode 724 and return electrode 726 is, to some extent, a matter of design choice. Various shapes for active electrode 724 and return electrode 726 can be selected based on the width and depth of tissue to be ablated from a target site, or on the size and shape of a tissue fragment required for biopsy. For example, a deep, narrow cut can be made with substantially V-shaped electrodes (e.g., FIG. 31E), whereas a relatively broad, shallow cut can be made with electrodes having a flattened U-shape (e.g., FIG. 31B). Shapes for active electrode 724 and return electrode 726 other than those depicted in FIGS. 31A-E are also within the scope of the invention. In many embodiments, the respective shapes and/or orientations of the active and return electrodes are the same or substantially similar to each other.

Figure 32:
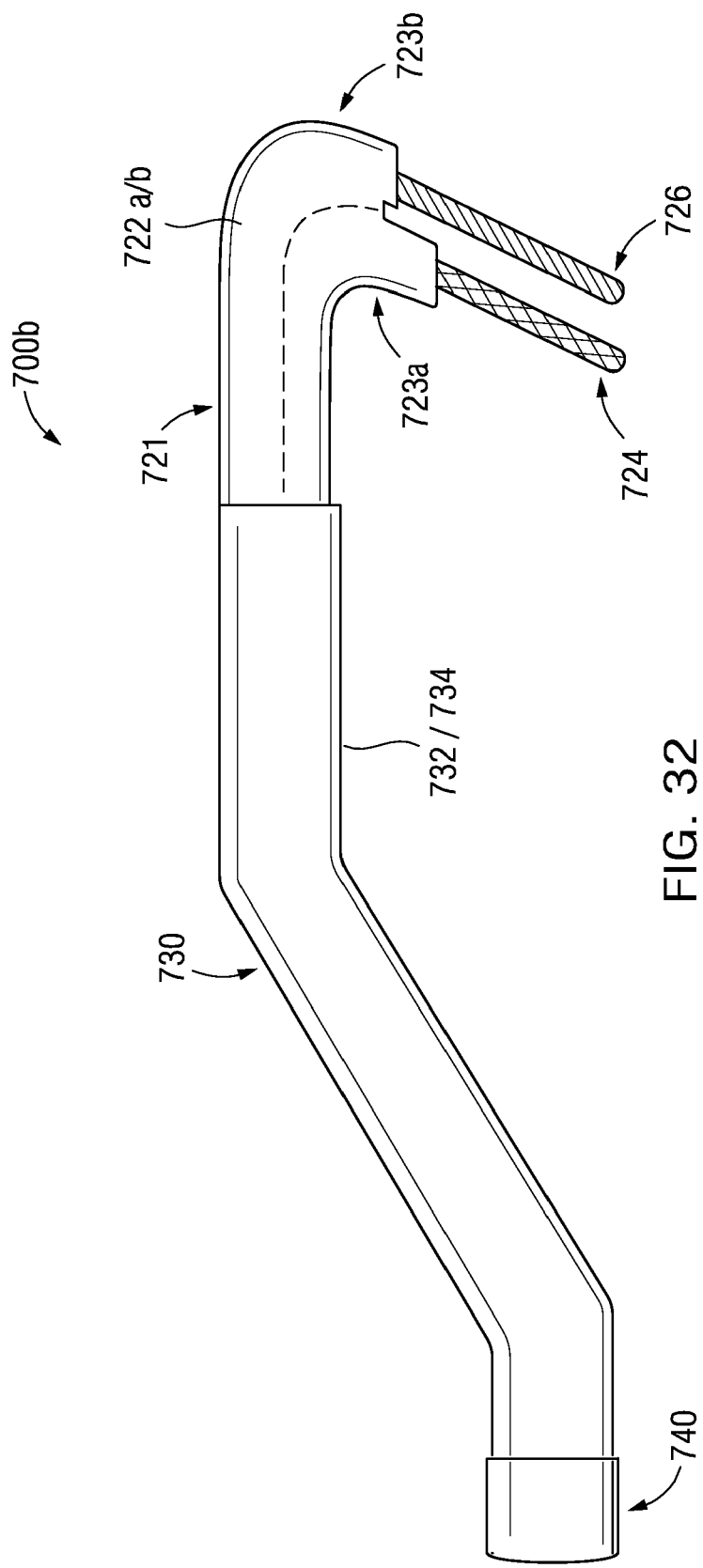
FIG. 32 shows a side view of a probe distal end in which the electrode support extends preferentially along the active electrode, according to another embodiment of the invention.

FIG. 32 shows a side view of probe distal end 700b including first shaft 730, according to another aspect of the invention. In the embodiment of FIG. 32, each of first electrode support 722a and second electrode support 722b includes axial portion 721, a proximal curved portion 723a, and a distal curved portion 723b. Active electrode 724 and return electrode 726 protrude from proximal portion 723a and distal portion 723b, respectively. As shown, proximal portion 723a is longer than distal portion 723b, such that first and second electrode supports 722a, 722b extend preferentially along active electrode 724 as compared with return electrode 726. As a result, the length of active electrode filament 724c is less than the length of return electrode filament 726c. The greater length of return electrode filament 726c, as compared with the length of active electrode filament 724c, combined with a greater circumference or perimeter of return electrode filament 726c, as compared to the perimeter of active electrode filament 724c, typically results in return electrode 726 having a surface area greater than that of active electrode 724. In one embodiment, the ratio of the surface area of return electrode filament 726c to the surface area of active electrode filament 724c is in the range of from about 1.1:1 to about 4:1. And in some embodiments (e.g., where there is sharp angled holes in the active electrode as described herein), the ratio may be less than 1.0 and perhaps, about 0.9.

While a high return-to-active electrode surface area ratio is preferential, it is also preferable to minimize the overall size or geometry of the electrodes in order for them to fit within a small diameter tube sheath, and to provide clearance for the scope, e.g., a resectoscope, over which the loop electrode assembly translates. The surface area ratio may be increased by increasing the surface area of the return electrode or by decreasing the surface area of the active electrode or both. One manner of increasing the surface area with minimal increase in electrode geometry, i.e., with minimal increase in the length and/or perimeter of an electrode, is by texturing the surface of the electrode. Texturing may be accomplished by adding material or elements to the electrode surface. The added material or elements may be fixed or movable relative to the remainder of the return electrode.

Figure 35A:
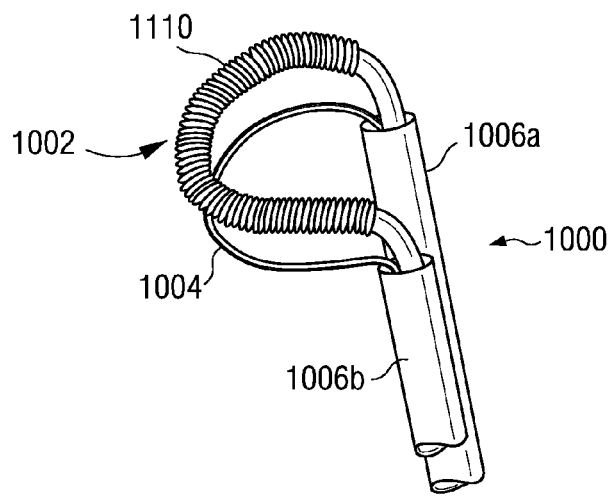
FIGS. 35A-35C illustrate various views of a double loop electrode assembly according to one embodiment of the present invention.
Figure 35B:
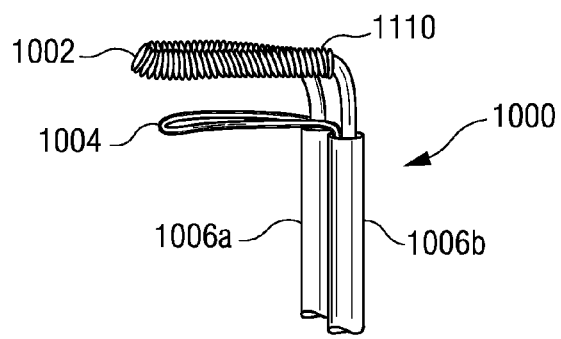
Figure 35C:
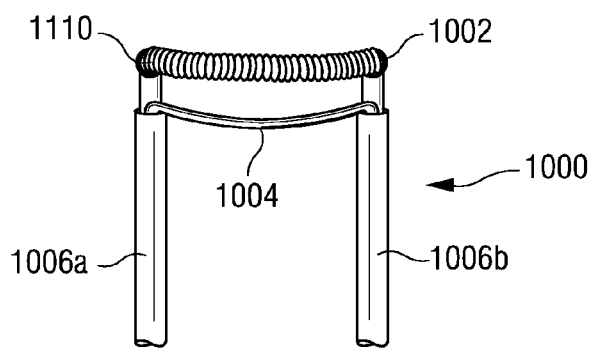
Figure 36A:
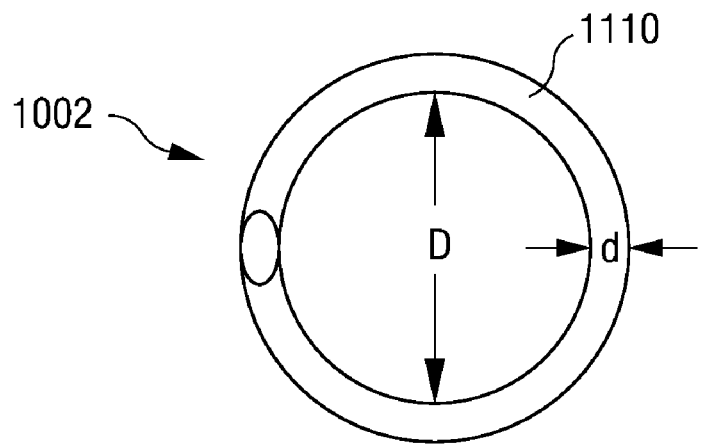
FIGS. 36A and 36B show enlarged cross-sectional and side views of the return electrode of the electrode assembly of FIGS. 35A-35C.
Figure 36B:
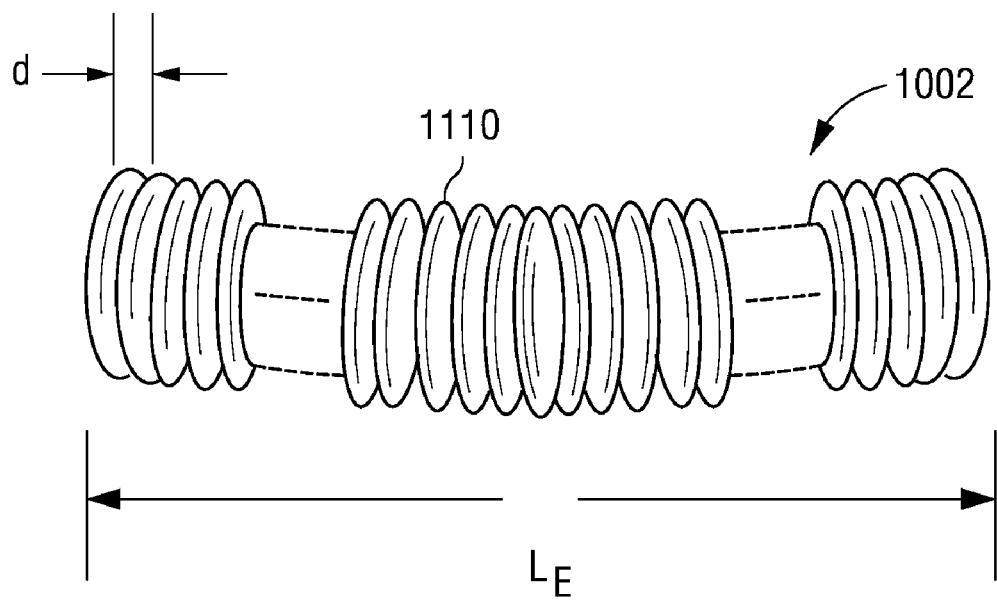

FIGS. 35A-35C illustrate perspective, side and front views of an electrosurgical probe 1000 employing one such texturing means. Electrosurgical probe 1000 has a double loop electrode configuration similar to that of the probe of FIGS. 27-29, having return electrode 1002 positioned distally of active electrode 1004 in a spaced-apart, substantially parallel relationship. Return and active electrodes 1002, 1004 are made of formed wire and extend substantially transverse to electrode arm supports 1006a, 1006b and may form any suitable angle with support arms 1006a, 1006b as discussed above. Encircling the length of return electrode 1002 is a thin-diameter metallic coil 1110 such as a helical coil. While the small diameter of coil 1110 ($d$) adds a minimal increase to the original or filament diameter of return electrode 1002 (D), the effective surface area of the return electrode may be increased substantially depending on the number of turns within coil 1110. With reference to FIGS. 36A and 36B which illustrate enlarged cross-sectional and side views, respectively, of return electrode 1002 with coil 1110, this relationship is mathematically illustrated. Without the use of coil 1110, the surface area of the electrode ($S_{E1}$) is as follows:

$$S_{E1} = L_E \times D \times \pi,$$

where $L_E$ is the length of the return electrode and D is the diameter of the return electrode without coil 1110. With coil 1110, the effective surface area of the electrode ($S_{E2}$) is represented by the following relationship:

$$S_{E2} = S_T \times n,$$

where $S_T$ is the surface area of each turn of the coil and n is the number of coil turns within coil 1110, which are represented, respectively, by the following relationships:

$$S_T = L_T \times d \times \pi,$$

$$n = L_E / d,$$

where d is the diameter of the coil wire and $L_T$ is the length or circumference of a single coil turn represented by the following relationship:

$$L_T = (D+d) \times \pi.$$

As such, the effective surface area of the return electrode ($S_{E2}$) is as follows:

$$S_{E2} = ((D+d) \times \pi) \times d \times \pi) \times L_E / d$$

or $$S_{E2} = L_E \times (D+d) \times \pi^2.$$

Any other suitable texturing means may be employed to increase the surface area of the return electrode including, but not limited to, small beads threaded over the core wire. The beads may be fixed to the wire or allowed to roll about the axis of the wire. As with the coiled configuration discussed above, the smooth and rounded surfaces of the beads facilitated translation of the electrode assembly over a scope and through tight or narrow passages. Texturing elements which are movable relative to the electrode core of wire provide the further advantage of facilitating the cleaning of the return electrode. Although the return electrode shown in FIGS. 35A-35C includes a central formed wire surrounded with a helical coil, another design includes a coil without the core wire extending axially there through. In other words, the return electrode may be a helical coil. The active electrode and other components may be as described herein. Accordingly, a double loop assembly may be provided that includes a helical coil return electrode and an active wire or active screen electrode.

As mentioned above, another way in which to obtain a desired return-to-active electrode surface area ratio is to reduce the surface area of the active electrode. This can be accomplished by removing material from the electrode such as by forming cuts, notches, holes or pores within the electrode. The removal of material may further serve to provide one or more sharp edges to improve the ablation performance of the electrode.

Figure 37A:
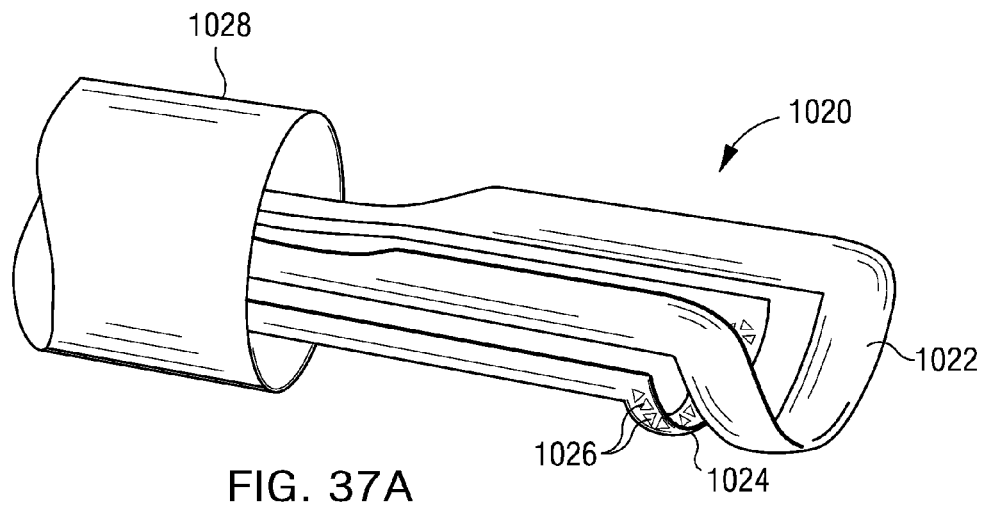
FIGS. 37A and 37B illustrate perspective and planar views of another double loop electrode assembly of the present invention.
Figure 37B:
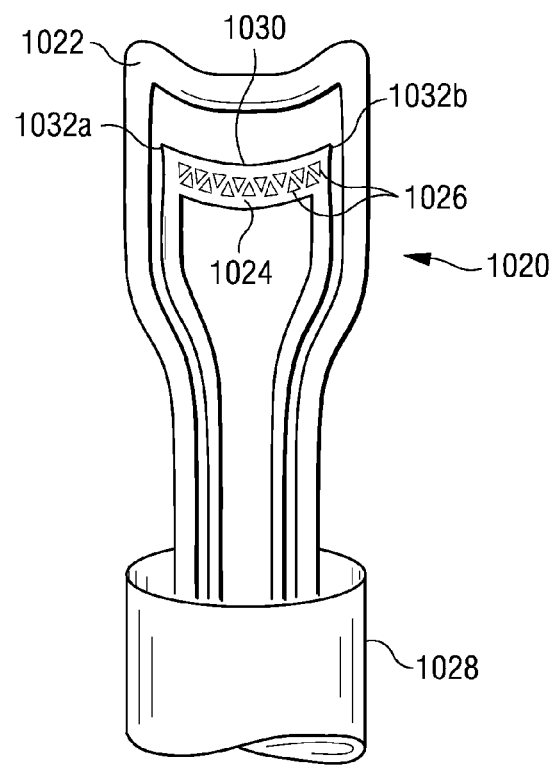

FIGS. 37A and 37B illustrate another double loop electrode assembly 1020 of the present invention extending from an electrode support 1028 and having a distally positioned return electrode 1022 and a proximally positioned active electrode 1024. Both electrodes are flat or planar (e.g., a sheet of metal) and are folded or bent, providing a semi-circular cross-sectional profile, thereby providing a low-profile assembly which minimizes the necessary size of the sheath or tube through which it is delivered while allowing clearance for translation of a scope other instruments through the partial lumen defined by the semi-circular profile. Active electrode 1024 is provided with a sharp distal edge 1030 and corners 1032a, 1032b. These serve to produce a high electric field intensity at its cutting end. The active electrode thus may have a sharp edge and the return may also have a sharp edge. Additionally, active electrode 1024 has a plurality of surface-area reducing holes 1026 there through to increase the edge/surface area ratio of the electrode and thereby further increase the electric field intensity provided by the electrode. The holes 1026 preferably have shapes with acute angles such as triangles. These holes may have sharp edges which provide high current densities. Tissue removal is further facilitated by the holey physical structure of active electrode 1024, which provides a grating effect on the target tissue to be removed. In this embodiment, holes 1026 have a triangular configuration, each of which provides three straight edges to enhance the edge effect while reducing the effective surface area of active electrode 1024, thereby increasing the current density along the length of active electrode 1024. The holes may have any suitable shape, including but not limited to square, rectangular, hexagonal, octagonal, star-shaped, slotted, circular, etc. The size of the holes may be selected based on the particular tissue removal application in which the electrodes are used, wherein each hole may define or bound an area typically have a size in the range from about 0.15 mm$^2$ to about 0.30 mm$^2$, or may be very small so as to provide a porous electrode structure.

While any practical means and technique may be used to fabricate and form electrode assembly 1020, microreplication techniques including but not limited to chemical etching, electron discharge machining, laser cutting and/or microstamping of the electrodes are cost efficient fabrication methods which lend themselves to thin metal applications in which fine features are desired. Accordingly, the shape of the electrodes themselves and their respective edge geometries and porosities may be formed by one or more of these microreplication techniques. The desired three-dimensional profile of the electrodes or electrode assemblies may then formed by applying and forming them about a mandrel of a desired shape.

Chemical etching fabrication may be done on sheets or continuous coils of suitable conductive material. Suitable materials used to form the electrodes include, but are not limited to, tungsten, molybdenum, stainless steel, etc. The sheet provides a thin metal base typically has a thickness in the range from about 0.005 to 0.015 IN. The etching process is commenced by applying a photoresistant layer to one or both sides of the metal base as desired. Next, lithography techniques are used to precisely define the geometries that will be etched partially into or completely through the metal base. Specifically, the base metal is selectively masked to protect areas of the metal which are not to be etched and to expose areas of the metal which are to be etched (i.e., to form holes therein). Etching is accomplished by an electrochemical dissolution process wherein an acid substance is applied to the surface of the base metal and a current is conducted through the metal. The areas of the metal surface which are not masked are then dissolved by the acid. After the etching step, the photoresist layer is stripped from the surface of the metal. The electrodes are typically stamped or cut form the sheet subsequent to the etching process.

Microstamping, another technique suitable for fabricating all-metal electrodes involves the use of dies which have been precisely machined such as by electro-discharge machining. Long sheets or webbings of a substrate metal are continuously or semi-continuously fed into a stamping press between die sets to selectively blank (i.e., punch holes in), coin (i.e., deform one side of the metal) and/or deform the metal substrate from both sides, e.g., to obtain the desired electrode profile.

FIG. 33A is a side view of an attachment unit 760 disposed on elongate body 710 of an electrosurgical probe 700, according to one aspect of the invention. In one embodiment, attachment unit 760 comprises a clamp having a base 762 affixed to elongate body 710, and first and second walls 764, 766, respectively. Attachment unit 760 is adapted for affixing probe 700 to another surgical instrument, such as a resectoscope or other endoscope. In one embodiment, attachment unit 760 is adapted for affixing probe 700 to an endoscope so as to align probe 700 with various components of an endoscope. For example, probe 700 may be affixed via attachment unit 760 to an endoscope (e.g., a resectoscope (FIG. 2)) such that probe 700 can be axially reciprocated within an introducer shaft of the endoscope. Similarly, according to another aspect of the invention, probe 700 may be attached to an endoscope via attachment unit 760 such that a user of probe 700 can view electrode assembly 720, and points distal thereto (e.g., target tissue), through an eyepiece of the endoscope.

FIG. 33B is an end view of attachment unit 760 taken along the lines 43B-43B of FIG. 33A. Base 762 partially encircles elongate body 710 and is affixed thereto. Solid lines marked 764, 766 represent first and second clamp walls, respectively, with attachment unit 760 in the vacant configuration (for example, probe 700 is unattached to an endoscope). Dashed lines marked 764', 766' represent first and second clamp walls, respectively, with attachment unit 760 in the occupied configuration, with space S occupied, for example, by a cylindrical component of an endoscope. Attachment unit 760 may be constructed from a sheet of stainless steel, or similar material. In a specific configuration, attachment unit 760 may be affixed via base 762 to second shaft 740.

Figure 34B:
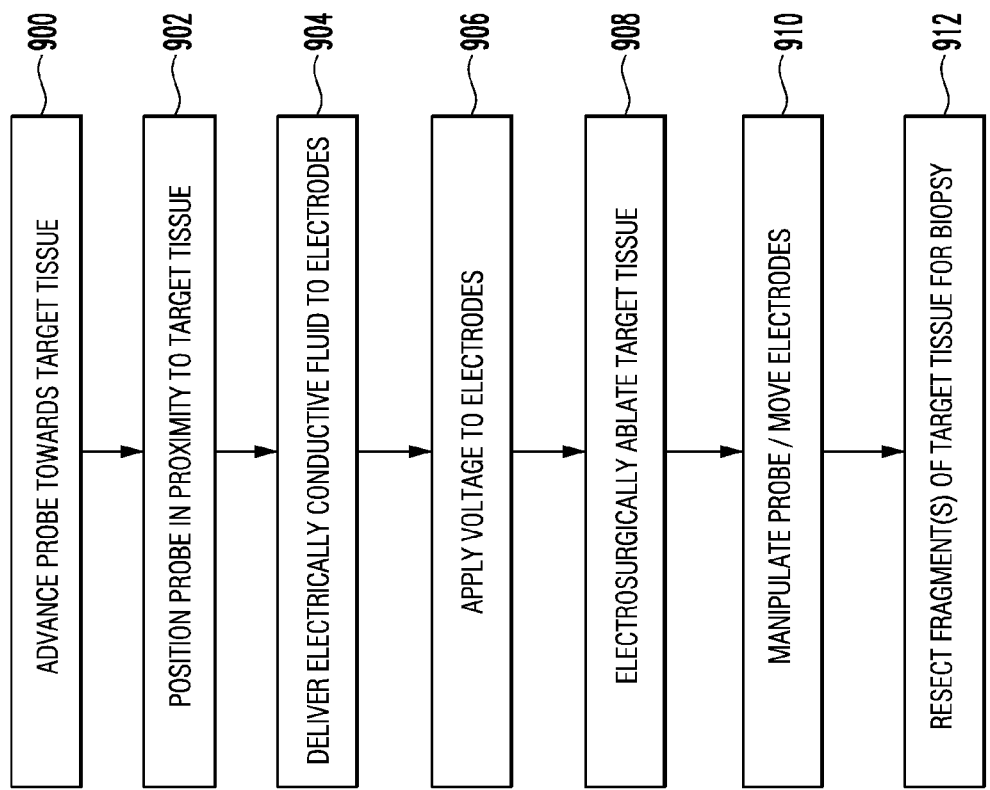
FIG. 34B schematically represents a number of steps involved in a method of surgically removing a fragment of target tissue and vaporizing a portion of the target tissue, according to another embodiment of the invention.
Figure 34A:
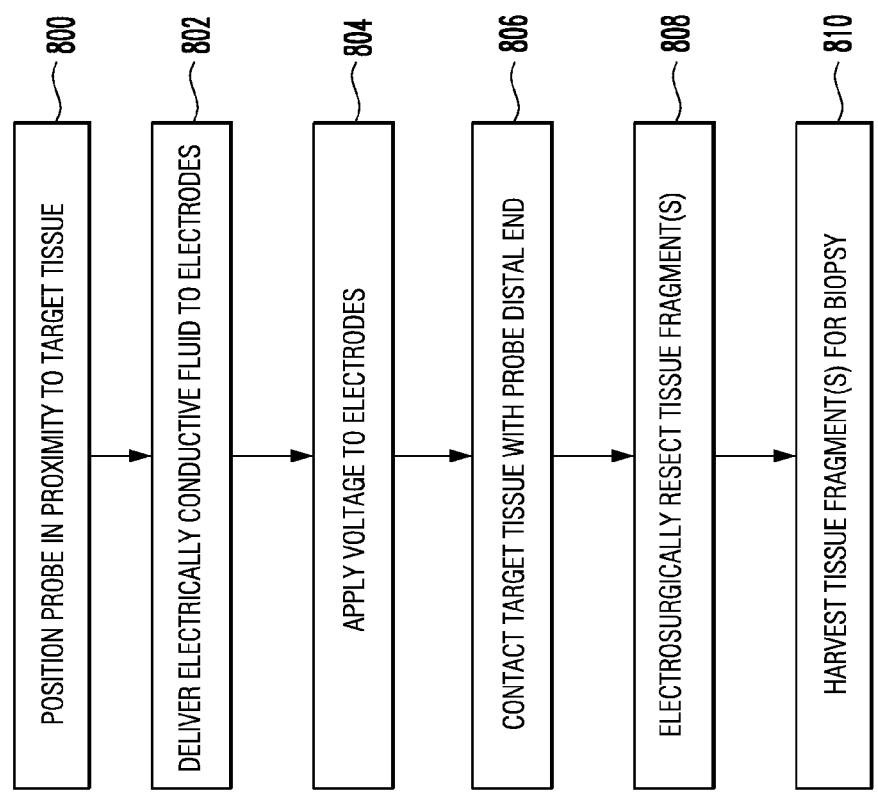
FIG. 34A schematically represents a number of steps involved in a method of retrieving a fragment of tissue from a target tissue or organ, according to another embodiment of the invention.

FIG. 34A schematically represents a number of steps involved in a method of resecting and harvesting a fragment of tissue from a target tissue or organ, according to the instant invention, wherein step 800 involves positioning the distal end of an electrosurgical probe in at least close proximity to the target tissue. The probe positioned during step 800 may be any one of the electrosurgical probes described hereinabove, e.g., with reference to FIGS. 1 through 33B. In one embodiment, the probe positioned during step 800 includes an electrode assembly having an active electrode and a return electrode located distal to the active electrode. In one aspect of the invention, the active electrode may be disposed between first and second arms of a bifurcated shaft. Step 802 involves delivering an electrically conductive fluid to at least one electrode. The electrically conductive fluid, which may be a gel or a liquid such as isotonic saline, provides a current flow path between the active electrode and the return electrode. The electrically conductive fluid may be delivered via a suitable fluid delivery element. The fluid delivery element may be integral with the probe, or may be a component of a separate device, as is well known in the art. Alternatively, the fluid delivery element may be integral with another surgical instrument to which the probe is attached (e.g., FIG. 2). In one embodiment, the electrically conductive fluid is delivered to the target site. In another embodiment, the probe distal end bears a distal return electrode, and an active electrode separated from the return electrode by an electrode gap, and the electrically conductive fluid is delivered to the probe distal end to submerse, or partially submerse, the active and return electrodes. In certain procedures, the electrically conductive fluid is delivered to the body region or cavity surrounding the target site prior to and/or during the procedure to submerse the target site within electrically conductive fluid. For example, in hysteroscopic procedures, the uterus may be distended with electrically conductive fluid prior to introduction of the probe and the conductive fluid is continually circulated in the uterus throughout the procedure. In TURP procedures, the urethra may be filled with electrically conductive fluid and circulated in a similar manner.

Step 804 involves applying a high frequency voltage between the active and return electrodes. The high frequency voltage applied in step 804 will typically be in the range described hereinabove. For example, in step 804 the applied voltage may be in the range of from about 50 volts RMS to 500 volts RMS, and have a frequency in the range of from about 20 KHz to 1 MHz. Step 806 involves contacting the target tissue with the probe distal end. In one embodiment, a fragment of tissue may be removed for biopsy by translating the active and return electrodes, e.g., in a proximal direction, over the surface of the target tissue (step 808). In one embodiment, the probe distal end, including the active and return electrodes, is adapted for penetration into the target tissue. Accordingly, in another embodiment, a fragment of tissue may be resected from within the bulk of the target tissue by inserting the probe distal end within the target tissue to a certain depth. The actual depth of penetration of the probe distal end within the target tissue may range from a 0.1 mm to about 1 cm., or more, depending on a number of factors, such as the type of target tissue, the condition of the tissue/symptoms of the patient, the size and configuration of the probe, and the desired number and size of the fragment(s) required for biopsy.

When appropriate, the high frequency voltage described in step 804 may be applied during step 806, for example, to allow the probe distal end to readily penetrate the target tissue. Regardless of the degree of penetration of the tissue by the probe distal end, resection of at least one tissue fragment in step 808 is typically effected via a cool ablation process involving the molecular dissociation of tissue components to form low molecular weight (e.g., gaseous) by-products. Typically, during electrosurgical ablation or resection of tissue according to the instant invention, the target tissue is exposed to a temperature in the range of from about 45° C. to 90° C., thereby avoiding or minimizing thermal damage to adjacent tissue.

In an additional step (not shown in FIG. 34A), ablation by-products may be removed from the surgical site via a suitable aspiration element, such as a suction device. Such an aspiration element may be integral with the probe, or may be a component of a separate device. Alternatively, the aspiration element may be integral with another surgical instrument to which the probe is attached (e.g., FIG. 2). Suction devices are well known in the art. Step 810 involves harvesting the at least one fragment of target tissue (resected in step 808) for tissue analysis (biopsy). In some procedures, the ablation by-products will be removed with the circulating conductive fluid. The at least one fragment of target tissue may be retrieved in step 810 by suction, circulation of a fluid, or via a mechanical device, e.g., using a forceps-like instrument.

FIG. 34B schematically represents a number of steps involved in a method which combines, in a single procedure, electrosurgical ablation of target tissue and harvesting of a resected tissue fragment according to another embodiment of the invention. In step 900, an electrosurgical probe, such as one of the embodiments described hereinabove with reference to FIGS. 1 through 33B, is advanced towards a target tissue. According to various embodiments of the invention, step 900 may involve advancing the probe towards the target tissue, percutaneously, via an incision, or via a natural opening. The probe may be so advanced towards the target tissue, either alone, or in combination with an introducer device, e.g., a cannula, or an introducer sheath of an endoscope or resectoscope. Step 902 involves positioning the probe distal end in at least close proximity to the target tissue. In one embodiment, the probe includes a shaft having an electrode assembly disposed on the shaft distal end, the electrode assembly comprising a proximal active electrode and a distal return electrode. According to one aspect of the invention, the shaft is bifurcated and includes first and second arms, the first and second arms bearing first and second electrode supports, respectively, and an active electrode is disposed between the first and second electrode supports, wherein step 902 involves positioning the active electrode on, or adjacent to, a surface of the target tissue.

Step 904 involves delivering an electrically conductive fluid to the shaft distal end, or to the target site, essentially as described for step 802 with reference to FIG. 34A, hereinabove. Step 906 involves applying a high frequency voltage between the active electrode and a return electrode, essentially as described for step 804 with reference to FIG. 34A. Step 908 involves electrosurgically removing tissue from the surgical site. Typically, the target tissue is removed via a process involving molecular dissociation of tissue components in the presence of a plasma. During step 908, the probe is typically manipulated by the surgeon (step 910), such that the active and return electrodes are translated with respect to the target tissue. Step 910 may involve manipulating the probe in one or more of a variety of different ways, depending, for example, on the desired treatment of the target tissue. In one embodiment, the probe may be manipulated in such a manner that the active electrode, or electrode assembly, brushes against a surface of the target tissue to effect vaporization of successive layers of target tissue. In this embodiment, the depth of penetration of the active electrode into the tissue will be considerably less than in the resection embodiment described above.

In one embodiment, step 910 involves manipulating the probe, such that the active electrode, or electrode assembly, is reciprocated with respect to the target tissue. In one aspect of the invention, the probe includes an electrode assembly having an active electrode and a distal return electrode, and the method involves manipulating the probe such that the electrode assembly is axially reciprocated with respect to the target tissue, whereby a slice or fragment of target tissue is resected during each proximal stroke of the reciprocating probe. During the distal stroke of the reciprocating probe, with the distal return electrode at the leading edge of the electrode assembly, any unsealed small blood vessels severed during the proximal stroke may be coagulated by the electric current flowing distally from the proximal active electrode to the return electrode.

According to another aspect of the invention, step 910 may additionally or alternatively involve manipulating the probe such that the probe distal end is inserted into the target tissue, such that the active electrode penetrates the target tissue to a suitable depth, essentially as described hereinabove for step 806 (FIG. 34A). Typically, in this embodiment, the high frequency voltage (step 906) is applied during insertion of the probe within the target tissue. Step 912 involves electrosurgically resecting a fragment of the target tissue for biopsy/tissue analysis. Typically, resection of a tissue fragment, either superficially from the surface of the target tissue, or from within the bulk of the tissue, involves the plasma-induced molecular dissociation of tissue components, as described hereinabove. Ablation by-products, together with any excess electrically conductive fluid, may be removed from the surgical site, essentially as described hereinabove with reference to FIG. 34A.

Using the combination of steps outlined for FIG. 34B, hypertrophied tissue, such as polyps or fibroids of uterine tissue, or that of an enlarged prostate, can be volumetrically removed and, during the same surgical procedure, a sample of the tissue can be removed for biopsy. Moreover, the bipolar electrosurgical removal of tissue according to the instant invention (e.g., step 908), can be precisely controlled, with little or no damage to, or stimulation of, surrounding nerves.

It is to be understood that the electrosurgical apparatus and methods of the invention are by no means limited to the specific embodiments and configurations described hereinabove with reference to the Drawings. Thus, while the exemplary embodiments of the present invention have been described in detail, by way of example and for clarity of understanding, a variety of changes, adaptations, and modifications will be apparent to those of skill in the art. Therefore, the scope of the present invention is limited solely by the appended claims.

What is claimed is:

1. An electrode assembly comprising:
an active electrode coupled to a high frequency power supply, the active electrode having an active surface area;
a return electrode spaced apart from the active electrode, the return electrode comprising a length of a substrate wire coupled to the high frequency power supply and a coil comprised of a coil wire encircling at least a portion of the length of the substrate wire, the return electrode having a return surface area, wherein the return surface area is greater than the active surface area and wherein the current density is lower at a surface of the return electrode than at a surface of the active electrode;
wherein the substrate wire and the coil are separated from the active electrode by an electrode gap, the electrode gap substantially constant over a length of the active electrode; and
wherein a diameter of the substrate wire is greater than a diameter of the coil wire.

2. The electrode assembly of claim 1, wherein the coil is fixed to the substrate wire.

3. The electrode assembly of claim 1, wherein the coil is movable.

4. The electrode assembly of claim 1, wherein the ratio of the return surface area to the active surface area is in the range from about 1.1:1 to about 4:1.

5. The electrode assembly of claim 1, wherein the active and return electrodes substantially lie in a first plane and a second plane, respectively, and wherein the first and second planes are substantially parallel to each other.

6. The electrode assembly of claim 1, wherein the active electrode and substrate wire have substantially similar shapes.

7. The electrode assembly of claim 1, wherein the active electrode and substrate wire have a shape selected from the group comprising a substantially U-shaped, C-shaped, D-shaped and V-shaped.

8. The electrode assembly of claim 1, wherein the active and return electrodes have substantially similar orientations.

9. The electrode assembly of claim 1, wherein the return electrode is located distal to the active electrode.

10. An electrosurgical probe comprising:
a shaft having a distal end;
an electrode assembly as recited in claim 1 disposed on said distal end, wherein said coil wire is helically wrapped around said substrate wire.

* * * * *